US009931039B2

(12) United States Patent
Huang et al.

(10) Patent No.: US 9,931,039 B2
(45) Date of Patent: Apr. 3, 2018

(54) METHODS RELATED TO REAL-TIME CANCER DIAGNOSTICS AT ENDOSCOPY UTILIZING FIBER-OPTIC RAMAN SPECTROSCOPY

(71) Applicant: National University of Singapore

(72) Inventors: Zhiwei Huang, Singapore (SG); Khek Yu Ho, Singapore (SG); Mads Sylvest Bergholt, Singapore (SG); Wei Zheng, Singapore (SG); Khay Guan Yeoh, Singapore (SG); Shiyamala Duraipandian, Singapore (SG)

(73) Assignee: National University of Singapore, Singapore (SG)

(*) Notice: Subject to any disclaimer, the term of this patent is extended or adjusted under 35 U.S.C. 154(b) by 544 days.

(21) Appl. No.: 14/412,053

(22) PCT Filed: Jul. 2, 2013

(86) PCT No.: PCT/SG2013/000273
§ 371 (c)(1),
(2) Date: Dec. 30, 2014

(87) PCT Pub. No.: WO2014/007759
PCT Pub. Date: Jan. 9, 2014

(65) Prior Publication Data
US 2015/0335248 A1 Nov. 26, 2015

Related U.S. Application Data

(60) Provisional application No. 61/667,384, filed on Jul. 2, 2012.

(30) Foreign Application Priority Data

Apr. 23, 2013 (GB) .................................. 1307338.2

(51) Int. Cl.
*A61B 5/02* (2006.01)
*A61B 5/00* (2006.01)
(Continued)

(52) U.S. Cl.
CPC ........ *A61B 5/0075* (2013.01); *A61B 1/00165* (2013.01); *A61B 5/0084* (2013.01);
(Continued)

(58) Field of Classification Search
CPC . A61B 5/0075; A61B 5/0084; A61B 1/00165; A61B 2560/0233; G01N 21/65;
(Continued)

(56) References Cited

U.S. PATENT DOCUMENTS 5,850,623 A 12/1998 Carman, Jr. et al.
5,976,885 A 11/1999 Cohenford et al.
(Continued)

FOREIGN PATENT DOCUMENTS

WO WO2011/072380 6/2011

OTHER PUBLICATIONS

International Publication and International Search Report for PCT/SG2013/000273.
(Continued)

*Primary Examiner* — Mallika D Fairchild
(74) *Attorney, Agent, or Firm* — Garcia-Zamor IP Law; Ruy M. Garcia-Zamor

(57) ABSTRACT

A method of achieving instrument independent measurements for quantitative analysis of fiber-optic Raman spectroscope system, the system comprising a laser source, a spectroscope and a fiber optic probe to transmit light from the laser source to a target and return scattered light to the spectroscope, the method comprising transmitting light from the laser source to a standard target having a known spectrum, recording a calibration spectrum of the scattered light
(Continued)

from the standard target, comparing the known spectrum and the calibration system and generating a probe and/or probe-system transfer function, and storing the transfer function. Further provided is a method of performing real-time diagnostic Raman spectroscopy optionally in combination with the other disclosed methods.

15 Claims, 49 Drawing Sheets

(51) Int. Cl.
*A61B 1/00* (2006.01)
*G01N 21/65* (2006.01)
*G01N 21/27* (2006.01)
*G01J 3/44* (2006.01)

(52) U.S. Cl.
CPC ...... *G01N 21/65* (2013.01); *A61B 2560/0233* (2013.01); *G01J 2003/4424* (2013.01); *G01N 21/274* (2013.01); *G01N 2021/656* (2013.01); *G01N 2201/08* (2013.01); *G01N 2201/129* (2013.01); *G01N 2201/12753* (2013.01)

(58) Field of Classification Search
CPC ............ G01N 21/274; G01N 2201/08; G01N 2201/129; G01N 2201/12753; G01N 2021/656; G01J 3/4412; G01J 3/48; G01J 3/44

See application file for complete search history.

(56) References Cited

U.S. PATENT DOCUMENTS

| 6,351,306 B1* | 2/2002 | Tedesco .............. G01N 21/274 250/458.1 |
| 6,621,574 B1 | 9/2003 | Forney et al. |
| 2003/0191398 A1 | 10/2003 | Motz et al. |
| 2013/0162989 A1* | 6/2013 | Chen ........................ G01J 3/28 356/301 |

OTHER PUBLICATIONS

Written Opinion, Singapore Patent Application No. 11201408793X, dated Sep. 6, 2016.
Second Office Action, SIPO Patent Application No. 201380035488.5, dated Mar. 20, 2017 (original Chinese and English translation).

* cited by examiner

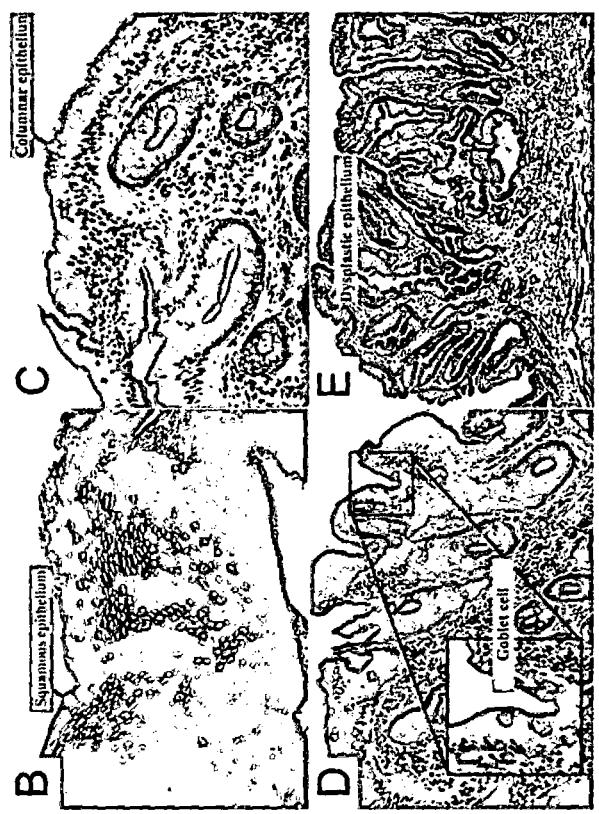
FIG. 40B-E

METHODS RELATED TO REAL-TIME CANCER DIAGNOSTICS AT ENDOSCOPY UTILIZING FIBER-OPTIC RAMAN SPECTROSCOPY

CROSS REFERENCE TO RELATED APPLICATIONS

This application claims priority to the following patent applications: (1) Patent Cooperation Treaty Application PCT/SG2013/000273 filed Jul. 2, 2013; (2) U.S. Patent Application 61/667,384, filed Jul. 2, 2012; and a (3) Great Britain Patent Application 1307338.2, filed Apr. 23, 2013, each of the above cited applications is hereby incorporated by reference herein as if fully set forth in its entirety.

FIELD

The present disclosure relates to an on-line biomedical spectroscopy software platform for real-time cancer diagnostics at endoscopy and methods for instrument-independent measurements for quantitative analysis in fiber-optic Raman spectroscopy.

BACKGROUND

Raman spectroscopy is a technique which uses inelastic or Raman scattering of monochromatic light. Conventionally, the monochromatic light source is a laser in the visible or near infrared ("NIR") range. The energy of the scattered photons is shifted up or down in response to interaction with vibrational modes or excitations in the illuminated material, varying the wavelength of the scattered photons. Accordingly, the spectra from the scattered light can provide information about the scattering material.

NIR Raman spectroscopy is known as a potential technique for characterisation and diagnosis of precancerous and cancerous cells and tissue in vivo in a number of organs. The technique is desirable as it can be non-invasive or minimally invasive, not requiring biopsies or the other removal of tissue. It is known to use NIR Raman spectroscopy in two wavelength ranges. The first is the so-called fingerprint ("FP") range, with wave numbers from 800 to 1800 $cm^{-1}$, owing to the wealth of highly specific bimolecular information, for example from protein, DNA and lipid contents, contained in this spectral region for tissue characterisation and diagnosis. The disadvantage of this wavelength range is, that when used with a commonly used 785 nm laser source, the strong tissue autofluorescence background signal can be generated. Further, where the probe uses optical fiber, a Raman signal is scattered from the fused silica in the optical fibers. In particular, where a charge-coupled device ("CCD") is used to measure the scattered spectra, the autofluorescence signal can saturate the CCD and interfere with the detection of the inherently very weak Raman signals in this wavelength range.

Another problem with fiber-optic Raman spectroscopy as a technique is that of standardization of instruments. The fiber-optic Raman spectroscopy technique has mainly been limited to single systems and no attempts have been made to transfer into multi-centre clinical trials or routine medical diagnostics. This is mainly because Raman spectrometer instruments are generally dissimilar (i.e., optics, response function, alignment, throughput etc.) and in general produce very different Raman spectra. Further, fiber optic Raman probes have limited lifetimes and must be replaced or interchanged periodically. Unfortunately, Raman data acquired using different fiber optic probes cannot be compared, because each fiber optic probe has its own unique background as well as being associated with different transmissive spectral properties. The different transmissive characteristics significantly distort the spectral intensities making the tissue Raman spectra obtained with different fiber optic probes incomparable. As a consequence, multivariate diagnostic algorithms developed on a primary clinical platform cannot be applied to secondary clinical platforms. In particular, the quantitative measurement of tissue Raman intensity is one of the most challenging issues in fiber optic biomedical Raman applications. The instrument/fiber probe-independent intensity calibration and standardization is essential to the realization of global use of fiber optic Raman spectroscopy in biomedicine. For this reason, a multivariate statistical diagnostic model constructed using a 'master' probe cannot be applied to spectra measured with a 'slave' probe. In order for Raman technique to become a widespread tool for cancer screening on a global scale, there is a need to standardize both Raman spectrometers and fiber optic probes especially for biomedical applications. Most of the reported studies have focused on inter-Raman spectrometer standardization for measurements of simple chemical mixtures without fiber optic probes. In general Raman spectroscopy of simple chemical mixtures cannot be compared with the fiber optic Raman spectroscopy of heterogeneous biological tissue samples.

A further problem with standardizing results across instruments is that of spectral variation associated with the laser excitation power. Conventionally, Raman spectra are normalized which preserves the general spectrum shape, but this removes the absolute quantitative spectral characteristics. It has been known to attempt to monitor delivered laser power in fibre-optic Raman probes by, for example, embedding a diamond in the fibre tip or locating a polymer cap in the laser light path as a reference. However, these solutions are not satisfactory and may cause interferences in the required spectral regions.

A further problem in using optical spectroscopic techniques (including reflectance fluorescence and Raman) for in vivo diagnosis of cancer and precancerous conditions is that data analysis mostly been limited to post-processing and off-line algorithm development. This is true for endoscopic analysis because a large number of spectra collected during endoscopy are outliers. It would be useful to have a system that allows for real-time diagnosis for endoscopy.

SUMMARY

According to a first aspect there is provided a method of calibrating a fiber-optic Raman spectroscope system, the system comprising a laser source, a spectroscope and a fiber optic probe to transmit light from the laser source to a target and return scattered light to the spectroscope, the method comprising transmitting light from the laser source to a standard target having a known spectrum, recording a calibration spectrum of the scattered light from the standard target, comparing the known spectrum and the calibration system and generating a transfer function, and storing the transfer function.

The method may further comprise the steps of subsequently illuminating a test subject, recording a spectrum and correcting the spectrum in accordance with the stored transfer function.

The method may comprise recording calibration spectra for each of a plurality of fiber optic probes, calculating a transfer function for the system including each of said probes, and associating the transfer function with the corresponding probe.

The spectrometer has an associated spectrometer transfer function and the probe may have an associated probe transfer function, and the transfer function may be a function of the spectrometer transfer function and the probe transfer function.

The method may comprise, on a primary spectrometer system, calculating a first transfer function with a primary fiber optic probe, and a second transfer function with a secondary fiber optic probe, and calculating a (inter-probe) calibration function based on the first transfer function and second transfer function.

The method may comprise associating the calibration function with the secondary fiber optic probe.

The method may comprise, on a secondary spectrometer system, using the primary fiber optic probe and generating a secondary system transfer function and storing the secondary system transfer function.

The method may comprise using the secondary fiber optic probe with the secondary spectrometer system and modifying the stored secondary system transfer function in accordance with the calibration function.

The method may comprise the initial step of performing a wavelength-axis calibration of the secondary spectrometer system in accordance with the primary spectrometer system.

According to a second aspect there is provided a method of operating a Raman spectroscope system, the system comprising a laser source, a spectroscope and a fiber optic probe to transmit light from the laser source to a target and return scattered light to the spectroscope, the method comprising transmitting light from the laser source to a target having a known spectrum, recording a spectrum of the scattered light from the target, and modifying the recorded spectrum in accordance with a stored transfer function.

The stored transfer function may be associated with the spectrometer and the fiber optic probe.

The stored transfer function may be associated with the spectrometer and a primary fiber optic probe and the method may further comprise modifying the stored transfer function in accordance with a stored calibration function associated with the fiber optic probe.

According to a third aspect there is provided a Raman spectroscope system comprising a laser source, a spectroscope and a fiber optic probe to transmit light from the laser source to a target and return scattered light to the spectroscope, and a stored transfer function, the system being operable to transmit light from the laser source to a target having a known spectrum, record a spectrum of the scattered light from the target, and modify the recorded spectrum in accordance with the stored transfer function.

The stored transfer function may be associated with the spectrometer and the fiber optic probe.

The stored transfer function may be associated with the spectrometer and a primary fiber optic probe and the method may further comprise modifying the stored transfer function in accordance with a stored calibration function associated with the fiber optic probe.

According to a fourth aspect there is provided a method of estimating the laser power transmitted in a Raman spectrometer system, the system comprising a laser source, a spectroscope and a fiber optic probe to transmit light from the laser source to a target and return scattered light to the spectroscope, the method comprising transmitting light from the laser source to a plurality of targets, for each target, measuring the transmitted power of the light from the laser source and the spectrum of the scattered light at the spectroscope, performing a multivariate analysis of the captured spectra with the measured transmitted power as a dependent variable, and storing a resulting model.

The method may comprise the step of transmitting laser light to a test target, supplying a captured spectrum to the model, and calculating an estimate of the transmitted power.

According to a fifth aspect there is provided a method of subtracting a background signal from a fiber-optic Raman spectroscope system having a fiber-optic probe, the method comprising the steps of;
a) storing a background spectrum,
b) receiving a test spectrum,
c) estimating a background contribution using one or more reference peaks,
d) multiplying the background spectrum by a correction factor based on the estimated background contribution and subtracting it from the test spectrum,
e) checking the test spectrum for a remaining background contribution, and
f) if the background contribution is negligible, outputting the test spectrum, otherwise repeating steps (c) to (e).

The one or more reference peaks may comprise one or more peaks corresponding to silica or sapphire in the fiber-optic probe.

According to a sixth aspect there is provided a computer implemented method for real-time diagnosis using Raman spectroscopy during endoscopy. The method comprises receiving at least one spectrum associated with a tissue; analyzing the at least one spectrum in a model that uses the spectrum to determine a score wherein said score indicates a likelihood of the tissue being cancerous; and outputting said score.

In some embodiments the model is generated using an interpretation function selected from the group consisting of partial least squares-discriminant analysis, principal component analysis linear discriminant analysis, ant colony optimization linear discriminant analysis, classification and regression trees, support vector machine, and adaptive boosting.

In some embodiments the at least one spectrum is generated by Raman spectroscopy. Analyzing the at least one spectrum in a model may comprise analyzing the at least one spectrum in a first model and a second model. In some embodiments the model is selected based on the tissue analyzed. In some embodiments the score indicates whether the tissue is normal, intestinal metaplasia, dysplasia or neoplasia.

In some aspects analyzing the at least one spectrum comprises: performing outlier analysis; and responsive to the outlier analysis determining that the at least one spectrum is an outlier, rejecting the spectrum. Performing outlier analysis may comprise principal component analysis.

In some aspects an audio emitting device emits an audio signal responsive to the outlier analysis determining that the at least one spectrum is an outlier. Responsive to the determination that the spectra is an outlier method instructs the spectrometer to acquire an additional at least one spectrum which is received by the system for analysis.

In some embodiments, the audio emitting device to emit an audio signal identifying the tissue as normal, dysplasia or neoplasia. In some embodiments, the audio signal associated with each diagnosis is different and also different from an audio signal associated with the determination of an outlier spectrum.

In some embodiments, the diagnosis takes place during the endoscopic procedure.

Also provided are systems for carrying out the computer-implemented methods as well as non-transitory computer readable media with instructions thereon for carrying out the computer-implemented methods.

BRIEF DESCRIPTION OF THE DRAWINGS

Embodiments of the disclosed system and methods are described by way of example only with reference to the accompanying drawings.

FIG. 1a is a view of the end of the endoscope of FIG. 1 on a larger scale.

FIG. 1b is a view of the Raman probe of the endoscope of FIG. 1a in more detail.

FIGS. 40B-E illustrate B) Representative histological sectioned-slides (hematoxylin and eosin (H&E) stained) corresponding to the measured tissue sites. Squamous lined epithelium (C) Columnar lined esophagus with absence of goblet cells, ×200; (D) Barrett's esophagus where the normal stratified squamous epithelium is replaced by intestinal metaplastic epithelium containing goblet cells, ×200; (E) High-grade dysplasia showing both architectural and cytological atypia as well as crowded crypts with branching and papillary formation, cytological pleomophism and loss of polarity; ×100.

DETAILED DESCRIPTION OF THE PREFERRED EMBODIMENTS

Figure 1:
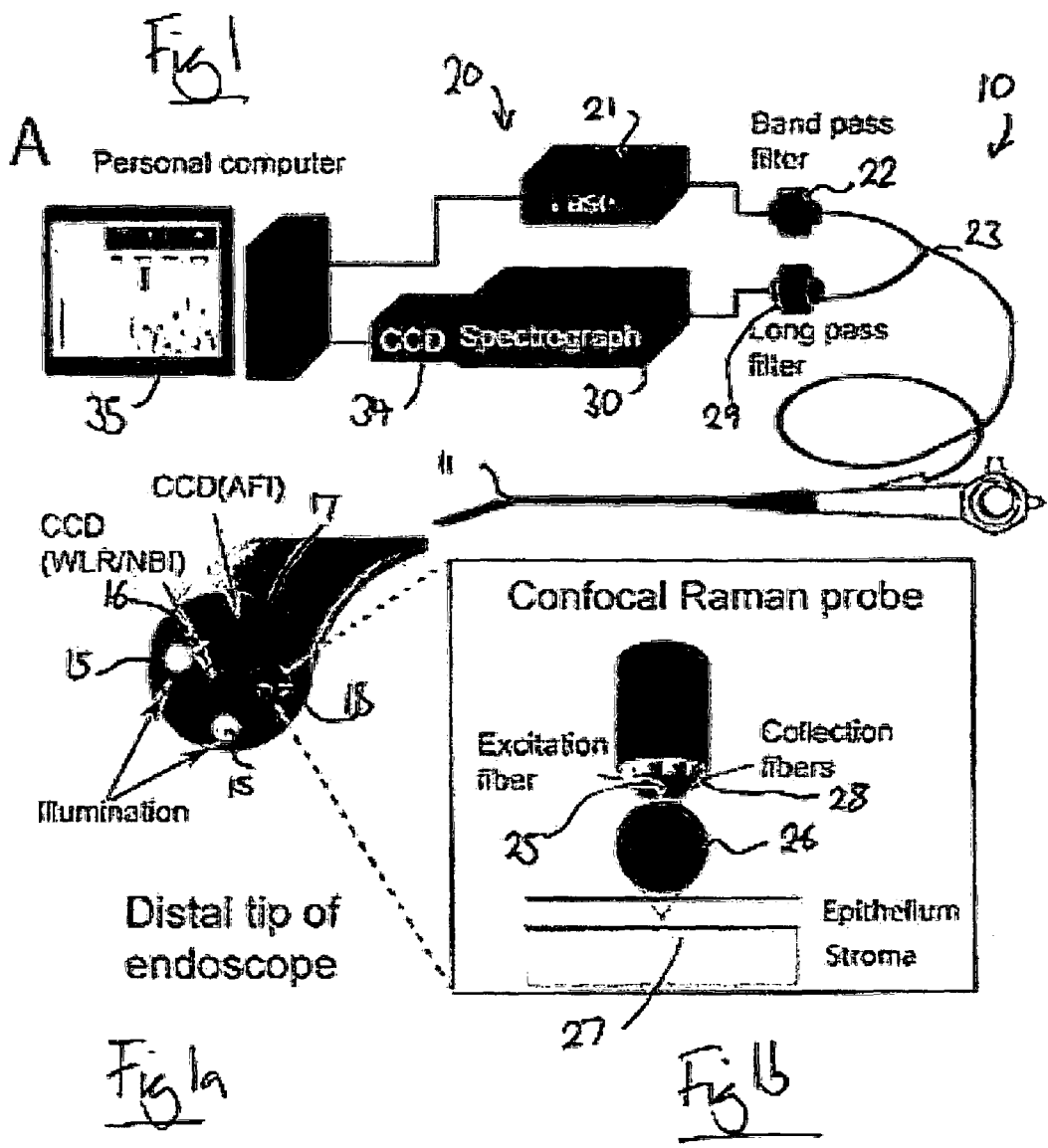
FIG. 1 is a diagrammatic illustration of a Raman spectroscopic system according to one embodiment.

Provided herein is an on-line system and method for biomedical spectroscopy (i.e., reflectance, fluorescence and Raman spectroscopy) for realizing real-time detection of neoplastic lesions in different organs (e.g., gastrointestinal tracts (stomach, esophagus, colon), bladder, lung, oral cavity, nasopharynx, larynx, cervix, liver, skin, etc.) at endoscopy. The diagnostic method integrates excitation source synchronization, integration-time adjustment, data acquisition, preprocessing, outlier analysis and probabilistic multivariate diagnostics (i.e., partial least squares-discriminant analysis (PLS-DA), principal component analysis (PCA)-linear discriminant analysis (LDA), ant colony optimization (ACO)-LDA, classification and regression trees (CART), support vector machine (SVM), adaptive boosting (AdaBoost) etc.) including multi-class diagnostics based on comprehensive spectral databases (i.e., Raman, fluorescence, reflectance) of different organs.

In one embodiment, the disclosed system and method integrates the on-line diagnostic framework with the recently developed multimodal image-guided (WLR/NBI/AFI) Raman spectroscopic platform for early diagnosis and detection of precancer and cancer in the upper GI at endoscopy. The accumulation of tissue Raman spectra and automatic scaling of integration time with a predefined upper limit of 0.5 s allows instant acquisition of in vivo tissue spectra with improved SNR while preventing CCD signal saturation. This is especially important for endoscopic diagnostics where the autofluorescence intensity varies significantly among different anatomical regions (e.g., antrum and body in the gastric, bronchi in the lung) likely caused by distinct endogenous fluorophores in the tissue.

With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the disclosed system and methods. In this regard, no attempt is made to show structural details of the disclosed system and methods in more detail than is necessary for a fundamental understanding of the disclosed system and methods, the description taken with the drawings making apparent to those skilled in the art how the several forms of the disclosed system and methods may be embodied in practice.

Before explaining at least one embodiment of the disclosed system and methods in detail, it is to be understood that the disclosure is not limited in its application to the details of construction and the arrangement of the components set forth in the following description or illustrated in the drawings. The disclosed system and methods are applicable to other embodiments or of being practiced or carried out in various ways. Also, it is to be understood that the phraseology and terminology employed herein is for the purpose of description and should not be regarded as limiting.

Referring now to FIG. 1, a diagnostic instrument comprising an endoscope system according to one embodiment is shown at 10. The endoscope itself is shown at 11 and an instrument head of the endoscope 11 is generally illustrated in FIG. 1a. To provide for guidance and visual viewing of the area being tested, the endoscope 11 is provided with a suitable video system. Light from a xenon light source is transmitted to illumination windows 15 in the end of the endoscope 12. CCDs 16 and 17, responsive to white light reflection imaging, narrowband imaging or autofluorescence imaging, receive the reflected light and transmit video data to allow for visual inspection of the tested tissues and for guidance of the endoscope to a desired position. The confocal Raman probe head is showing at 18, and in more detail in FIG. 1b.

The Raman spectroscopy system is generally shown at 20. A monochromatic laser source is shown at 21, in the present example a diode laser with an output wavelength of about 785 nm. Light from the laser diode 21 is passed through a proximal band pass filter 22, comprising a narrowband pass filter being centred at 785 nm with a full width half max of ±2.5 nm. The light is passed through a coupling 23 into an excitation optical fiber 25 provided as part of a fiber bundle. The excitation fiber 25 has a diameter of 200 µm and a numerical aperture ('NA') of 0.22. Light transmitted by the excitation fiber 25 enters a ball lens 26 at the end of the endoscope 11, in the present example comprising a sapphire ball lens with a diameter of about 1.0 mm and a refractive index n=1.77. As illustrated in FIG. 1b, transmitted light from the excitation optical fiber 25 is internally reflected within the ball lens 26. Where the ball lens is in contact with the tissue to be tested, as shown here at 27, the transmitted light from the excitation fiber 25 at least in part undergoes Raman scattering within the tissue 27, to a depth of ~140 µm. The scattered light is again internally reflected in the ball lens 26 and received in a plurality of collection fibers 28, also provided as part of the fiber bundle. In the present example twenty-six 100 µm collection fibers are used, with an NA of 0.22. The collection fibres 28 may be arranged in any suitable configuration, for example in a circular arrangement surrounding the excitation fiber 25.

Collected scattered light returned by collection fibers 28 is passed through a long pass inline collection filter 29 which similarly has a cutoff at ~800 nm. The configuration of sapphire ball lens 26, excitation and collection fibers 25, 28, band-pass filters 22, and long-pass filter 29 provides a good system for selectively collecting backscattered Raman photons from the tissue 27.

The scattered returned light is then separated at spectrograph 30 and the resulting spectrum is imaged at a light-sensing array 34, in the present example a charge-couple device ('CCD'). A computer shown at 35 controls the operation of the system, processes and stores the spectra and control data, and provides results and data to a user.

In one embodiment, the computer 35 comprises at least one processor coupled to a chipset. Also coupled to the chipset are a memory, a storage device, a keyboard, a graphics adapter, a pointing device, an audio emitting device and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer 35 can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The computer 35 also performs preprocessing the spectral data. As the measured tissue Raman spectra are substantially obscured by the tissue autofluorescence background, preprocessing of in vivo tissue Raman spectra is necessary to extract the weak Raman signals. The raw Raman spectra measured from in vivo tissue represent a combination of the weak Raman signal, intense autofluorescence background, and noise. The spectra are first normalized to the integration time and laser power. The spectra are then smoothed using a first-order Savitzky-Golay smoothing filter (window width of 3 pixels) to reduce the noise. A fifth-order polynomial was found to be optimal for fitting the autofluorescence background in the noise-smoothed spectrum, and this polynomial is then subtracted from the raw spectrum to yield the tissue Raman spectrum alone. The computer 35 can also including diagnostic algorithms for precancer and cancer detection.

Spectrometer and Fibre-Optic Probe Calibration

Figure 2:
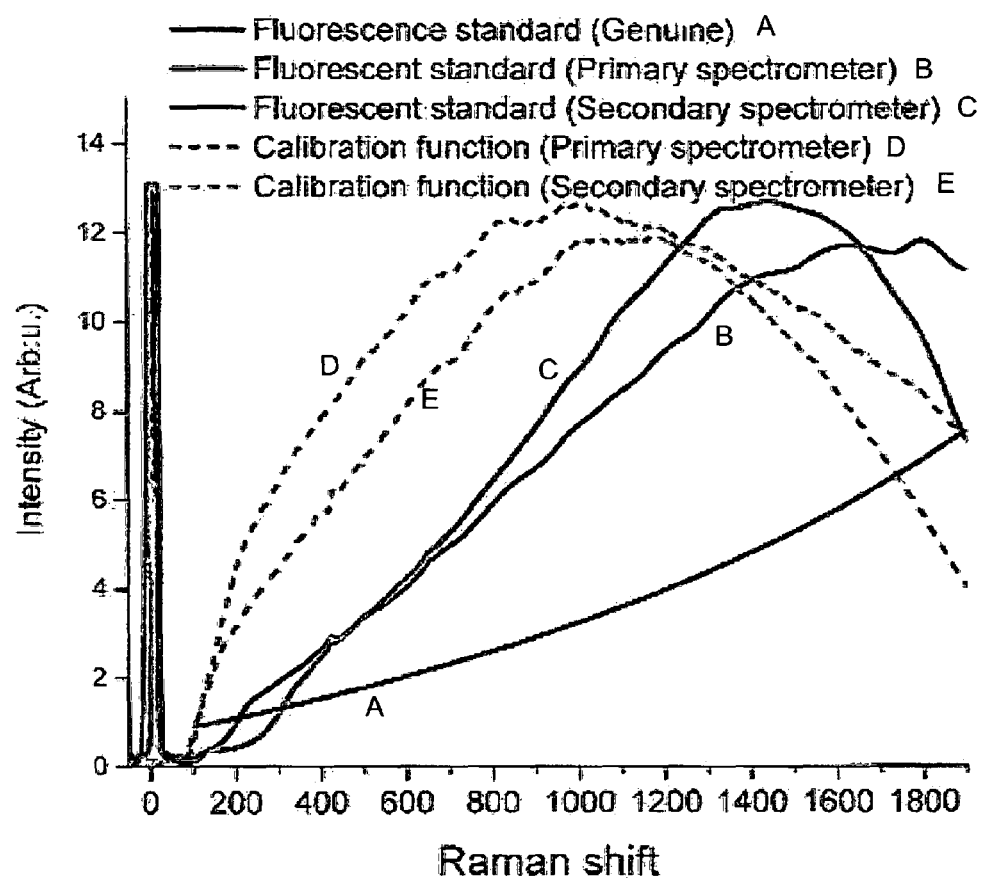
FIG. 2 is a graph illustrating a comparison of measured fluorescence spectra to a reference standard. The calibration functions are also shown.

It is known that different spectrometers will have different transfer functions, i.e. will show differing intensity variations within spectra even when illuminated using the same source. As illustrated in FIG. 2, the spectrum from a standard source is shown. The standard source in this example is a fluorescent standard target that emits a known fluorescent spectrum when excited by a laser such as laser source 21. The fluorescent standard target must be consistent and stable and emit a broad fluorescence spectrum under a laser excitation (e.g., 785 nm). The fluorescence spectrum must be stable over time and efficiently characterize the spectral transmissive properties over the entire spectral region of interest (e.g., 400-1800 cm$^{-1}$, 2000-3800 cm$^{-1}$). An example is chromium-doped glass. The resulting spectra from two spectrometers are shown, which are clearly different. To compensate for the spectrometer response, or transfer function, it is known to apply a calibration function which will correct the spectrum received from the spectrometer. Examples and calibration functions are shown in FIG. 2 which, when applied to the corresponding spectrum of the spectrometer, will bring the spectrum into line with the known standard spectrum.

Using a fluorescent standard source, the transfer function, i.e. the wavelength-dependent response of the spectrometer, can be given by $$F(\lambda) = \frac{S(\lambda)}{T(\lambda)}$$

(eqn. 1) where $F(\lambda)$ is the correct fluorescent standard spectrum, $S(\lambda)$ is the measured spectrum of the fluorescent standard source and $T(\lambda)$ is the transfer function of the spectrometer. Accordingly, as $T(\lambda)$ is known, a correctly calibrated Raman spectrum of a new sample $R(\lambda)$ can be calculated by $$R(\lambda) = \frac{S(\lambda)}{T(\lambda)}$$

(eqn. 2) where $S(\lambda)$ is the measured sample spectrum.

The transfer function $T(\lambda)$ is a function both of the spectrometer transfer function $T_S(\lambda)$ and a probe transfer function $T_P(\lambda)$. Equation 2 can therefore be written as $$R(\lambda) = \frac{S(\lambda)}{T_S(\lambda)T_P(\lambda)}$$

(eqn. 3). As fibre-optic probes are replaceable and may be consumables, it will be apparent that when a new probe with a new probe transfer function $T_P$ is inserted, the overall transfer function of the system will change.

Figure 3:
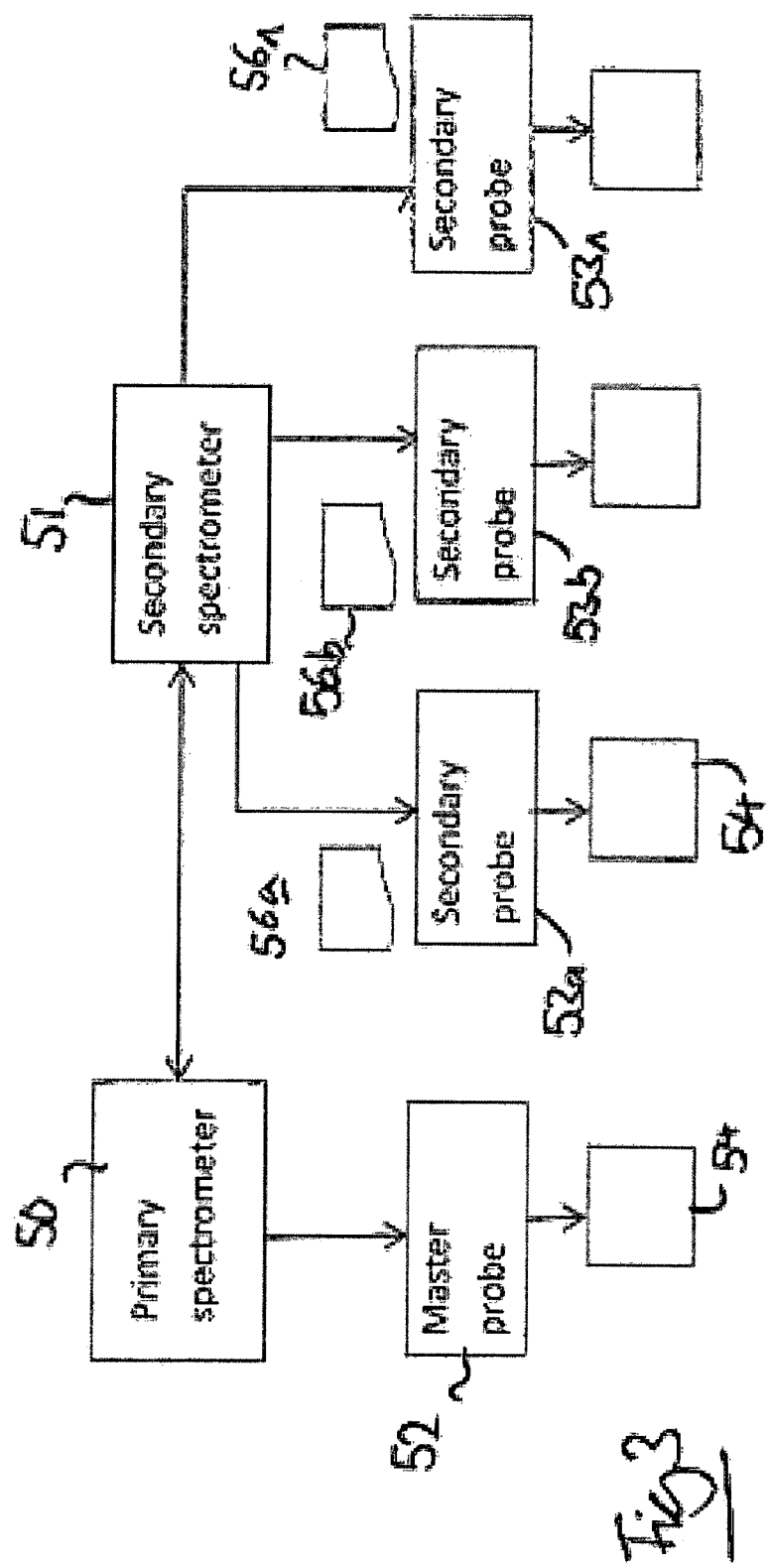
FIG. 3 is a diagrammatic illustration of a first calibration method.

Referring now to FIG. 3, a primary or master spectrometer is shown at 50 and a secondary or slave spectrometer is shown at 51. The spectrometers 50, 51 each have a configuration similar to that shown in FIG. 1, but may have different fibre probes and spectrograph characteristics. Ideally, the personal computer 35 controlling each spectrograph uses a common library of programs to provide control of the system and data processing, and it is therefore desirable that characteristics of the primary and secondary spectrometers 50, 51 are consistent. In this example, the primary spectrometer 50 is associated with the primary or master probe 52, and the secondary spectrometer 51 is associated with a plurality of secondary or slave probes shown at 53a, 53a, 53b. In each case, the calibration is performed with reference to a standard fluorescent source diagrammatically illustrated at 54.

Figure 4A:
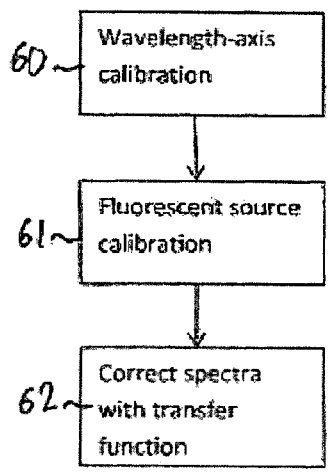
FIG. 4a is a flow chart showing a first process for use with the first calibration method.
Figure 5:
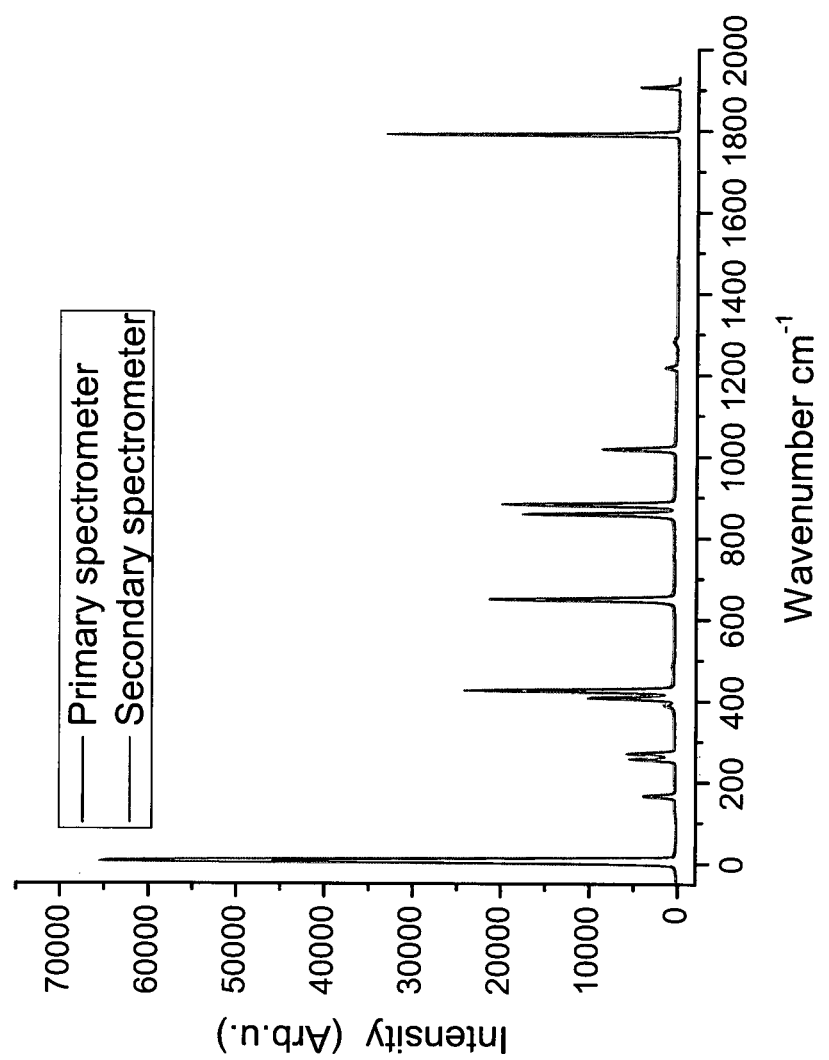
FIG. 5 is a graph showing the wavelength alignment of an argon/mercury lamp among a primary spectrometer and a secondary spectrometer.

A first method of calibration is shown in FIG. 4a. At step 60, the secondary spectrometer is wavelength calibrated in accordance with the primary spectrometer. In this case, wavelength-axis calibration of the secondary spectrometer 51 is performed, for example using an argon-mercury spectral lamp or a chemical sample with defined spectral lines, and pixel resolution matching using linear interpolation is then performed to ensure that the size of the axis of the second spectrometer matches that of the primary spectrometer. The results of this calibration are shown in FIG. 5, where the spectra from the primary and secondary spectrometers 50, 51 show the spectral lines from the lamp precisely aligned. At step 61, calibration is performed for the second spectrometer and the probe 53a using a fluorescent source 54. In a similar manner to the graph of FIG. 2, a spectrum will be recorded from the fluorescent source, and a transfer function can then be calculated to bring the measured spectrum into line with the known spectrum, and stored, for example by the personal computer 35. At step 62, the spectrometer 51 may then be used for in vivo Raman testing or otherwise, and the measured Raman spectra can be corrected using the calibration function recorded at step 61.

When probe 53a is discarded and it is desired to carry out tests on a new subject, a replacement probe 53b may be substituted, in which case the method of FIG. 4a is repeated.

Figure 4B:
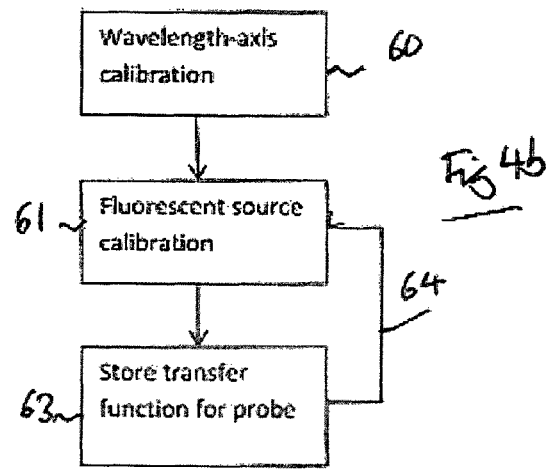
FIG. 4b is a flow chart showing a first part of a second process for use with the first calibration method.
Figure 4C:
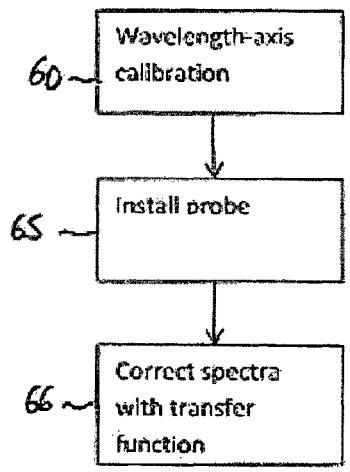
FIG. 4c is a flow chart showing a second part of a second process for use with the first calibration method.

In an alternative process as illustrated in FIGS. 4b and 4c, a plurality of calibration functions may first be recorded for the secondary spectrometer and a plurality of secondary probes. At step 60 in FIG. 4b, as in FIG. 4a, the secondary spectrometer 51 is calibrated for consistency with primary spectrometer 60. At step 61, a calibration function for secondary probe 53a is measured, and at step 63 this calibration function is stored and associated with probe 53a in some way, for example by saving the calibration function as a computer file 56a tagged with a reference number corresponding to the secondary probe 53a. As shown by arrow 64, this process is then repeated for any number of probes 53b, ..., 53n to provide a stock or reserve of probes. As shown in FIG. 4c, when it is desired to carry out testing using the spectrometer 51, at step 60 the spectrometer is calibrated in accordance with the primary spectrometer 50 as above. At step 65 probe 53n is installed on the system and a corresponding stored transfer function 56n retrieved. At step 66, tests using the secondary spectrometer 51 may be performed and calibrated using the retrieved calibration function 56n.

An alternative approach is illustrated with reference to FIG. 6, in which the slave or secondary probes 53a, ..., 53n are calibrated on the primary or master 50. In accordance with equation 2, where the primary spectrometer is tested with a primary or master probe with transfer function $T_{PP}(\lambda)$ and a secondary or slave probe with transfer function $T_{SP}(\lambda)$, the spectrum from the fluorescent source $F(\lambda)$ will result in a spectrum $S_{PP}(\lambda)$ for the primary probe, where $$F(\lambda) = \frac{S_{PP}(\lambda)}{T_S(\lambda)T_{PP}(\lambda)}$$

(eqn. 4) and a spectrum $S_{SP}(\lambda)$ using the secondary probe, where $$F(\lambda) = \frac{S_{SP}(\lambda)}{T_S(\lambda)T_{SP}(\lambda)}$$

(eqn. 5). Equations 4 and 5 can be divided to relate the two probe transfer values through a probe calibration function $T_{CF}$, where $$T_{CF} = \frac{T_{SP}(\lambda)}{T_{PP}(\lambda)} = \frac{S_{SP}(\lambda)}{S_{PP}(\lambda)}$$

(eqn. 6). Consequently, from equations 2 and 6, when the secondary spectrometer is used with the secondary probe, the measured spectrum $S(\lambda)$ and Raman spectrum $R(\lambda)$ are related by $$R(\lambda) = \frac{S(\lambda)}{T_S(\lambda)T_{SP}(\lambda)} = \frac{S(\lambda)}{T(\lambda)T_{CF}}$$

(eqn. 7) where $T(\lambda)=T_S(\lambda)T_{PP}(\lambda)$ is the stored system transfer function measured for the secondary spectrometer using the master probe.

Figure 6:
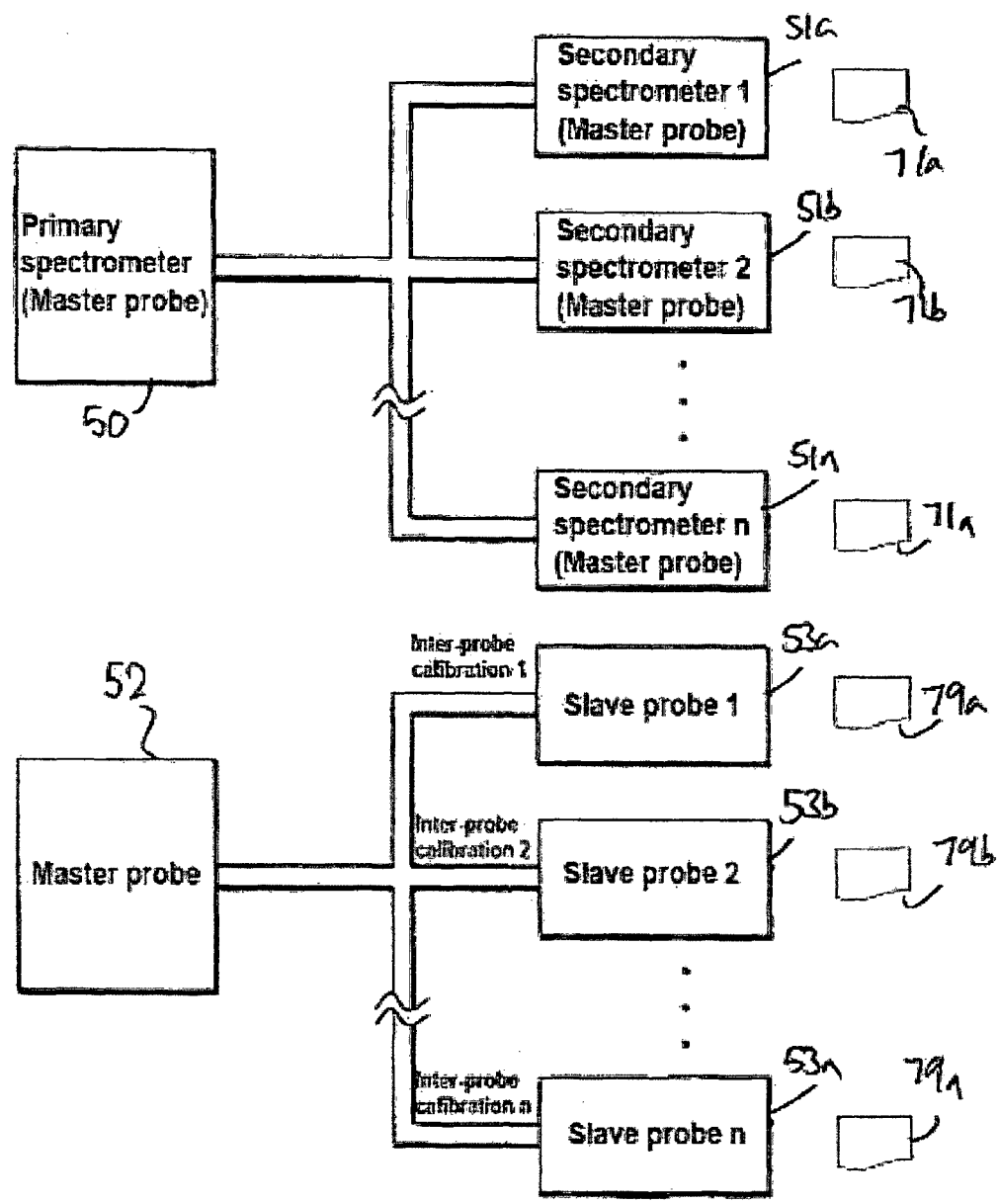
FIG. 6 is a graph showing the spectral calibration of a primary spectrometer and a secondary spectrometer using second calibration method.
Figure 7A:
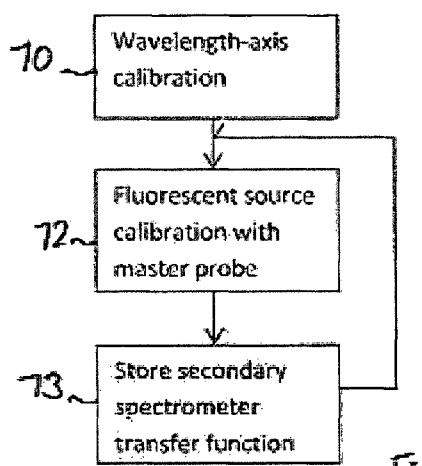
FIG. 7a is a flow chart showing a first process for use with the first calibration method.
Figure 7B:
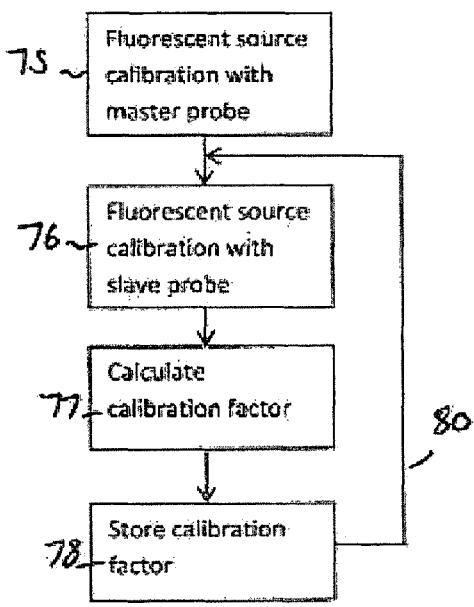
FIG. 7b is a flow chart showing a first part of a second process for use with the second calibration method.
Figure 7C:
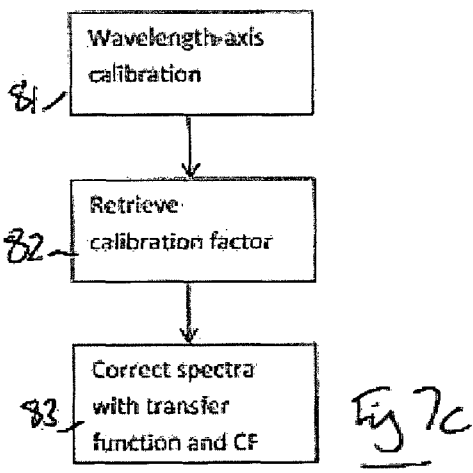
FIG. 7c is a flow chart showing a second part of a second process for use with the second calibration method.

As illustrated in FIGS. 6 to 7c, this allows any number of secondary or slave probes 53a, 53b, 53n to be matched to any number of secondary spectrometers 51a, 51b, 51n. As shown in FIG. 7a, at a first step 70 the secondary spectrometer 51a is calibrated in accordance with primary spectrometer 50 in similar manner to step 60, using the master probe 52. The system transfer function 71a is found at step 72 by testing the secondary spectrometer against a fluorescent standard source 54 in like manner to the method of FIGS. 3 to 4c. The system transfer function 71a is associated with the corresponding spectrometer 51a in any appropriate manner, for example in the control software or otherwise at step 73. As shown by arrow 74, this may be repeated for any number of secondary spectrometer systems 51b, ... 51n, to generate appropriate system transfer functions 71b, ... 71n.

As shown in FIG. 7b, the secondary or slave probes 53a, 53b, . . . , 53n are calibrated against the master probe 52. At step 75, the primary spectrometer system 50 is suitably calibrated with the master probe against a fluorescent source 54, although this may be omitted if this step has already been performed and the transfer function associated with the master probe already stored. At step 76, the master probe is replaced by probe 53a, and the combination of the primary spectrometer system and corresponding slave probe then tested against a fluorescent standard 54. At step 77, a calibration function $T_{CF}$ is calculated from the ratio of the primary and secondary probe spectra and at 78 this is recorded and stored associated with the secondary probe as shown at 79a. As shown by arrow 80, this can be repeated for any number of secondary probes 53b, . . . 53n and the corresponding calibration function $T_{CF}$ stored as shown at 79b, . . . 79b.

As illustrated in FIG. 7c, one of the secondary spectrometer systems 51n may be used with any one of the secondary probes 53n, as the system transfer function 71a using the master probe 52 is known and the calibration function $T_{CF}$ relating the secondary probe 53n to the master probe 52 is known. As shown at step 81, the secondary spectrometer system 51n is calibrated in accordance with the primary spectrometer system 50. At step 82, the secondary probe calibration function $T_{CF}$ is retrieved and the store system transfer function 71n modified in accordance with the stored calibration function $T_{CF}$. At step 83, in vivo Raman tests or otherwise can then be performed and the captured Raman spectra corrected.

In any of the methods therefore, by matching the secondary spectrometer characteristics back to the primary spectrometer characteristics, and storing either the transfer function for the spectrometer and probe combination or a transfer function for the system incorporating a master probe and a calibration function for use with a secondary probe, spectra captured using different spectrometer and probe combinations will nevertheless be consistent and comparable.

Figure 8:
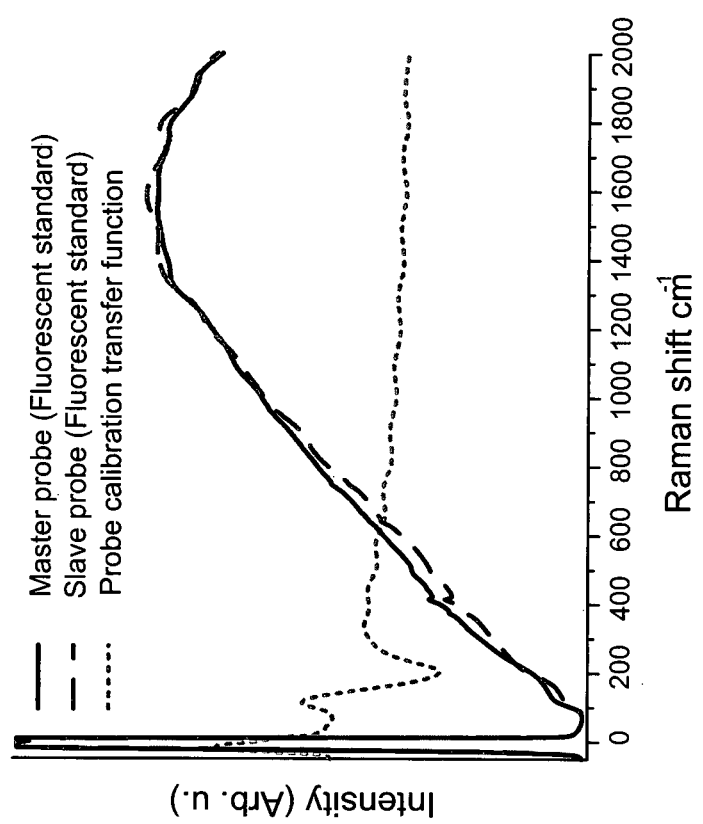
FIG. 8 is a graph showing fluorescent standards measured with master and slave probes and a probe calibration transfer function.
Figure 9:
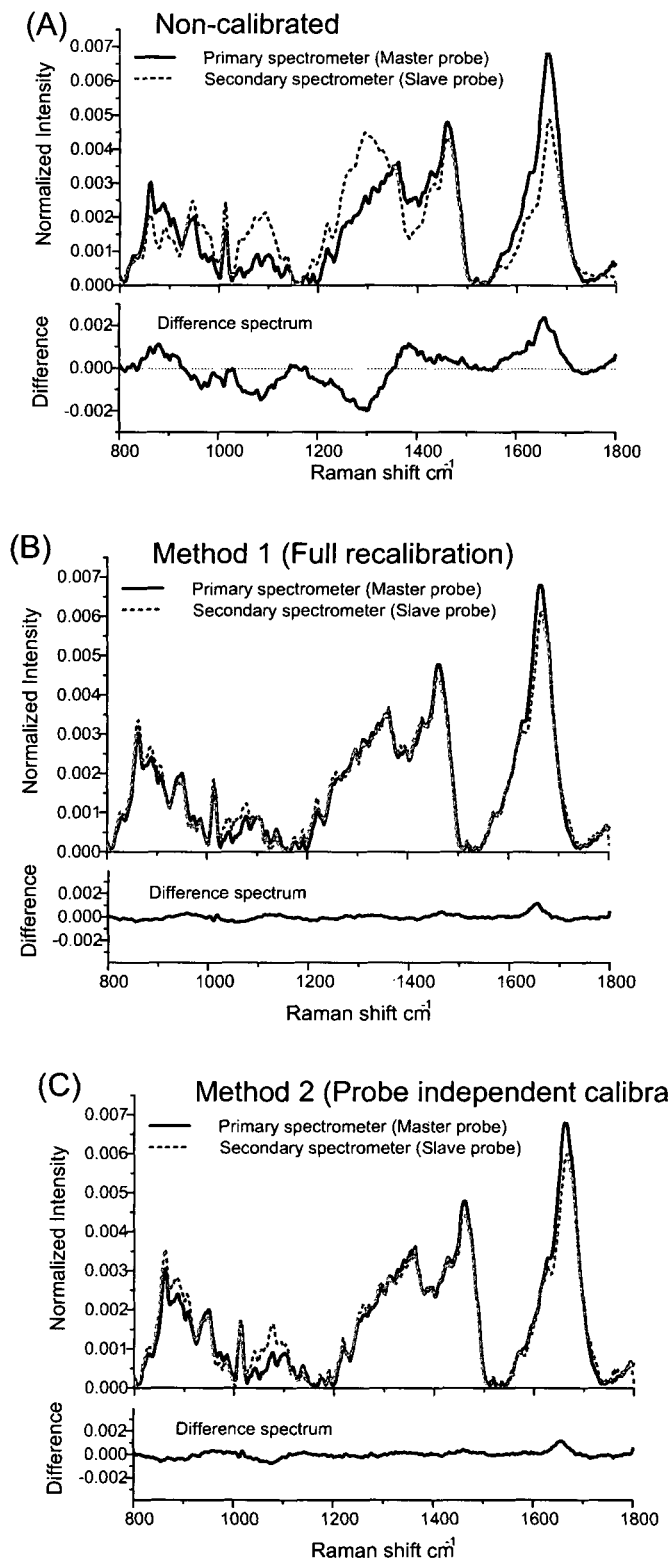
FIG. 9a is a graph of tissue Raman spectra comparing uncalibrated primary and secondary spectrometers with master and slave probe respectively.
FIG. 9b is a graph of tissue Raman spectra from primary and secondary spectrometers with master and slave probe respectively after recalibration using a first calibration method.
FIG. 9c is a graph showing spectra from primary and secondary spectrometers with master and slave probe respectively after recalibration using a second calibration method.

This is apparent from FIG. 8 and FIGS. 9a to 9c. FIG. 8 shows different responses between the master probe 52 and a secondary or slave probe 53n. The intensity response varies over the spectrum, and the calibration function as shown would map the spectrum of the secondary probe to that of the main or master probe. Uncalibrated tissue spectra from a primary spectrometer 50 and a secondary spectrometer 51 are shown in FIG. 9a and the differences between them are apparent. FIGS. 9b and 9c show the results of calibration using each of the methods shown above and the spectra from the primary and secondary spectrometer are substantially in agreement.

Figure 10:
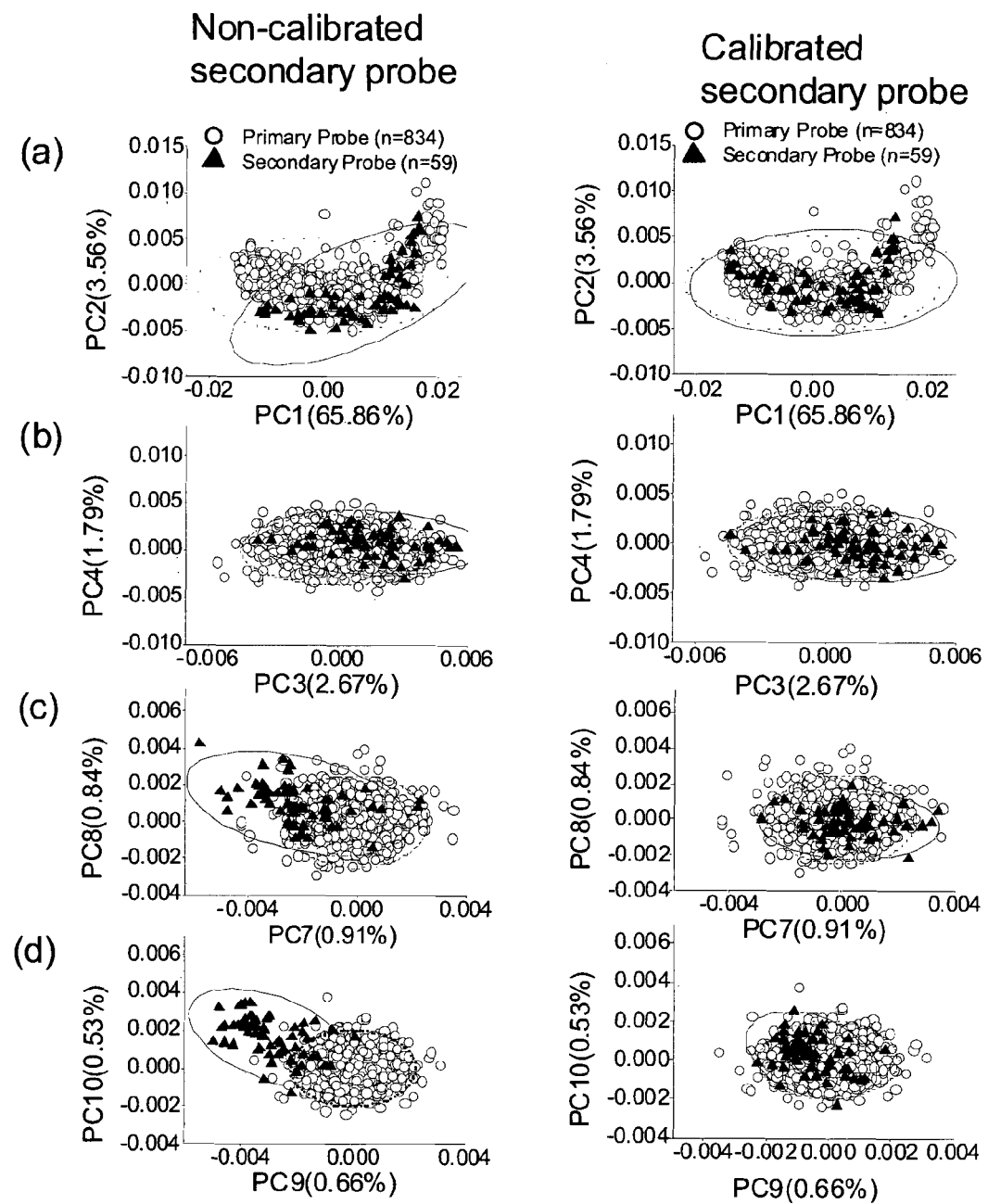
FIG. 10 Principal component analysis score scatter plot on in vivo tissue Raman spectra from the gastric before and after calibration.

Raman spectra were measured from the gastric with two different probes (n=902 spectra). A principal component analysis (PCA) was conducted before and after calibration of the secondary probe. FIG. 10 shows the PCA analysis before and after calibration of the fiber-optic probe as well as the 95% confidence interval on different scores. It is evident that after calibration of the fiber-probe, the spectra falls within the same confidence interval indicating a successful transfer among the master and slave fiber-optic Raman probes.

Monitoring Laser Power

Figure 11:
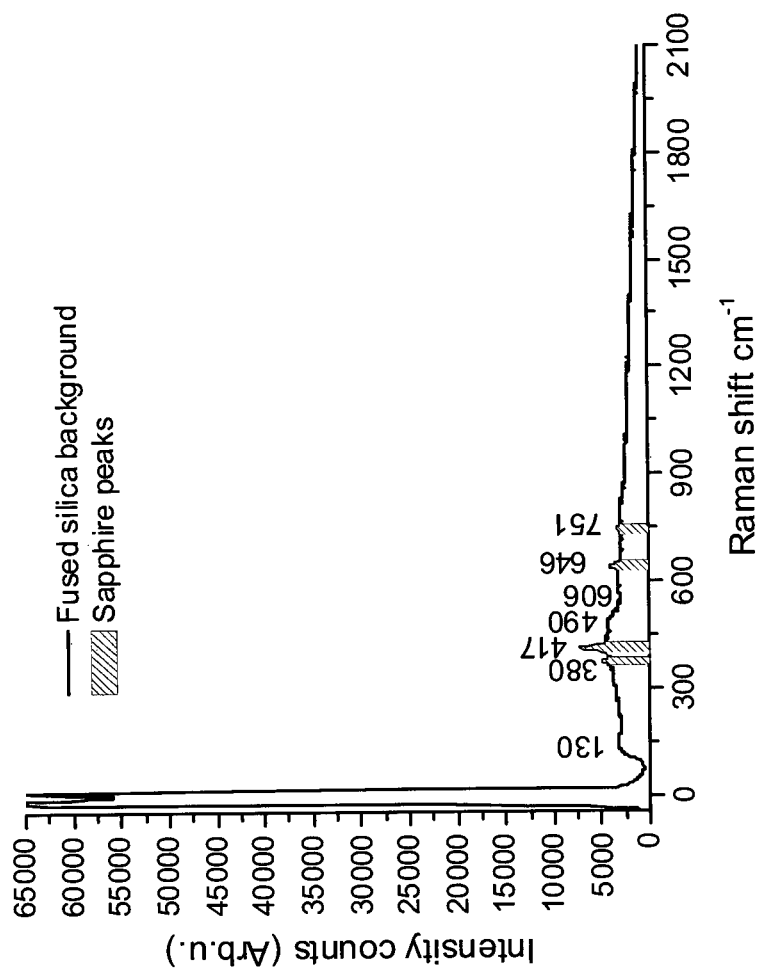
FIG. 11 is a graph showing background spectral peaks due to the fiber probe in a Raman spectrum.
Figure 12:
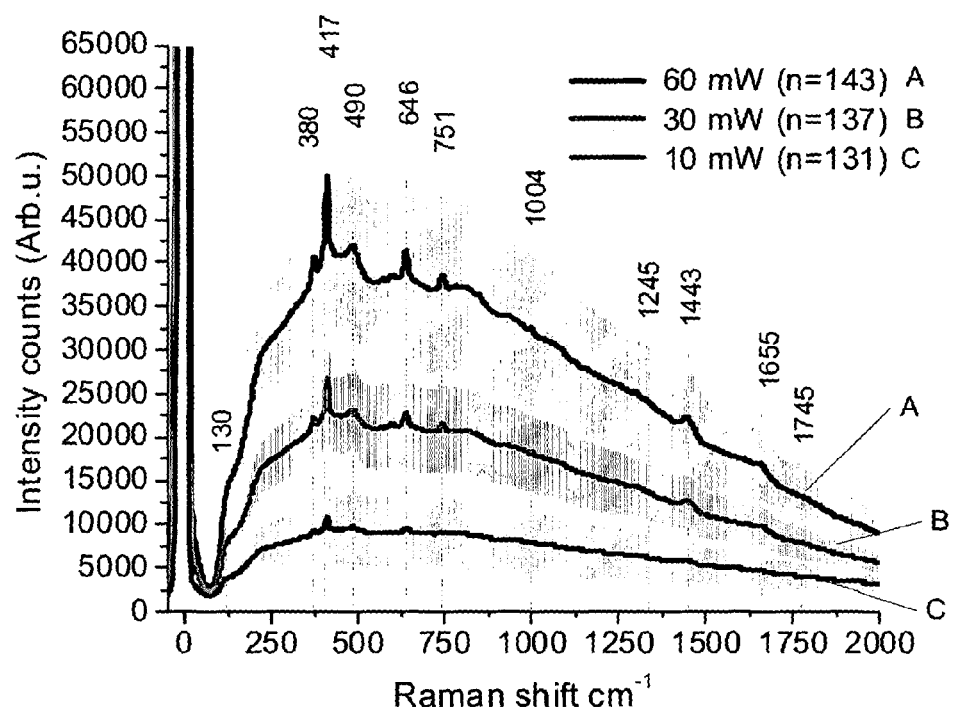
FIG. 12 is a graph showing variation of the Raman spectra with excitation laser power.

FIG. 11 is a graph showing a background spectrum from a fibre probe, i.e. in the absence of a tissue signal. Peaks corresponding to Raman scattering or fluorescence within the silica of the fibre and peaks corresponding to the sapphire of the distal ball lens are apparent. FIG. 12 shows a graph of Raman spectra received from in vivo tissue with different levels of transmitted power. The peaks from FIG. 11 are apparent in the different lines of FIG. 12, but it will be apparent that the relative heights of the peaks and the continuum background vary with the transmitted power.

Figure 13A:
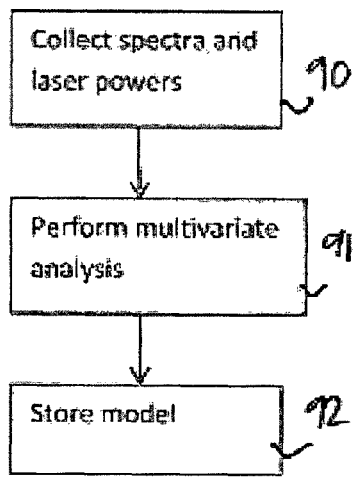
FIG. 13a is a flow chart illustrating a method of generating a model for estimating laser power.
Figure 13B:
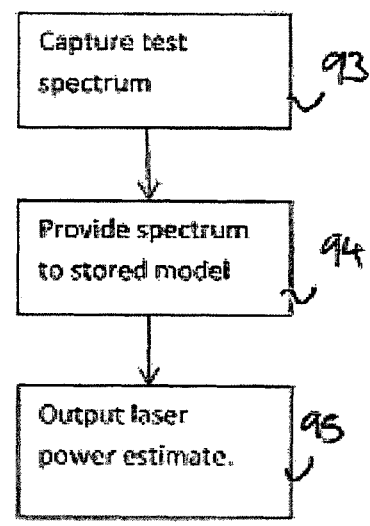
FIG. 13b is a flow chart illustrating a method of estimating laser power.

Advantageously, it has been found that the spectral characteristics of the fibre probe and sapphire ball lens in captured Raman spectra can be used as internal reference to derive the transmitted laser power without requiring the provision of any additional components in the optical train. As shown in the method of FIG. 13A, at step 90, a suitably large number of spectra, in the present example 352, are collected and the transmitted laser power measured. At step 91, a suitable multi-variate statistical analysis is performed, in the present example partial least squares ("PLS") regression. PLS regression reduces the dimension of spectral data to a number of latent variables ("LV"). In this case, the variance between the spectral variation and the dependent variable, the laser power, is maximised so that the latent variables give a higher weight to spectral peaks that correlate well with the laser power. By selecting an appropriate number of latent variables, a model of the laser power as a function of the spectral characteristics can be derived, and is stored as shown at step 92. Accordingly, in operation as shown in FIG. 13b at step 93 a test spectrum is captured, for example from an in vivo subject or otherwise, and at step 94 the spectral values are provided to the stored model. At step 95, the laser power is derived and displayed to the operator, for example on the personal computer 35.

Figure 14A:
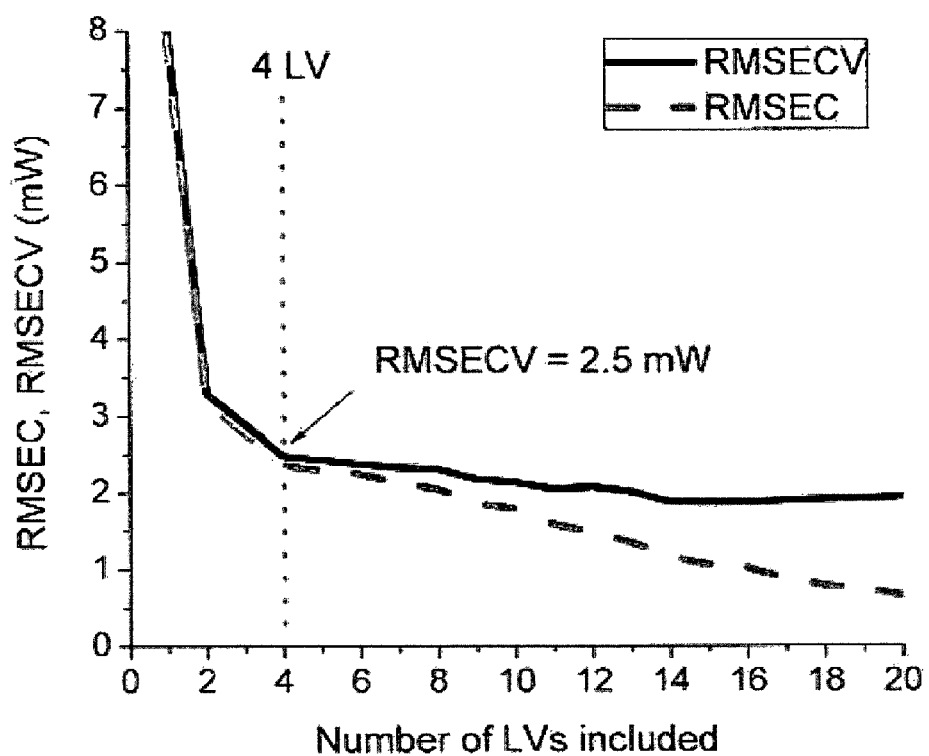
FIG. 14a is a graph showing the root mean square error for any number of included latent variables.
Figure 14B:
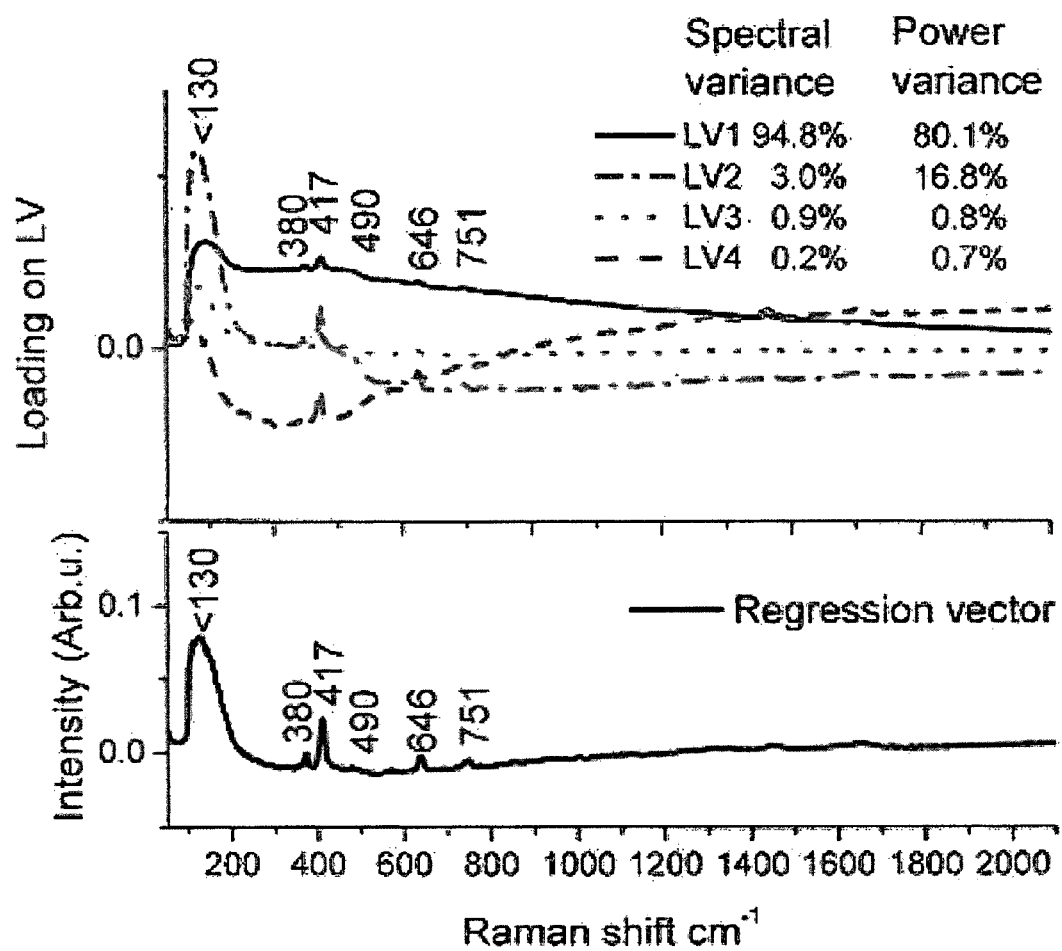
FIG. 14b shows the loading and regression factor for the latent variables of the method of FIG. 10.
Figure 15:
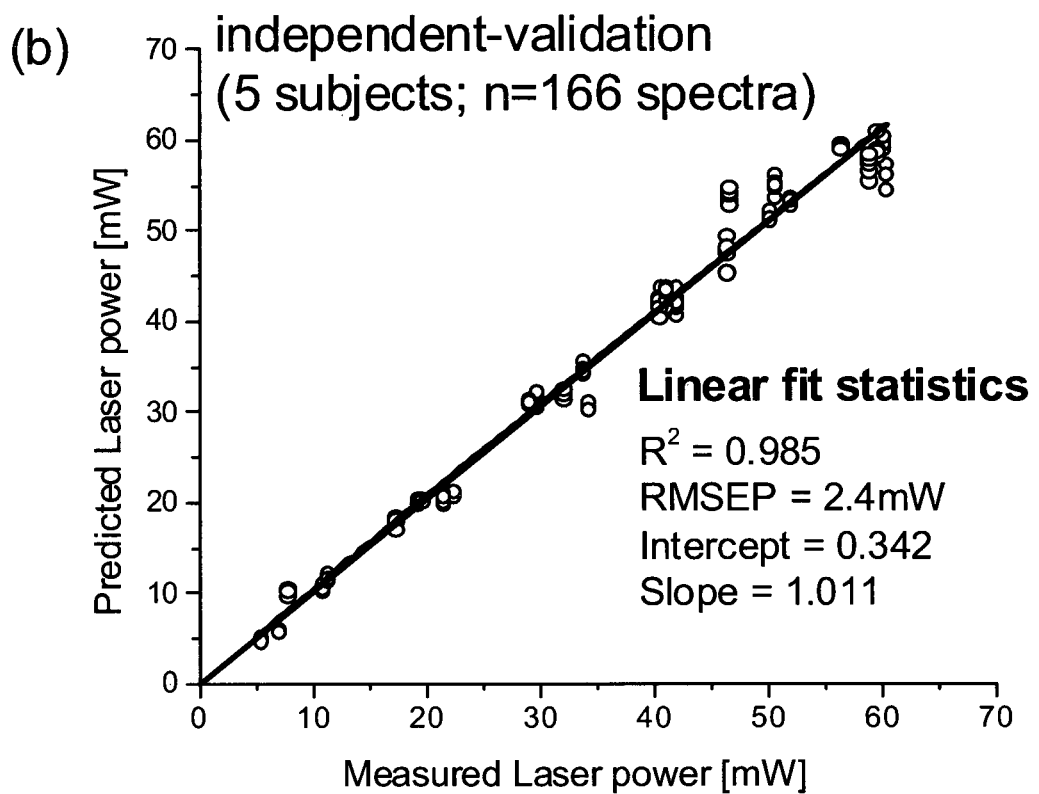
FIG. 15 is a graph showing measured laser power against predicted laser power in in vivo test subjects.

In the present example, a graph of the number of latent variables included against the root mean square error is shown in FIG. 14a, and four variables are selected as giving the best balance between error and complexity. The relative loading of the four latent variables and the regression vector are shown in FIG. 14b. In FIG. 15 example data from real-time measurements of 166 spectra in five subjects are shown, with the measured laser power plotted against the power estimated by the model. It will be apparent that the substantially linear fit shows that the estimated power is a good indicator of the power actually delivered.

Iterative Background Subtraction

Figure 16:
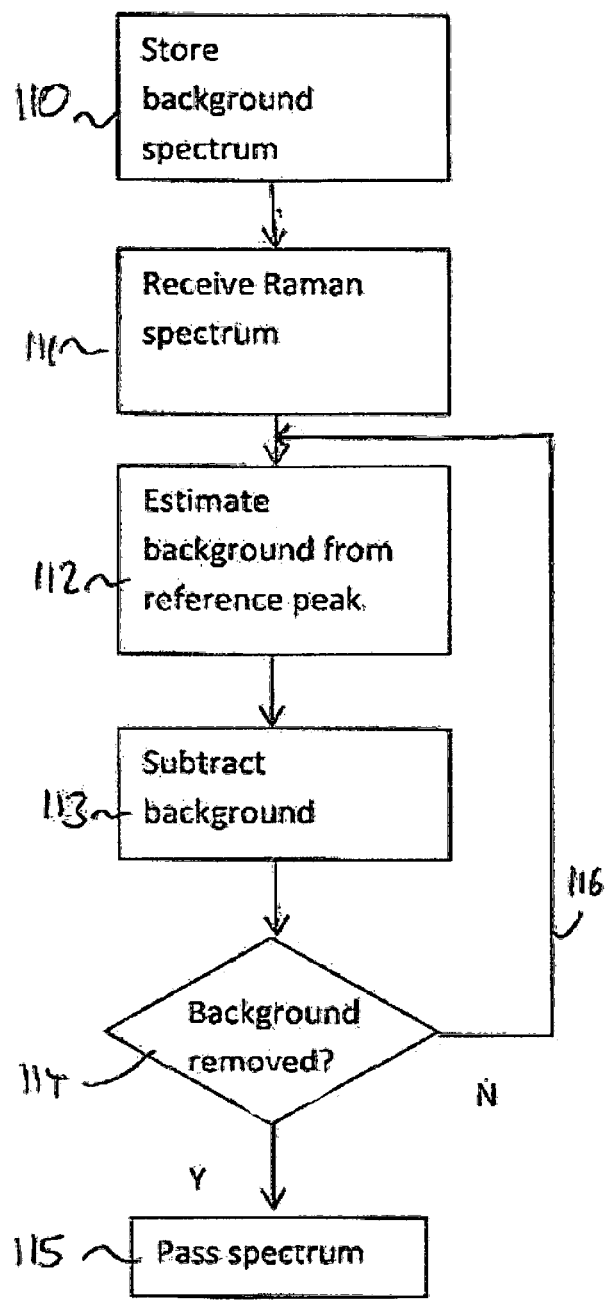
FIG. 16 is a flow chart showing a method of subtracting a probe background signal.
Figure 17:
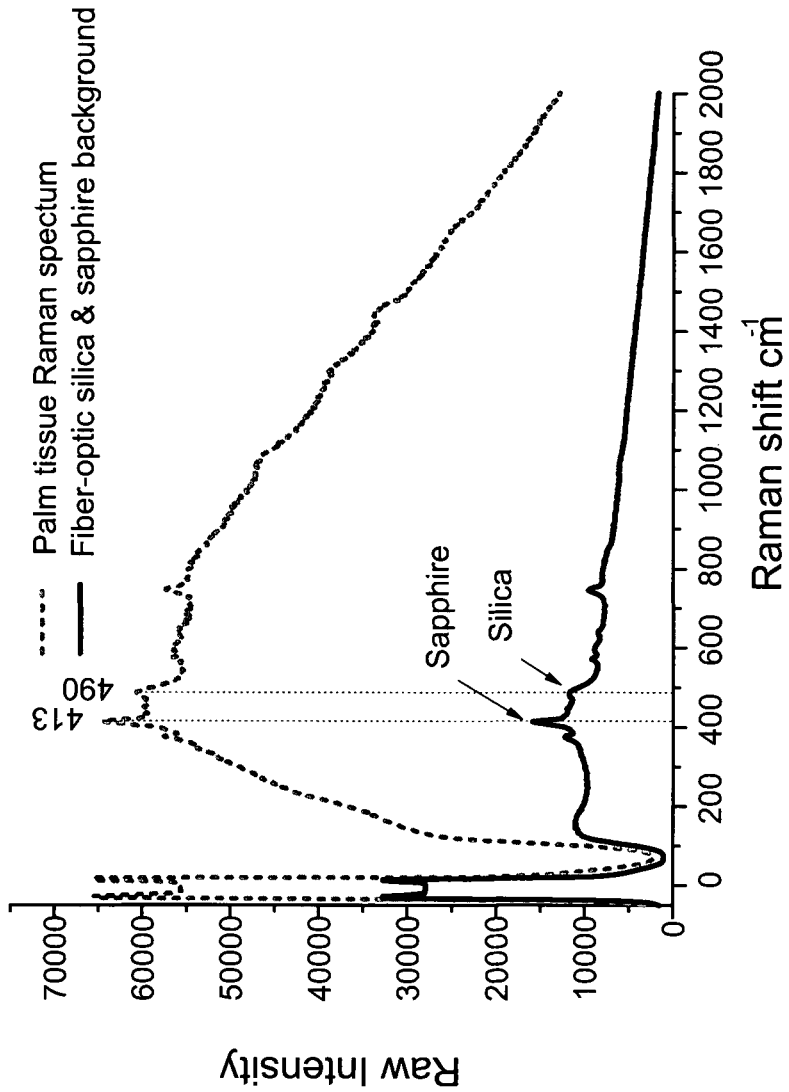
FIG. 17 is a graph showing a spectrum received from a palm and the fibre-optical silica and sapphire background.
Figure 18:
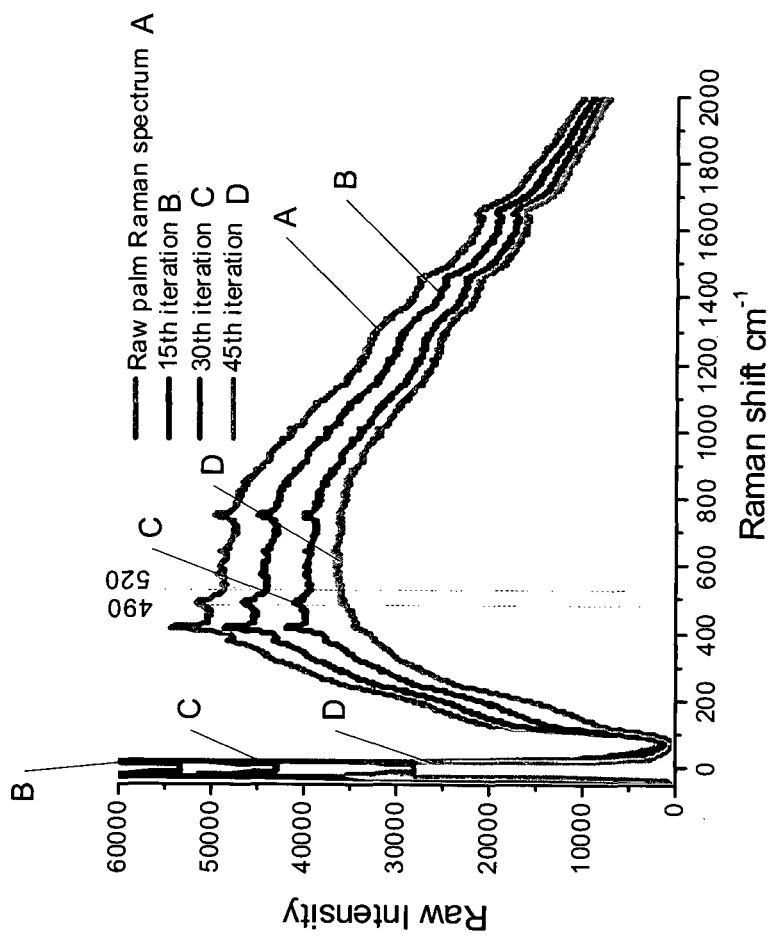
FIG. 18 is a graph comparing the Raman spectrum of FIG. 16 and the spectrum after background removal.

A method of subtracting the background Raman spectrum resulting from fluorescence, Raman scattering in the silica of the probe and the sapphire of the lens is shown with reference to FIGS. 16 to 18 This background signal is unique to each specific fiber probe. It is desirable to remove the background from the tissue Raman spectra without over- or under-subtracting the background.

As shown at step 110 in FIG. 16, the background spectrum is captured and stored, for example by transmitting light from the laser source through the probe in the absence of a target. At step 111, the Raman spectrum from a test subject is received, for example from tissue. At step 112, the amount of fiber background signal in the test subject Raman spectrum is estimated using the intensity of one or more distinct reference peaks. In the present example, the peaks may be due to silica and/or sapphire (e.g., 417 or 490 cm$^{-1}$). Using the estimated amount of background signal, the stored background signal may be multiplied by a suitable, possibly wavelength-dependent, correction factor and subtracted from the test spectrum (step 113).

At step 114, the spectrum is checked for the presence of remaining background. If the background has been fully removed, (i.e., when the silica and sapphire signal contributes negligible to the tissue Raman spectrum), the spectrum is passed for output or further analysis as shown at step 115. If a background signal is still present, then steps 112 to 114 are repeated as shown by arrow 116.

The method need not be limited to single silica/sapphire peaks. Multivariate analysis (e.g., partial least squares and curve resolution methods etc.) can also be used for this purpose.

By way of example, FIG. 17 is a graph showing a Raman spectrum received from palm tissue and a background spectrum from the probe. The peaks from fluorescence, Raman scattering in the silica of the probe and the sapphire of the lens are apparent, superposed on the Raman spectrum from the palm. This background signal is unique to each specific fiber probe As shown in FIG. 18, after the iterative process of FIG. 16 has been performed, the smooth Raman spectra are shown without the distinctive peaks of the background signal but retaining the essential Raman spectroscopic information required.

Combined System

Figure 19:
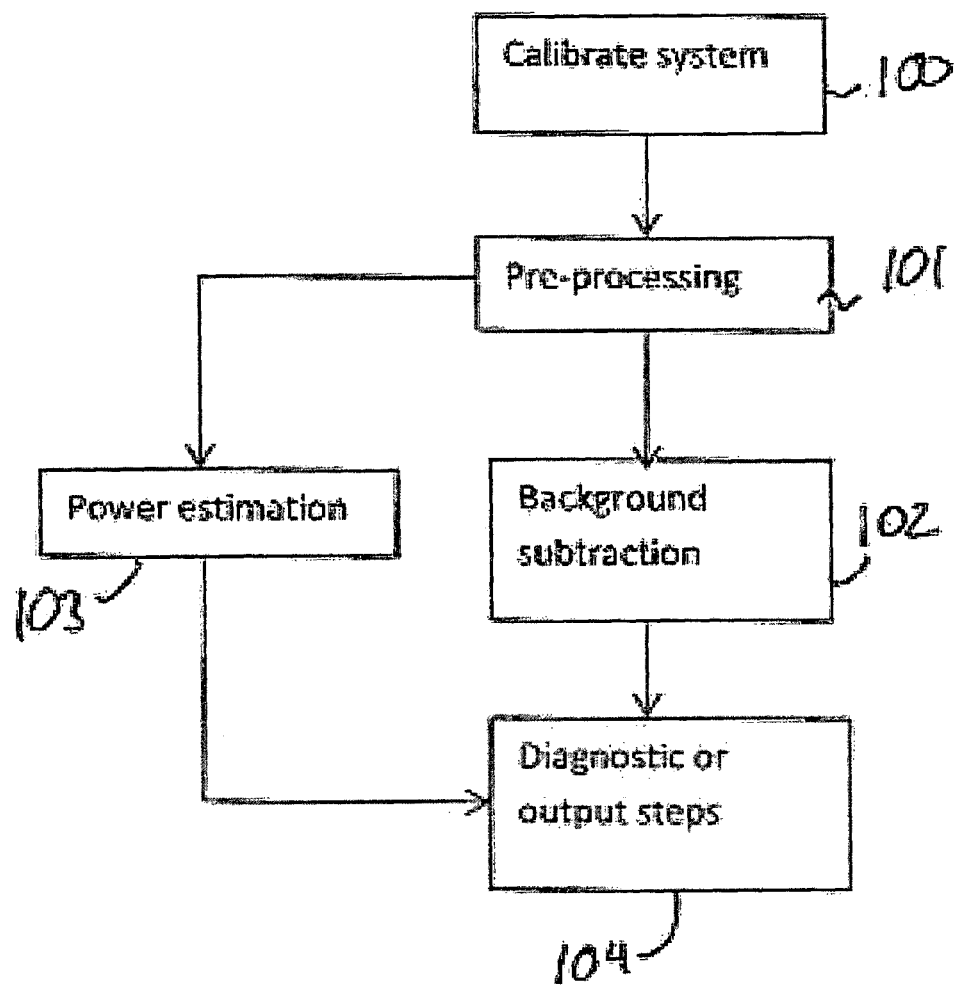
FIG. 19 is a flow chart showing a combination of the methods.

The various disclosed methods can be used together. One embodiment of such a combination is illustrated in FIG. 19. At step 100 the calibration method can be performed such that the system transfer function is known in accordance with a master or primary system 50 and subsequent spectra can be appropriately corrected. At step 101, pre-processing of the signal can be performed, including smoothing and tissue background subtraction. At step 103 power monitoring can be performed on the spectrum as discussed above and, in parallel, at step 102 probe background subtraction can be performed. As shown at step 104, the information of steps 102 and 103 is provided to a suitable program on the personal computer 35 to perform other diagnostic or output steps.

In combining the disclosed calibration method with a diagnostic method, instrument-independent fiber optic Raman spectroscopy is possible for quantitative tissue analysis and characterization. This allows for comparison of spectra taken by different instruments and also spectra taken with the same instrument but different probes. This is important for diagnosis in that it allows use of spectra taken on different machines or with different probes to be used for comparison. This is important for increasing accuracy of diagnosis.

Real-Time Cancer Diagnostics

An on-line biomedical spectroscopy (i.e., reflectance, fluorescence and Raman spectroscopy) system and method realizes real-time cancer diagnostics at clinical endoscopy and can interface with clinicians using auditory feedback as well as graphical display of the outcome of probabilistic diagnostic algorithms with the predicted pathology. Taking Raman endoscopy in the gastric as an example (FIG. 22A); the method is able to predict several pathologies: normal, intestinal metaplasia, dysplasia and neoplasia. This on-line diagnostic method provides information to the clinician in real-time of tissue pathology that can be used for decision-making such as biopsy guidance or tumor eradication. The system, including a GUI, is optimized for rapid data processing allowing real-time diagnostics (<0.1 s) for example for clinical endoscopy In order to address inter-anatomical and inter-organ spectral variances the online framework implements organ specific diagnostic models and switches among the spectral databases of different organs (e.g., esophagus, gastric, colon, cervix, bladder, lung, nasopharynx, larynx, and the oral cavity (hard palate, soft palate, buccal, inner lip, ventral and the tongue)). Thus, the disclosed Raman platform is a universal diagnostic tool for cancer diagnostics at endoscopy.

Figure 20:
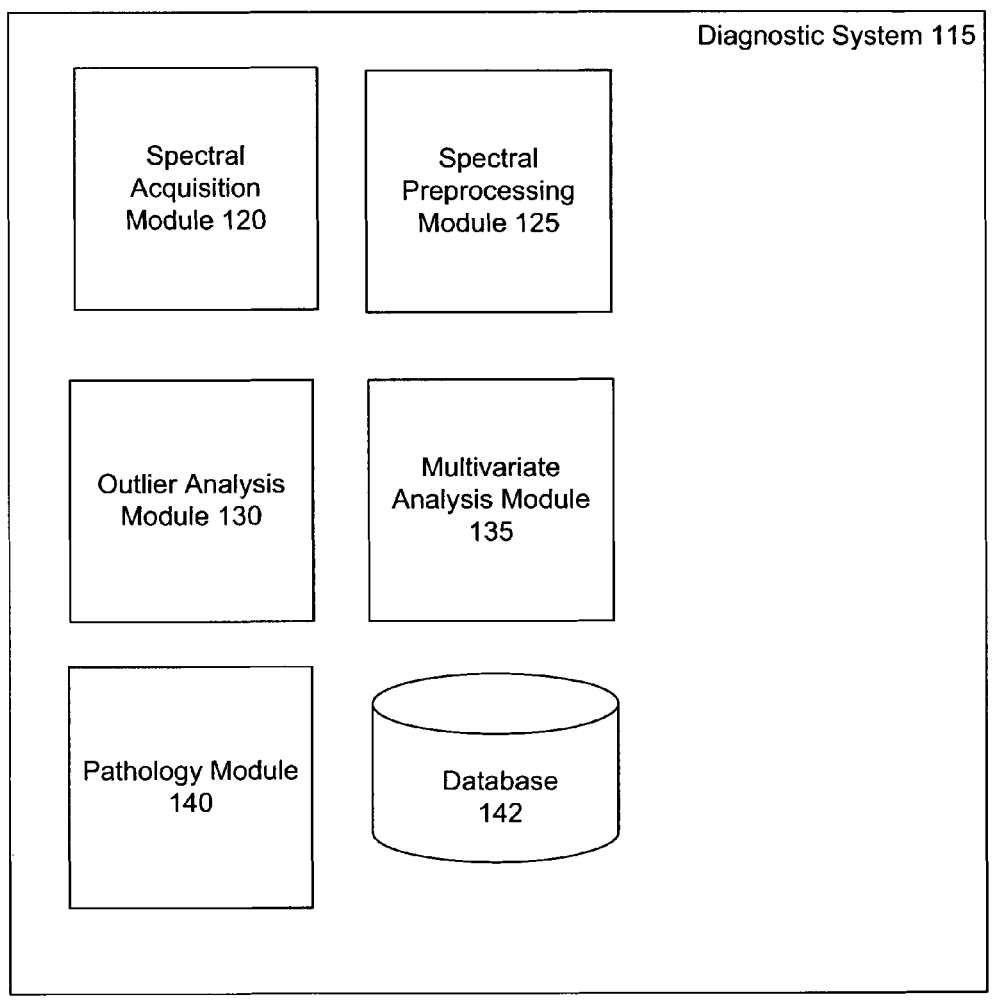
FIG. 20 is an architecture diagram for the system for spectral acquisition and processing flow for real-time cancer diagnostics according to one embodiment.

FIG. 20 is an architecture diagram for a diagnostic system 115 for spectral acquisition and processing flow for real-time cancer diagnostics according to one embodiment. The diagnostic system 115 may be implemented on the personal computer 35. The diagnostic system 115 comprises a spectral acquisition module 120, a spectral preprocessing module 125, an outlier analysis module 130, a multivariate analysis module 135, a pathology module 140 and a database 142. For simplicity only one spectral acquisition module 120, spectral preprocessing module 125, outlier analysis module 130, multivariate analysis module 135, pathology module 140 and database 142 are shown but in practice many of each may be in operation.

Figure 21:
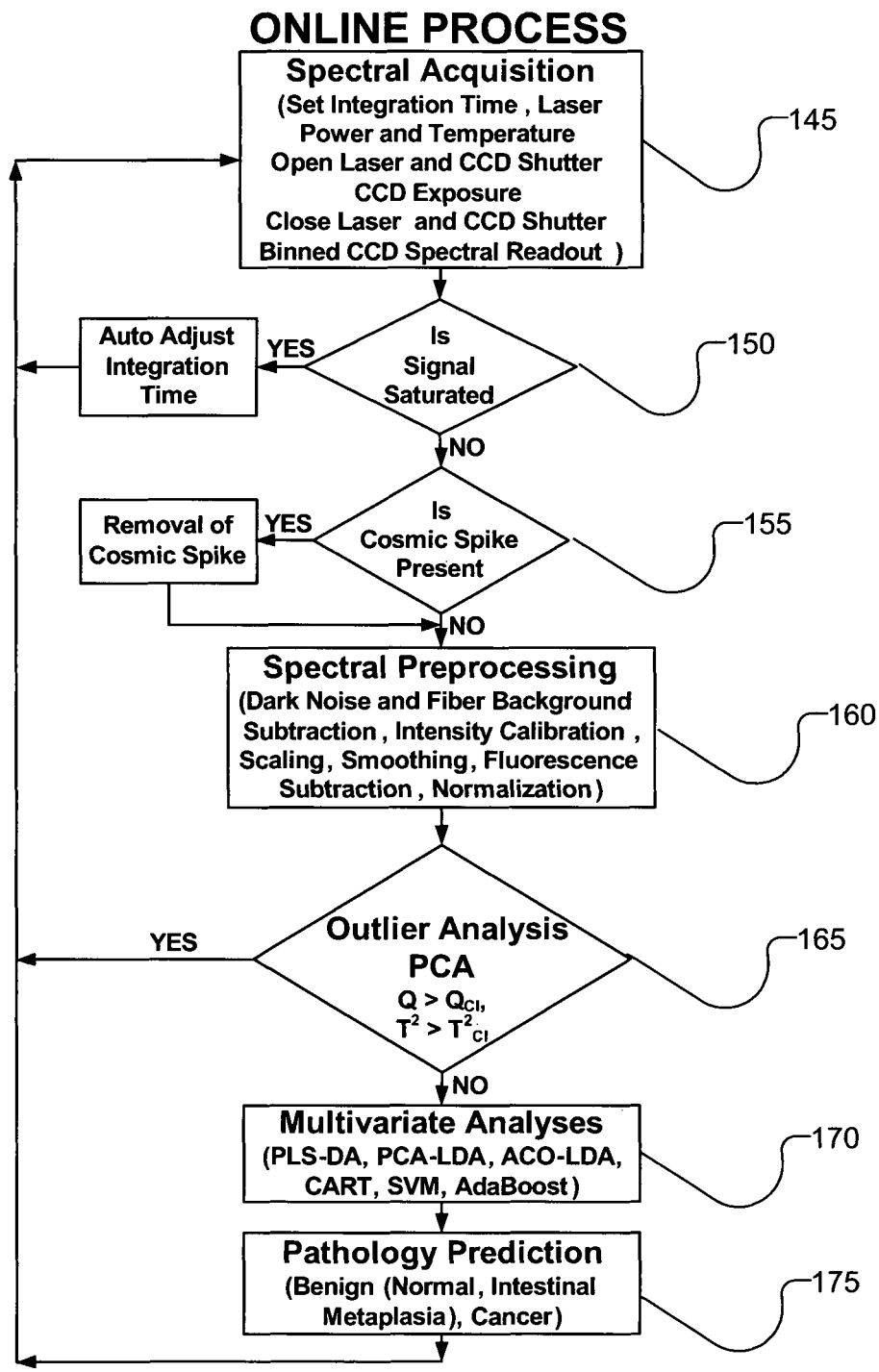
FIG. 21 is a flow chart illustrating a schematic of the spectral acquisition and processing flow for real-time cancer diagnostics according to one embodiment.
Figure 22A:
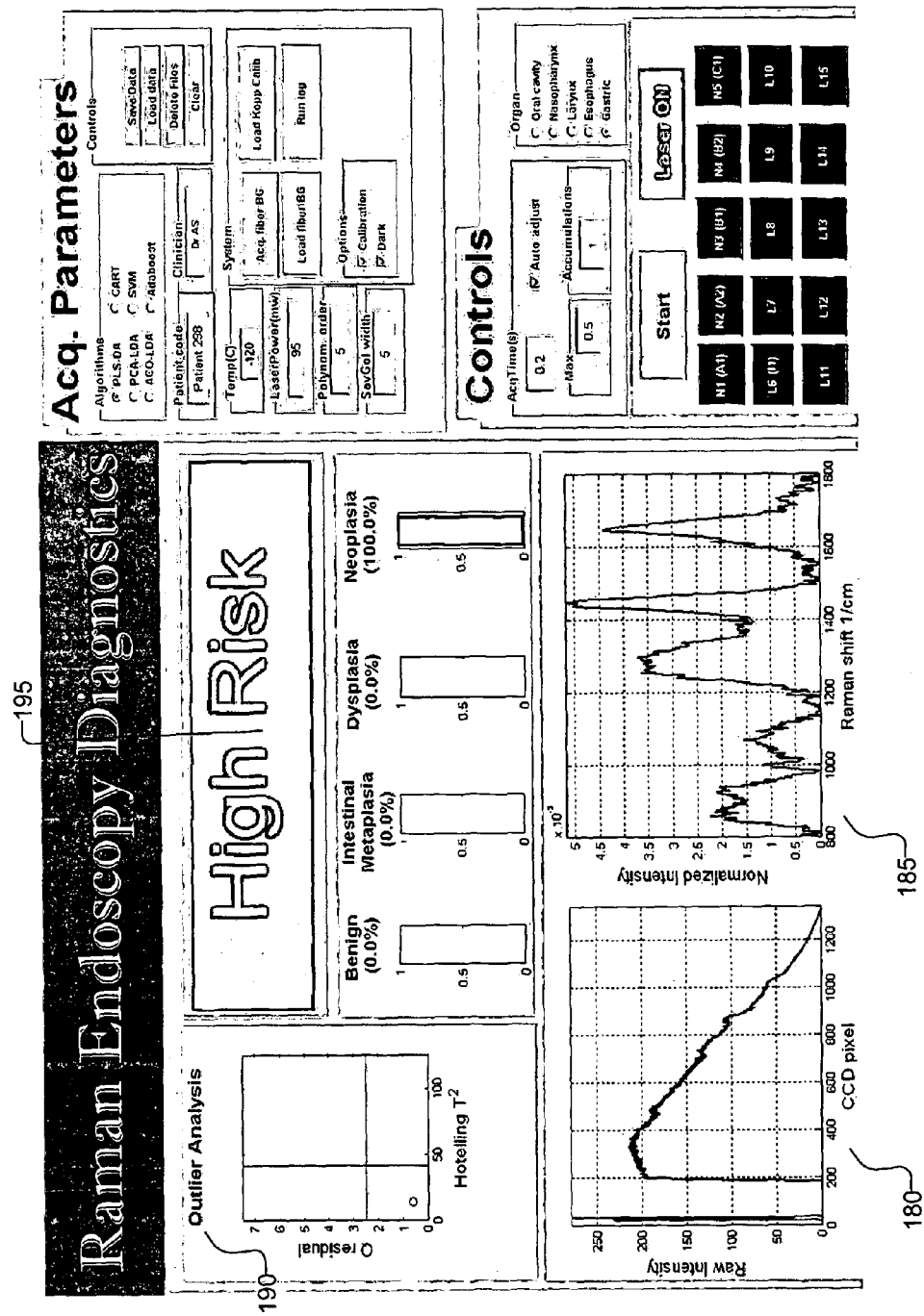
FIGS. 22A and B are a graphical user interfaces (GUI) for using the system for real-time cancer diagnosis according to two embodiment.

Referring to FIGS. 20-22, in step 145, the spectral acquisition module 120 electronically synchronizes the laser excitation source with the CCD and stores the binned read-out from the CCD in the database 142 for further processing. The spectral acquisition module further automatically adjusts the exposure time and accumulation of spectra by scaling to within ~85% of the total photon counts based on preceding tissue measurements, whereas an upper limit of 0.5 sec is set to realize clinically acceptable conditions. The accumulation of multiple spectra and automatic adjustment of exposure time provides a rapid and straightforward methodology to prevent signal saturation and to obtain high signal to noise ratio for endoscopic applications. If the spectral signal saturates, the method initiates a new data acquisition with reduced integration time to prevent saturation. After the spectral acquisition, the method identifies and eliminates cosmic rays (e.g., using the first derivative of the spectra with a 95% confidence interval (CI) over the whole spectral range set as a maximum threshold). The identified cosmic rays are removed by linear interpolation. The short spectral acquisition time frame is especially useful for endoscopic applications. The GUI illustrated at FIG. 22A illustrates the spectrum acquisition at 180.

For other applications, the spectral acquisition framework could also be used for external or internal surgical interventions or to assess tissue types during surgery. The real-time capability allows on-the-spot diagnosis and could therefore be used to guide excisional margins for tumor resection. It is critical that the diagnostic information can be given online (i.e., <0.5 sec) to aid in medical decision-making. For skin measurements, there are less stringent demands to the measurement time because skin spectra are acquired under more controllable experimental settings with possibility of longer exposure times. The online software architecture can also apply to other areas that require fast spectral measurements including fluorescence, reflectance spectroscopy or in different fields such as process analytical technology, food sciences, forensics, etc., whereby uninterrupted real-time screening is needed. In step 150, the spectral acquisition module 120 determines if the signal is saturated. If so, it initiates a new data acquisition with reduced integration time to prevent saturation. In step 155, the spectra acquisition module 120 identifies and eliminates cosmic rays (i.e., using the first derivative of the spectra with a 95% confidence interval (CI) over the whole spectral range set as a maximum threshold). In one embodiment identified cosmic rays are removed by linear interpolation. Cosmic rays can be removed by other methods, including multivariate analysis, smoothing, mean filtering, median filtering, Fourier transform, wavelets, etc.

In step 160, the spectral preprocessing module 125 scales the acquired spectra with integration time and laser power. A first-order Savitzky-Golay smoothing filter is further used to remove the noise in the intensity corrected spectra. A 5th order modified polynomial constrained to the lower bound of the smoothed spectra is then subtracted to resolve the tissue Raman spectrum alone. The Raman spectrum is finally normalized to the integrated area under the curve from 800 to 1800 cm$^{-1}$ to resolve the spectral line shapes and relative intensities, reducing probe handling variations at clinical endoscopy. The GUI (FIG. 22A) illustrates the normalized spectrum at 185. In some embodiments, the spectral preprocessing module 125 utilizes additional methods for preprocessing including, but not limited to, multiple scatter correction (MSC), FIR filtering, weighted baseline subtraction, noise reduction, mean centering, differentiation, etc.

In step 165, the outlier analysis module 130 detects outlier spectra using principal component (PCA) coupled with Hotelling's T$^2$ and Q-residual statistics. The GUI (FIG. 22A) illustrates the outlier analysis at 190. The implementation of outlier detection serves as a high-level model-specific feedback tool in the on-line framework using principal component (PCA) coupled with Hotelling's T$^2$ and Q-residual statistics. Hotelling's T$^2$ and Q-residuals are the two independent parameters providing information of within and outside the model fit. Using these parameters as indicators of spectrum quality (i.e., probe contact mode, confounding factors, white light interference etc.), auditory feedback is integrated into the online Raman diagnostic system facilitating real-time spectroscopic screening and probe handling advice for clinicians. The software system provides different sound feedback for different diagnostic outcomes. For instance, if the spectrum is an outlier, a certain sound will appear. If the spectrum is diagnostically classified "normal" a second distinct sound will appear. If spectrum is classified "precancer" or "cancer" a third or fourth sound will appear. The frequency of the sound could be proportional with the "posterior probability". This is very useful because it provides the endoscopist with the real-time guidance while receiving diagnostic information. Thus, the endoscopist does not need to pay attention to the Raman platform monitor, but will focus on the endoscopic operation procedures with the sound guidance. If the outlier analysis module determines that the acquired spectrum is an outlier, the diagnostic system 115 starts over at step 145.

If the spectra were verified for further analysis, they are fed to probabilistic models for in vivo cancer diagnostics. In step 170 the multivariate analysis module 135 applies probabilistic models for in vivo cancer diagnostics. The multivariate analysis module 135 switches among different pre-rendered models including partial least squares-discriminant analysis (PLS-DA), PCA-linear discriminant analysis (LDA), ant colony optimization (ACO)-LDA, classification and regression trees (CART), support vector machine (SVM), adaptive boosting (AdaBoost) etc. based on a spectral databases of large number of patients.

In step 175, the pathology module 140 implements organ specific diagnostic models that can switch among the spectral databases of different organs for probabilistic cancer diagnostics. In addition to the audio feedback, the GUI (FIG. 22A) provides the clinician the output from the pathology module 140 at 195.

Figure 22B:
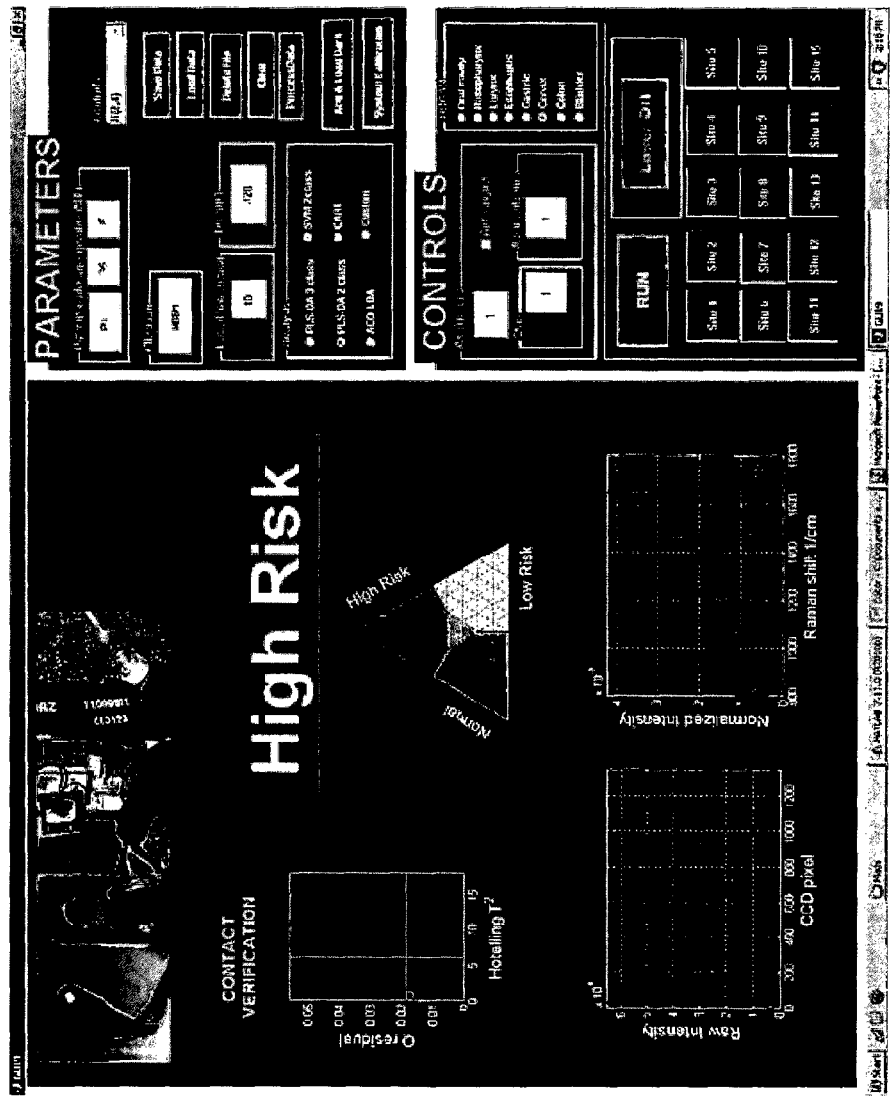

FIG. 22B provides the GUI according to a second embodiment.

The database 142 stores acquired spectra as well as the stored spectra used for diagnosis.

In some embodiments multiple spectra are taken and analyzed. For example between 5-15 are taken. Each is analyzed and if more than a threshold percentage provides the same outcome—cancer vs normal—that is the determined diagnosis. For example, if 10 spectra are taken and 7 or more provide the same answer, that is the diagnosis. If only 5 or 6 provide the same answer, the process is repeated.

EXAMPLE

An integrated Raman spectroscopy and trimodal wide-field imaging system used for real-time diagnostics comprises a spectrum stabilized 785 nm diode laser (maximum output: 300 mW, B&W TEK Inc., Newark, Del., USA) electronically synchronized with a USB 6501 digital I/O (National Instruments, Austin, Tex., USA), a transmissive imaging spectrograph (Holospec f/1.8, Kaiser Optical Systems, Ann Arbor, Mich., USA) equipped with a liquid nitrogen-cooled, NIR-optimized, back-illuminated and deep depletion charge-coupled device (CCD) camera (1340 400 pixels at 20×20 per pixel; Spec-10: 400BR/LN, Princeton Instruments, Trenton, N.J., USA), and a specially designed Raman endoscopic probe for both laser light delivery and in vivo tissue Raman signal collection. The 1.8 mm Raman endoscopic probe is composed of 32 collection fibers surrounding the central light delivery fiber with two stages of optical filtering incorporated at the proximal and distal ends of the probe for maximizing the collection of tissue Raman signals, while reducing the interference of Rayleigh scattered light, fiber fluorescence and silica Raman signals. The Raman probe can easily pass down to the instrument channel of medical endoscopes and be directed to suspicious tissue sites under the guidance of wide-field endoscopic imaging (WLR/AFI/NBI) modalities. The system acquires Raman spectra in the wavenumber range of 800-1800 cm$^{-1}$ from in vivo upper GI tissue within 0.5 s using the 785 nm excitation power of 1.5 W/cm$^2$ (spot size of 200 μm) with a spectral resolution of ~9 cm$^{-1}$.

Hardware components of the Raman system (e.g., laser power control, spectrometer, CCD shutter and camera read-out synchronization) were interfaced to the Matlab software through libraries for different spectrometers/cameras (e.g., PVCAM library (Princeton Instruments, Roper Scientific, Inc., Trenton, N.J., USA) and Omni Driver (Ocean Optics Inc., Dunedin, Fla., USA), etc.). The laser was electronically synchronized with the CCD shutter. The automatic adjustment of laser power, exposure time and accumulation of spectra were realized by scaling to within 85% of the total photon counts (e.g., 55,250 of 65,000 photons) based on preceding tissue Raman measurements, whereas an upper limit of 0.5 s was set to realize clinically acceptable conditions. The accumulation of multiple spectra and automatic adjustment of exposure time provides a rapid and straight-forward methodology to prevent CCD saturation and to obtain high signal to noise ratio (SNR) for endoscopic applications. The Raman-shift axis (wavelength) was calibrated using a mercury/argon calibration lamp (Ocean Optics Inc., Dunedin, Fla., USA). The spectral response correction for the wavelength-dependence of the system was conducted using a standard lamp (RS-10, EG&G Gamma Scientific, San Diego, Calif., USA). The reproducibility of the platform is continuously monitored with the laser frequency and Raman spectra of cyclohexane and acetaminophen as wavenumber standards. All the system performance measures including CCD temperature, integration time, laser power, CCD alignment are accordingly logged into a central database via SQL server.

Real-time preprocessing of Raman signals was realized with the rapid detection of cosmic rays using the first derivative with a 95% confidence interval (CI) over the whole spectral range set as a maximum threshold. Data points lying outside of a threshold were interpolated to $2^{nd}$ order. The spectra were further scaled with integration time and laser power. A first order, 5 point Savitzky-Golay smoothing filter was used to remove noise in the intensity corrected spectra, while a $5^{th}$ order modified polynomial constrained to the lower bound of the smoothed spectra was subtracted to resolve the tissue Raman spectrum alone. The Raman spectrum was normalized to the integrated area under the curve from 800 to 1800 $cm^{-1}$, enabling a better comparison of the spectral shapes and relative Raman band intensities among different tissue pathologies. The spectra were then locally mean-centered according to the specific database to remove common variations in the data. Following preprocessing, the Raman spectra were fed to a model-specific outlier analysis.

An outlier detection scheme was incorporated into biomedical spectroscopy as a high-level model-specific feedback tool in the on-line framework by using PCA coupled with Hotelling's $T^2$ and Q-residual statistics. PCA reduces the dimension of the Raman spectra by decomposing them into linear combinations of orthogonal components (principal components (PCs)), such that the spectral variations in the dataset are maximized. The PCA model of the data matrix X is defined by:

$$X = TP^T + E$$

where T and P represent scores and loadings, and E contains the residuals. The loadings correspond to the new rotated axis, whereas scores represent the data projection values. Accordingly, Hotelling's $T^2$ statistics is a measure of variance captured by the PCA model (sample to model distance) and is defined by:

$$T_{ik}^2 = t_{ik}(\lambda_k^{-1})t_{ik}^T$$

where $t_{ik}$ is PC scores for $i^{th}$ sample spectrum using component k, and $\lambda_k^{-1}\lambda_k^{-1}$ is the diagonal matrix of normalized eigenvalues of the covariance matrix for component k. Therefore, Hotelling's $T^2$ gives an indication of extreme values within the PCA model. On the other hand, Q-residuals is a measure of variance which is not captured by the PCA model (lack of model fit statistics) and is defined by $$Q_{ik} = \Sigma(x_i - t_{ik}P_k^T)^2$$

where $x_i$ is the sample spectrum, $Q_{ik}$ is the sum of squared reconstruction error for $i^{th}$ sample spectrum using component k and $P_k$ is the PC loadings. For both Hotelling's $T^2$ and Q-residuals, the normalized 99% CI was utilized as upper thresholds to intercept anomalous Raman spectra. Accordingly, the Hotelling's $T^2$ and Q-residuals are two independent parameters providing quantitative information about the model fit. Using these parameters as indicators of spectra quality (i.e., probe contact mode, confounding factors, white light interference etc.), auditory feedback has been integrated into the online Raman diagnostic system, facilitating real-time probe handling advice and spectroscopic screening for clinicians during clinical endoscopic procedures.

Subsequent to verification of tissue Raman spectra quality, those qualified Raman spectra were immediately fed to probabilistic models for on-line in vivo diagnostics and pathology prediction. The GUI can instantly switch among different models including partial least squares-discriminant analysis (PLS-DA), PCA-linear discriminant analysis (LDA), ant colony optimization (ACO)-LDA, classification and regression trees (CART), support vector machine (SVM), adaptive boosting (AdaBoost) etc. for prospective classification at clinical endoscopic procedures. As an example, probabilistic PLS-DA was employed for gastric cancer diagnosis. PLS-DA employs the fundamental principle of PCA but further rotates the components by maximizing the covariance between the spectral variation and group affinity to obtain the diagnostically relevant variations rather than the most prominent variations in the spectral dataset. The system supports binary classification, one-against-all and one-against-one multiclass (i.e., benign, dysplasia and cancer) probabilistic PLS-DA discriminatory analysis to predict the specific tissue pathologies.

Example 1

A total of 2748 in vivo gastric tissue spectra (2465 normal and 283 cancer) were acquired from the 305 patients recruited to construct the spectral database for developing diagnostic algorithms for gastric cancer diagnostics. Tissue histopathology serves as the gold standard for evaluation of the performance of Raman technique for in vivo tissue diagnosis and characterization.

Figure 23:
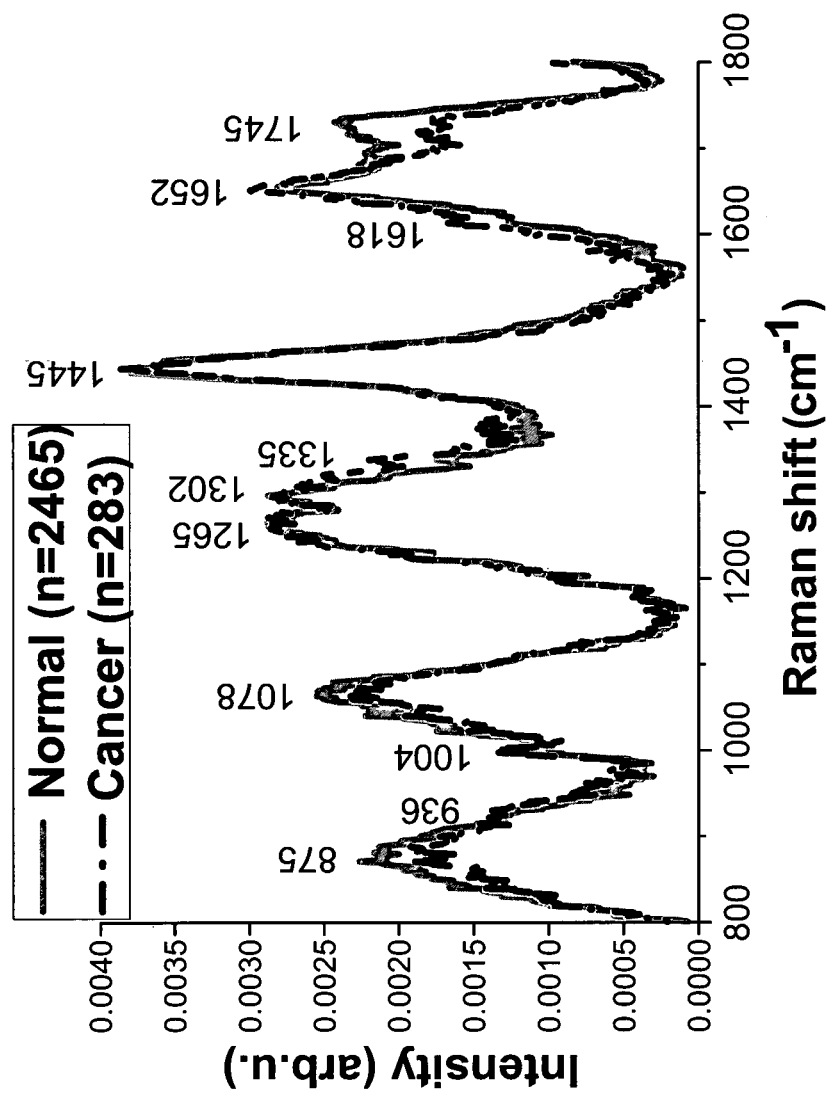
FIG. 23 is in vivo mean Raman spectra of normal (n=2465) and cancer (n=283) gastric tissue acquired from 305 gastric patients.

The stomach represents one of the most challenging organs presenting with many confounding factors (i.e., gastric juice, food debris, bleeding, exudates etc.) for spectroscopic diagnosis. The in vivo mean Raman spectra acquired from 305 gastric patients (normal (n 2465) and cancer (n=283)) for algorithms development are shown in FIG. 23. The Raman spectra of gastric tissue show the prominent Raman peaks at 875 $cm^{-1}$ (ν(C—C) of hydroxyproline), 936 $cm^{-1}$ (ν(C—C) of proteins), 1004 $cm^{-1}$ ($ν_s$(C—C) ring breathing of phenylalanine), 1078 $cm^{-1}$ (ν(C—C) of lipids), 1265 $cm^{-1}$ (amide III ν(C—N) and δ(N—H) of proteins), 1302 and 1335 $cm^{-1}$ (δ($CH_2$) deformation of proteins and lipids), 1445 $cm^{-1}$ (δ($CH_2$) of proteins and lipids), 1618 $cm^{-1}$ (ν(C═C) of porphyrins), 1652 $cm^{-1}$ (amide I ν(C═O) of proteins) and 1745 $cm^{-1}$ (ν(C═O) of lipids). Gastric tissue Raman spectra contain large contribution from triglyceride (i.e., major peaks at 1078, 1302, 1445, 1652, and 1745 $cm^{-1}$) that likely reflects the interrogation of subcutaneous fat in the gastric wall. The Raman spectra of gastric cancer reveal remarkable changes in the aforementioned Raman spectral properties (e.g., intensity, spectral shape, bandwidth and peak position), reconfirming our preceding in vivo Raman studies.

Figure 24:
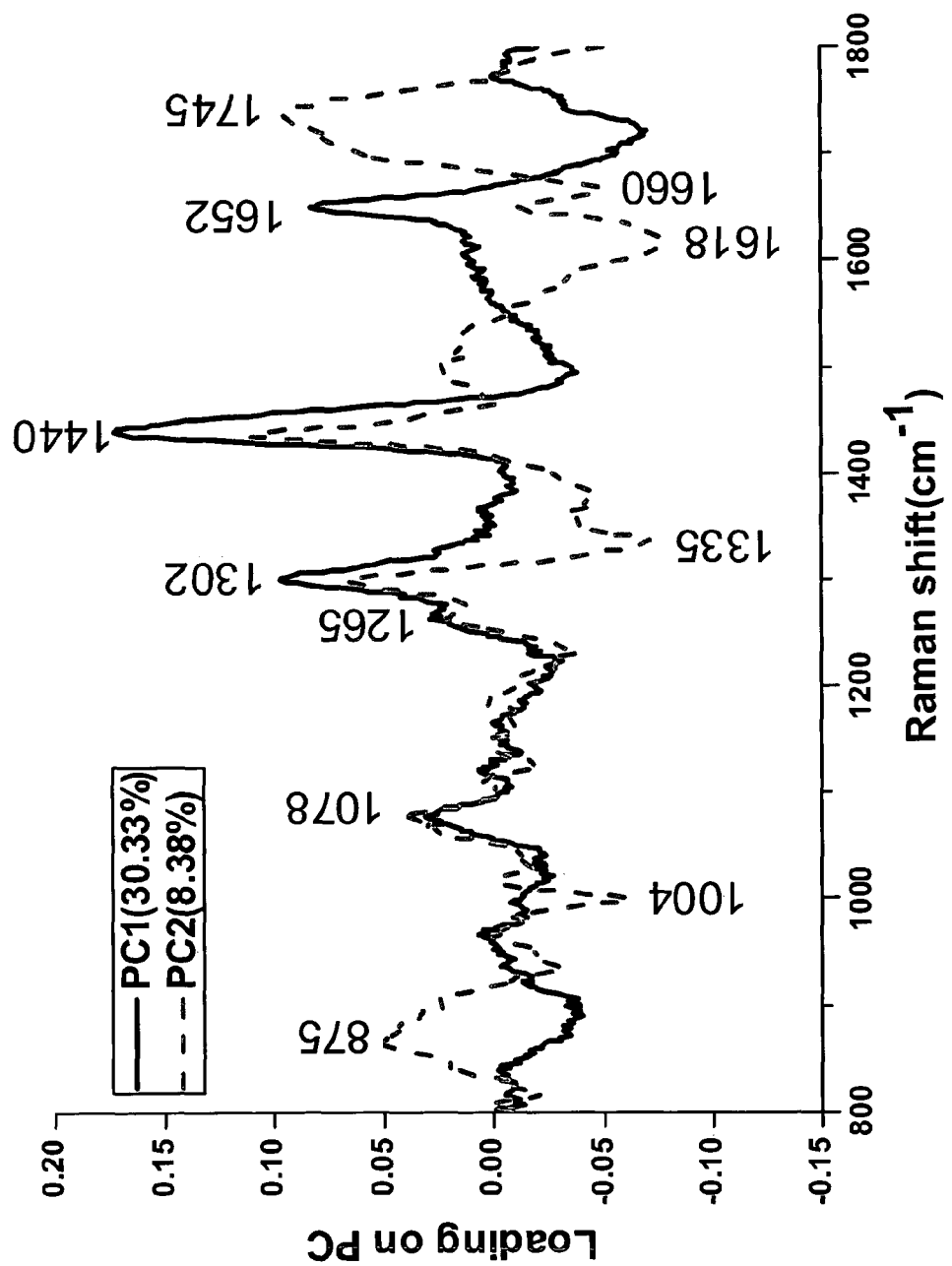
FIG. 24 illustrates principal component (PC) loadings calculated from a spectral training database.

The automatic outlier detection was realized for predictive on-line analysis using PCA with Hotelling's $T^2$ and Q-residuals statistics (99% CI). To make the online diagnostics efficient, a two-component PCA model was rendered that included the largest tissue spectral variations. These selected significant PCs (p<0.0001) accounted for maximum variance of 38.71% (PC1: 30.33%, PC2: 8.38%) of the total variability in the dataset (n=2748 Raman spectra), and the corresponding PC loadings are shown in FIG. 24.

Figure 25:
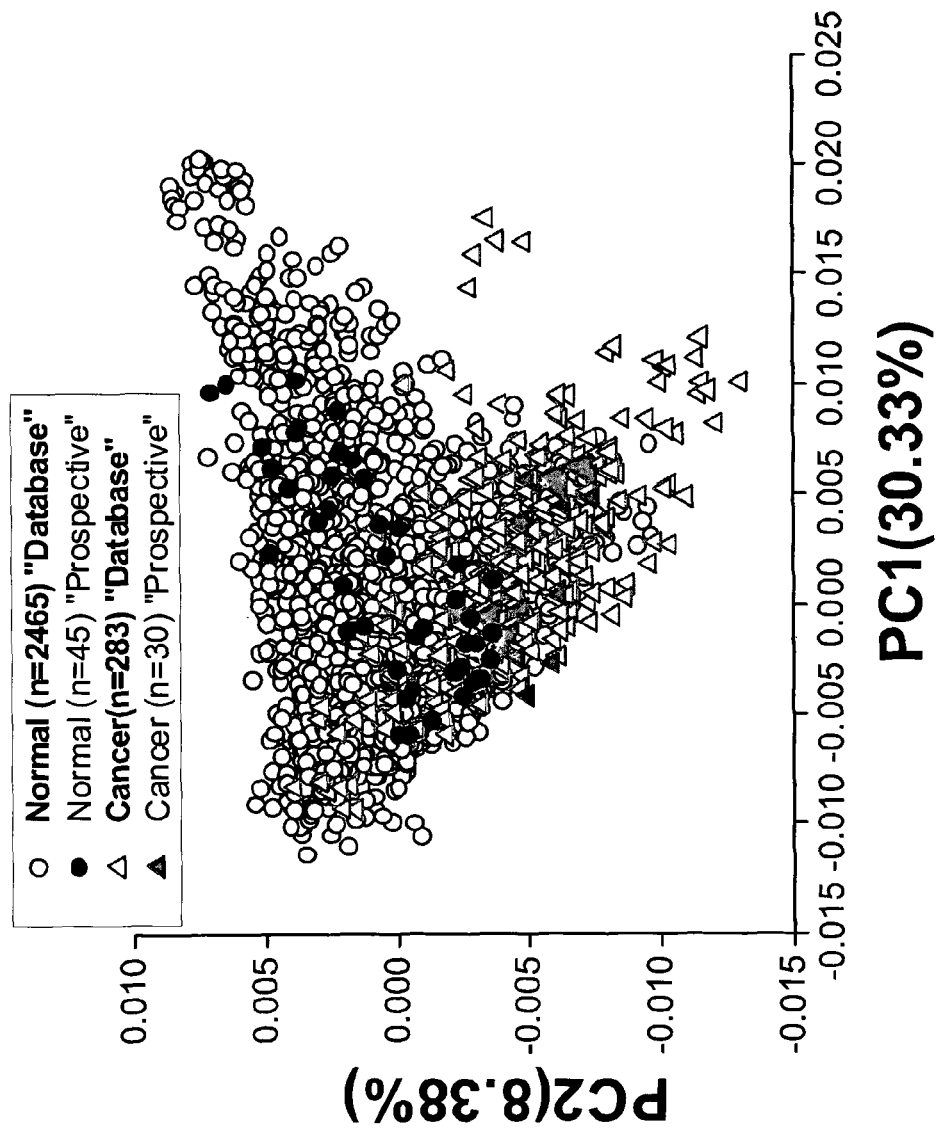
FIG. 25 are scatter plots of two diagnostically significant PC scores (PC1 vs PC2).

FIG. 25 shows the score scatter plots (i.e., PC1 vs. PC2) for the normal (n=2465) and cancer tissue spectra (n=283) exemplifying the capability of PC scores for separating the cancer spectra from normal. The 99% CI of Hotelling's T2 and Q residuals were accordingly calculated from the training dataset and fixed as a threshold for prospective on-line spectral validation. We then rendered probabilistic PLS-DA models for prediction of gastric cancer. The training database was randomly resampled multiple times (n=10) into learning (80%) and test (20%) sets. The generated PLS-DA models provided a predictive accuracy of 85.6% (95% CI: 82.9%-88.2%) (sensitivity of 80.5% (95% CI: 71.4%-89.6%) and specificity of 86.2% (95% CI: 83.6%-88.7%)) for gastric cancer diagnosis, retrospectively. We then further tested the outlier-detection as well as probabilistic PLS-DA in 10 prospective gastric patients. PC score scatter plots (i.e., PC1 vs. PC2) for the prospective normal (n=45) and cancer (n=30) tissue spectra are also shown in FIG. 25.

Figure 26:
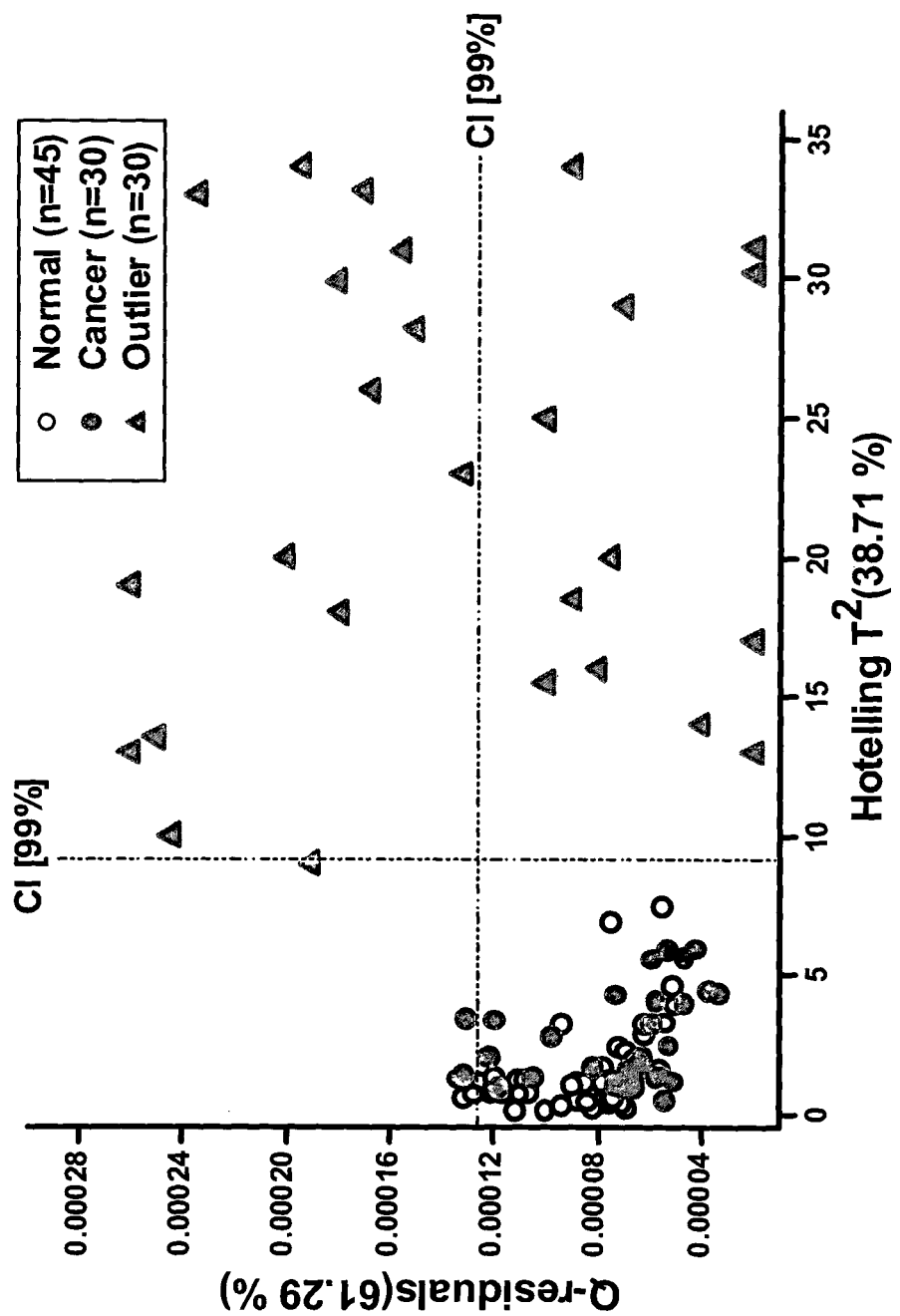
FIG. 26 demonstrates Hotelling's $T^2$ versus Q-residuals for 105 Raman spectra (45 normal, 30 cancer, 30 outlier) acquired from 10 prospective gastric samples.

FIG. 26 shows the prospective scatter plot of the Hotelling's $T^2$ (38.71%) and Q-residuals (61.29%) with the 99% CI boundaries for 105 spectra (45 normal, 30 cancer, 30 outlier) acquired from 10 prospective gastric samples. The dotted line represents the 99% confidence interval (CI) verifying whether the prospective Raman spectra are within the common tissue variations of the principal component analysis (PCA) model. It is observed that a large number of non-contact spectra lie outside the 99% CI and are therefore discarded in real-time without going for tissue diagnosis. The verified tissue Raman spectra largely fall inside the 99% CI of $T^2$ and Q residuals, demonstrating that this on-line data analysis provides a rapid and highly efficient means of real-time validation of biomedical tissue spectra.

Figure 27:
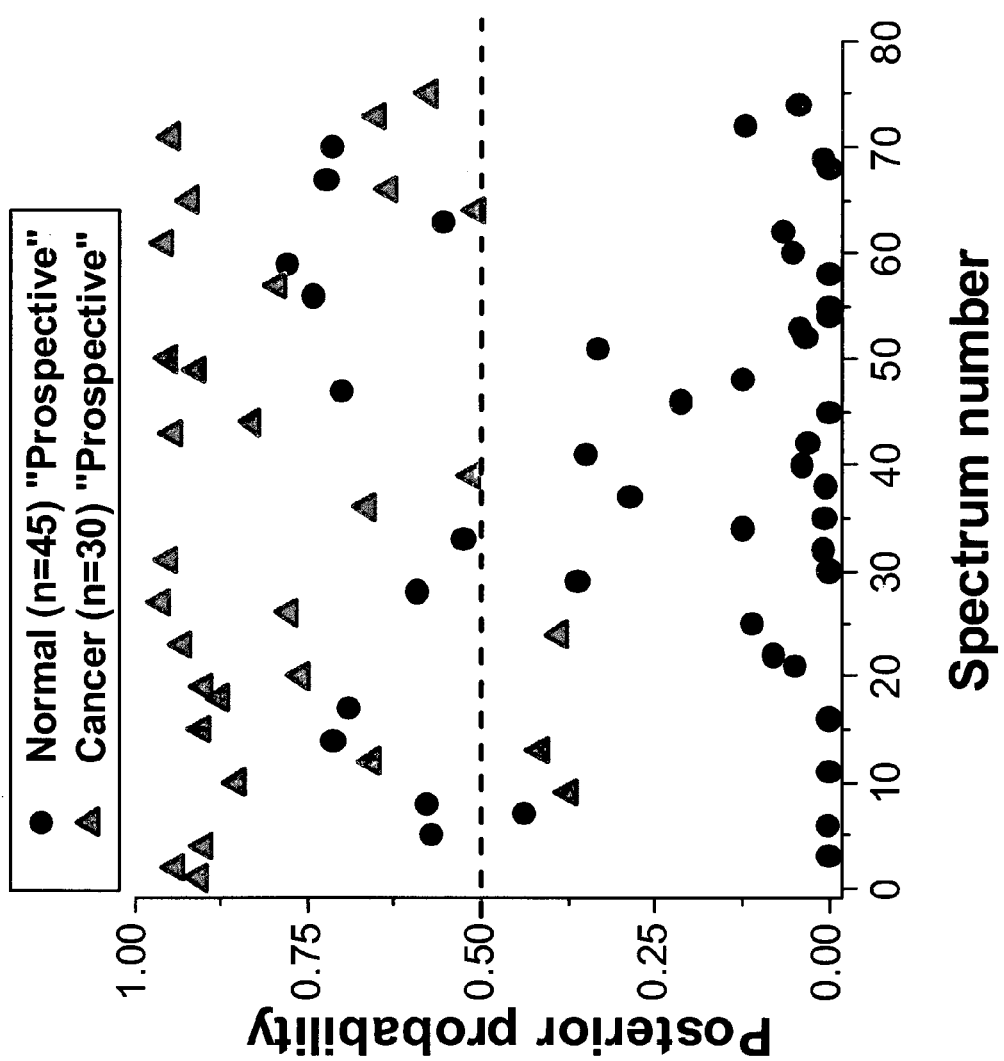
FIG. 27 is a scatter plot of the posterior probability values belonging to prospective normal (n=45) and cancer (n=30) gastric tissue based on PLS-DA modeling together with leave-one spectrum-out, cross-validation.

The prospectively acquired spectra verified by the on-line outlier analysis are further fed to probabilistic PLS-DA for instant disease prediction, achieving a diagnostic accuracy of 80.0% (60/75) for gastric cancer detection (FIG. 27), as confirmed by histopathological examination. The separate dotted line gives a diagnostic sensitivity of 90.0% (27/30) and specificity of 73.3% (33/45) for separating cancer from normal gastric tissue in vivo.

Figure 28:
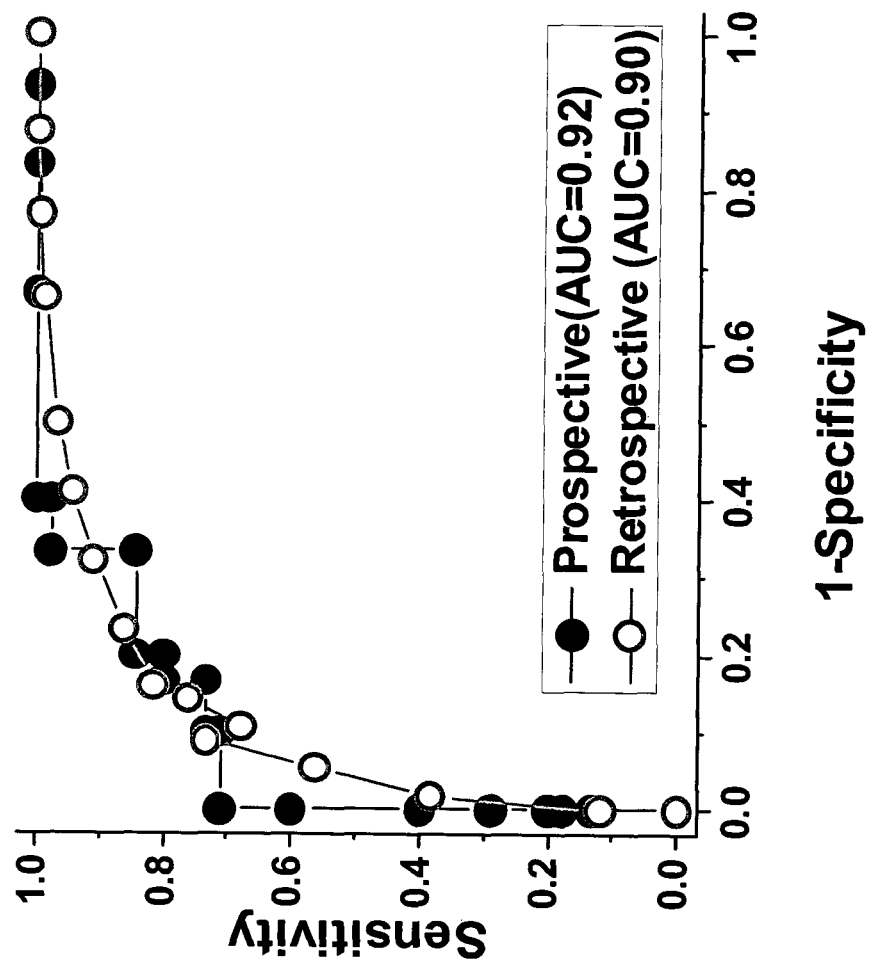
FIG. 28 illustrates receiver-operating characteristic (ROC) curves computed from the spectral database for retrospective prediction as well as ROC curve for prospective prediction of normal and cancer gastric tissue.

The receiver operating characteristic (ROC) curves were further generated to evaluate the group separations. FIG. 28 shows the mean of the ROC curves computed from each random splitting of the spectral database for retrospective prediction as well as the ROC calculated for the prospective dataset prediction. The integration areas under the ROC curves generated for the retrospective and prospective datasets are 0.90 and 0.92, respectively, illustrates the robustness of the PLS-DA algorithm for gastric cancer diagnosis in vivo.

The total processing time for all the aforementioned on-line data acquisition to tissue pathological prediction was 0.13 s. The processing time for each step of the flow chart in FIG. 21 are given in Table 1. Free-running optical diagnosis and processing time of <0.5 s can be achieved, which is critical for realizing real-time in vivo tissue diagnostics at endoscopy.

TABLE 1

Average processing time for on-line biomedical Raman spectroscopic framework on a personal computer 35 with a 64-bit I7 quad-core 4 GB memory.

| Analyses | Computational time (milliseconds) |
| --- | --- |
| Cosmic ray rejection | 0.5 |
| Laser response time | 10 |
| Preprocessing | 40 |
| Outlier detection | 10 |
| Probabilistic PLS-DA prediction | 70 |
| Total computation time | 100 to 130 |

Example 2

The Raman spectroscopy system comprises a spectrum stabilized 785 nm diode laser (maximum output: 300 mW, B&W TEK Inc., Newark, Del.), a transmissive imaging spectrograph (Holospec f/1.8, Kaiser Optical Systems Inc., Ann Arbor, Mich.) equipped with a liquid nitrogen-cooled, back-illuminated and deep depletion CCD camera (1340× 400 pixels at 20×20 μm per pixel; Spec-10: 400BR/LN, Princeton Instruments, Trenton, N.J.). The system also consists of a specially designed fused-silica fiber-optic Raman endoscopic probe (1.8 mm in outer diameter and 1.30 meters in length) that comprises 9×200 μm collection fibers (N.A.=0.22) surrounding the central light delivery fiber (200 μm in diameter, N.A.=0.22). A 1.0 mm sapphire ball lens (refractive index 1.76) is coupled to the fiber tip of the Raman probe for enhancing epithelial tissue Raman measurements. The system acquires Raman spectra over the range of 800-1800 cm-1 with spectral resolution of 9 cm-1. Each Raman spectrum in this study was measured with an integration time of 0.5 s under the 785 nm laser excitation. The rapid Raman spectroscopy technique was wavelength calibrated using an argon/mercury spectral lamp (AR-1 and HG-1, Ocean Optics Inc., Dunedin, Fla.). All wavelength-calibrated spectra were corrected for the intensity response of the system using a tungsten-halogen calibration lamp (RS-10, EG&G Gamma Scientific, San Diego, Calif.).

Using the system and method described in FIGS. 20-22 was used to control the Raman spectroscopy system for real-time data acquisition and analysis. The raw Raman spectra measured from in vivo tissue represent a combination of weak Raman signal, intense autofluorescence background, and noise. The raw spectra are preprocessed by a first-order Savitzky-Golay smoothing filter (window width of 3 pixels selected to match the spectral resolution) to reduce the spectral noise. In the fingerprint region (800-1800 cm$^{-1}$), a fifth-order polynomial was found to be optimal for fitting the autofluorescence background in the noise-smoothed spectrum, and this polynomial is then subtracted from the raw spectrum to yield the tissue Raman spectrum alone. All the aforementioned preprocessing is completed within 100 ms and the processed results can be displayed on the computer screen in real-time.

The PLS regression was employed as a multivariate method to extract characteristic internal reference background signals from the fiber-optic Raman probe. Briefly, PLS utilizes the fundamental principle of PCA but further rotates the components LVs by maximizing the covariance between the spectral variation and the dependent variable (e.g., laser excitation power), so that the LV loadings explain the relevant variations rather than the most prominent variations in the spectral dataset. Important spectral reference signals related to the laser excitation power were retained in the first few LVs. In this study, mean-centering was performed before modeling to reduce the complexity of the PLS regression model. The optimal complexity of the PLS regression model was determined through leave-one subject-out, cross-validation, and the performance of the PLS regression model was examined by calculating the coefficient of determination ($R^2$), root mean square error of calibration (RMSEC), root mean square error of cross validation (RMSECV) and root mean square error of prediction (RMSEP). Note that an optimal PLS model has a high $R^2$ but with a low RMSEC, RMSECV and RMSEP. The PLS regression model developed for resolving the reference signals in this study was also implemented as an on-line laser excitation power predictor in our real-time clinical Raman software and tested prospectively in an unbiased manner. Multivariate statistical analysis was conducted in the Matlab (Mathworks Inc., Natick, Mass.) programming environment.

A total of 30 normal healthy subjects (16 female and 14 males) were recruited for in vivo tissue Raman measurements in the oral cavity. Prior to in vivo tissue Raman spectroscopy measurements, all subjects underwent extensive mouthwash to reduce confounding factors (e.g. food debris, microbial coatings etc.). In vivo tissue Raman spectra (n=783) were collected of the inner lip of 25 subjects. For the 25 subjects, in vivo oral tissue Raman spectra (n=~5) were acquired at six power levels in the range of 5-65 mW (intervals of ~10 mW). Before each tissue Raman measurement, the laser excitation power level was measured at the distal tip of the fiber-optic probe using a power meter with a linearity of ±0.5% and accuracy of ±3% (range of 0.1 to 100 mW). Other confounding factors (e.g., probe pressure on the tissue surface, photobleaching, tissue optical properties and bending of the fiber optic probe) were not monitored purposely but incorporated into the PLS modeling for the robust extraction of reference signals in situ. After deployment of the developed PLS model in the on-line Raman acquisition framework, the prospective and independent validation of the internal reference signal for laser excitation power monitoring was performed on the 5 new subjects (n=166 spectra) in real-time.

To further validate the quantitative value of the internal reference method developed in this work, we also conducted a tissue phantom experiment. Tissue phantoms of various gelatin concentrations were prepared from bovine skin, Type-B gelatin (G9391, Sigma, USA). The gelatin was dissolved in predefined concentrations (20, 25, 30, 35, 40, 45, and 50% by weight) in distilled $H_2O$. The dissolved gelatin was heated to 50° C. for 1 hour in a water bath with continuous stirring. Subsequently, the molten gelatin was poured into a pre-chilled mold (4° C.) and stored for 2-3 hours to produce solid gelatin phantoms. Quantitative fiber-optic Raman spectroscopic analysis of the tissue phantoms was then performed. A total of n=133 Raman spectra were measured from the various tissue phantoms using the fiber-optic Raman probe with different laser powers. The laser excitation powers were changed in the range 10-60 mW and the measured spectra were normalized to laser excitation powers as predicted by the internal reference method.

FIG. 11 shows the background spectrum of a ball-lens fiber-optic Raman probe used when excited by a 785 nm diode laser. The distinct sapphire ($Al_2O_3$) Raman peaks originating from the distal ball lens can be found at 417 and 646 $cm^{-1}$ (phonon mode with $A_{1g}$ symmetry), and 380 and 751 $cm^{-1}$ ($E_g$ phonon mode). There are two dominant Raman components from the fused silica fiber as well as a relatively weak fiber fluorescence background. The sharp "defect peaks" of fused silica denoted as $D_1$ and $D_2$ at 490 and 606 $cm^{-1}$, have been assigned to breathing vibrations of oxygen atoms in four- and three-membered rings, respectively. The shoulder (~130 $cm^{-1}$) of an intense boson Raman band related to general feature of amorphous silica substances is also observed from the background spectrum of the fiber-optic Raman probe. The silica boson band is peaking near ~60 $cm^{-1}$ but only the shoulder was apparent due to the optical filterings of our Raman probe design. These characteristic background Raman peaks (shorter than fingerprint region (800-1800 $cm^{-1}$)) from the fiber-optic Raman probe itself could serve as internal reference signals for in vivo tissue Raman measurements.

Figure 29:
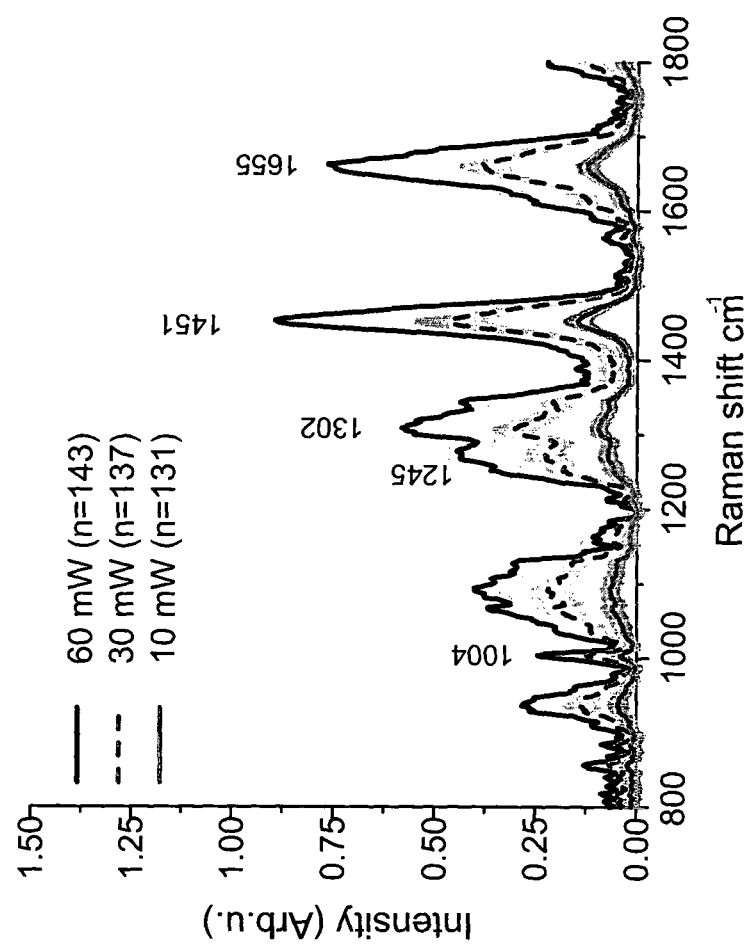
FIG. 29 illustrates the autofluorescence-subtracted and intensity calibrated mean in vivo tissue Raman spectra±1 SD of inner lip by using different 785-nm laser excitation powers (i.e., 10, 30 and 60 mW).

To develop the PLS regression model and resolve internal reference signals, we measured in vivo Raman spectra of 25 subjects in the oral cavity with the laser excitation power as an independent parameter. For each subject, in vivo tissue Raman spectra (n=~5) were acquired with different power levels in the range of 5-65 mW (intervals of ~10 mW). FIG. 12 shows an example of the mean in vivo raw Raman spectra±1 standard deviation (SD) measured from the inner lip using different laser excitation powers (e.g., 10, 30 and 60 mW). The weak tissue Raman signals superimposed on the varying broad autofluorescence background can be observed. FIG. 29 shows the calibrated background-free mean Raman spectra±1 SD. The in vivo Raman spectrum of the inner lip shows Raman peaks at around 853 $cm^{-1}$ ($v(C—C)$), 1004 $cm^{-1}$ ($v_s(C—C)$), 1245 $cm^{-1}$ (amide III $v(C—N)$ and $\delta(N—H)$ of proteins), 1302 $cm^{-1}$ ($CH_3CH_2$ twisting and wagging), 1443 $cm^{-1}$ ($\delta(CH_2)$ deformation), 1655 $cm^{-1}$ (amide I $v(C=O)$ of proteins) and 1745 $cm^{-1}$ $v(C=O)$). On the other hand, the raw in vivo tissue Raman spectra (FIG. 12) also contained the prominent fused silica and sapphire Raman peaks from the fiber-optic Raman probe, that is: 380, 417, 490, 606, 646, and 751 $cm^{-1}$.

Figure 30:
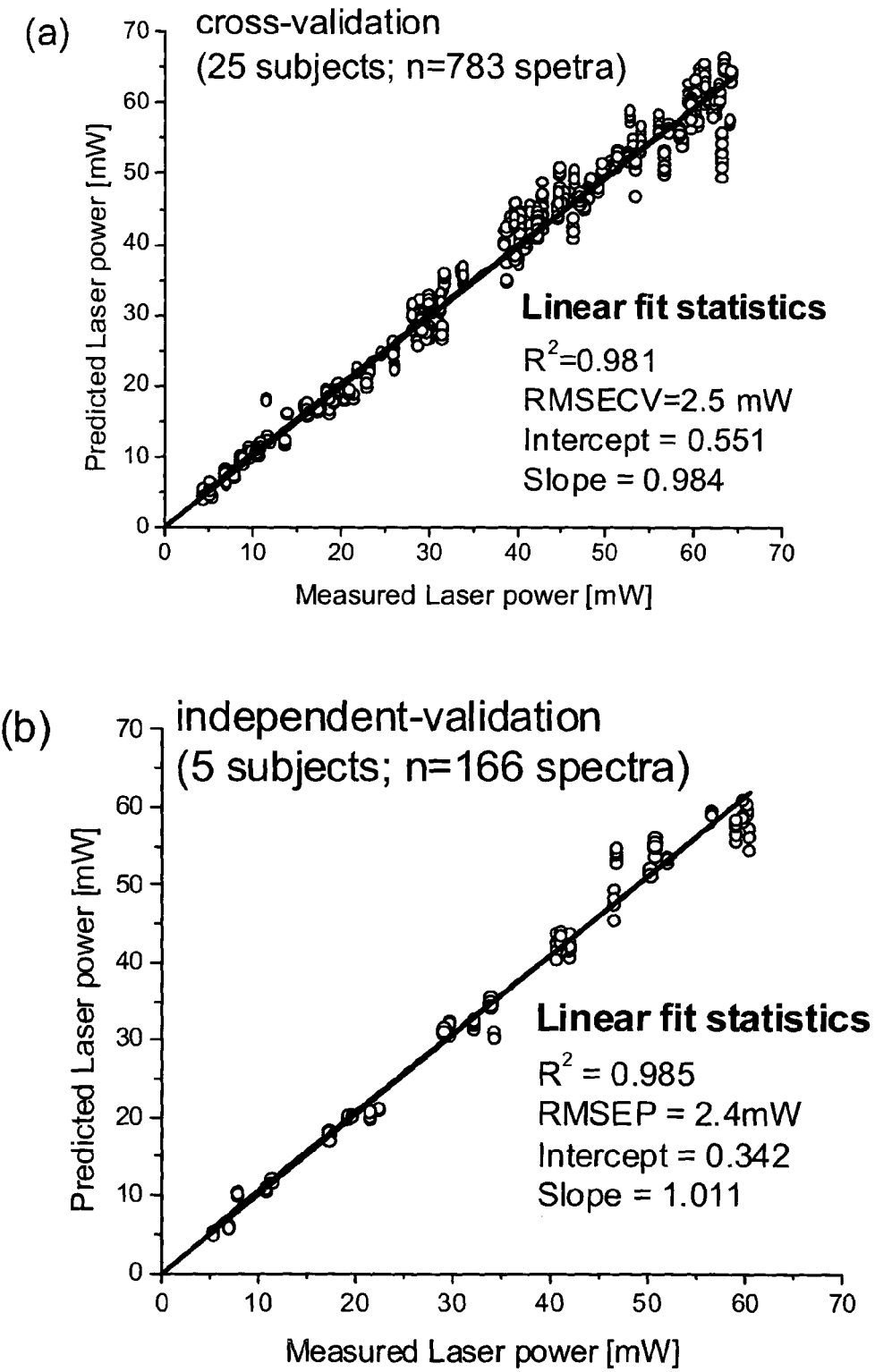
FIG. 30a illustrates the relationship between the actual and the predicted laser excitation powers using PLS regression model based on the leave-one subject-out, cross-validation as well as the linear fit to the data.
FIG. 30b illustrates the relationship between the actual and the predicted laser excitation power using PLS regression based on the independent validation.

A PLS regression model to extract a broad range of characteristic internal reference peaks from the oral tissue Raman spectra. The Rayleigh scattered light was excluded from PLS analysis. The measured in vivo raw tissue Raman spectra were arranged in a matrix with row-wise spectra and column-wise wavenumbers. The reference laser power levels were arranged in a column vector representing the dependent variables. After mean-centering, a PLS regression model was developed using the leave-one subject-out, cross-validation in order to establish the optimum algorithm for rendering robust reference signals for laser excitation power prediction. FIG. 14a shows the RMSEC and RMSECV of laser power prediction as a function of retained LVs. The PLS regression analysis showed that an optimal model (RMSECV=2.5 mW) could be obtained using 4 LVs. FIG. 14b displays the first four LV loadings accounting for the largest Raman spectral variance (i.e., LV1: 94.8%, LV2: 3.0%, LV3: 0.9% and LV4: 0.2%) and laser excitation power variance (LV1: 80.1%, LV2: 16.8%, LV3: 0.8% LV4: 0.7%). Also shown is the calculated PLS regression vector. FIG. 30a shows the in vivo laser power monitoring results (i.e., measured laser power vs. predicted laser power) using a leave-one subject-out, cross validation. The data can be fitted by the equation (y=0.551+0.984x) indicating a substantial linear relationship (R=0.98). The PLS model complexity of 4 LVs offered an accurate internal reference for laser excitation power monitoring with a RMSECV of 2.5 mW and $R^2$ of 0.981. The same PLS regression model was subsequently implemented on-line in the Raman software for independent validation of the 5 new subjects (n=166 spectra) in real-time. FIG. 30b shows the relationship between the actual laser excitation power measured and the predicted laser excitation power using the developed PLS regression model. The RMSEP of 2.4 mW and a linear relationship (y=0.342+1.011x; $R^2$=0.985) can be obtained, reconfirming the application of PLS regression as an internal reference method during in vivo tissue Raman measurements.

Figure 31:
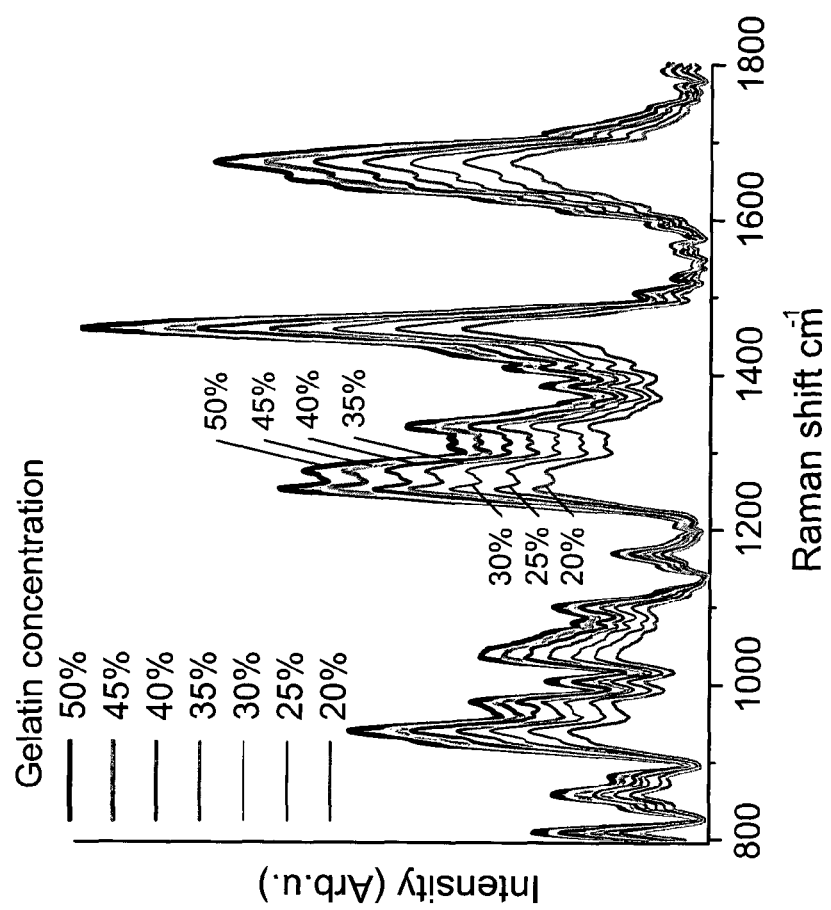
FIG. 31 illustrates Raman spectra of gelatin tissue phantoms prepared with different concentrations (i.e., 20, 25, 30, 35, 40, 45, and 50% by weight) measured at 60 mW laser excitation power.
Figure 32:
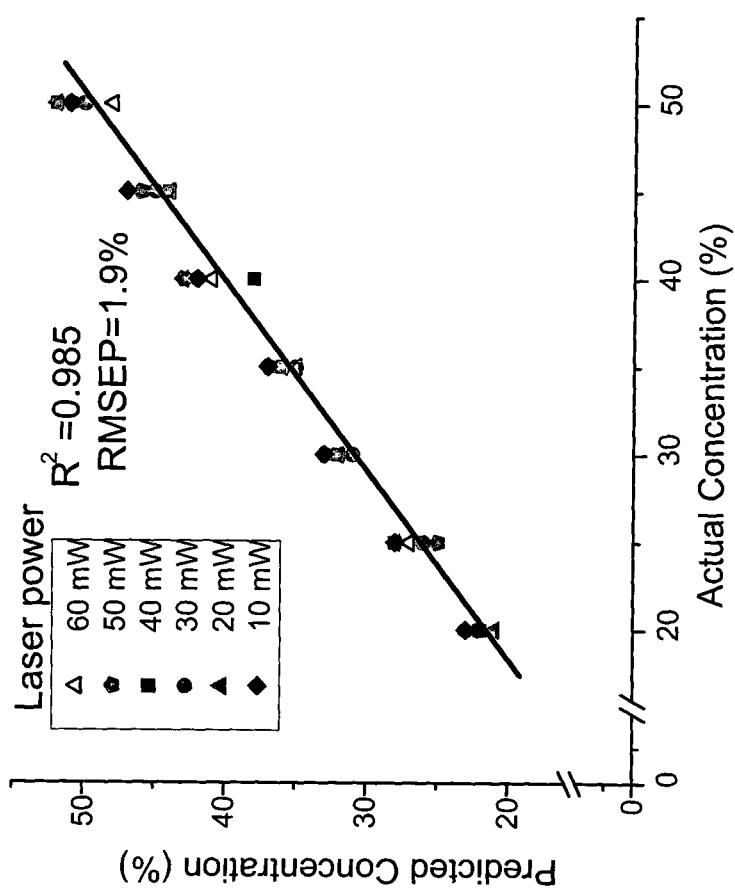
FIG. 32 illustrates the correlationship between the actual and predicted gelatin concentrations in tissue phantoms after the correction with the predicted laser power.

The quantitative value of the internal-reference method developed for quantitative spectral analysis of tissue phantoms. Seven tissue phantoms composed of gelatin with different concentrations (i.e., 20, 25, 30, 35, 40, 45, and 50% by weight) were constructed and tested. Raman spectra (n=133 spectra) from gelatin phantoms were measured and normalized to the laser powers predicted in real-time. FIG. 31 shows the Raman spectra measured from gelatin tissue phantoms with different concentrations at 60 mW excitation laser power. As expected, these Raman spectra show a linear relationship (R=0.992) between the Raman peak intensities and gelatin concentrations. FIG. 32 shows the correlationship between the actual gelatin concentrations and the predicted concentrations with varying excitation laser powers (varying from 10 to 60 mW). It is evident that by correcting the laser power variation through real-time laser excitation power monitoring in situ, accurate quantitative analysis of gelatin tissue phantoms can be realized (RM- SEP=1.9% and $R^2$=0.985). The above results indicate that the developed real-time power monitoring method based on multivariate internal reference signals can achieve robust quantitative compositional analysis in fiber-optic tissue Raman spectroscopy.

Example 3—In Vivo Real-Time Transnasal Image-Guided Raman Endoscopy: Defining Spectral Properties in the Nasopharynx and Larynx This study demonstrates the feasibility of Raman spectroscopy in transnasal endoscopic applications, providing the foundation for large-scale clinical studies in the head and neck. The image-guided Raman endoscopy platform integrated with a miniaturized fiber Raman probe developed provides a rapid and minimally invasive assessment of endogenous tissue constituents of the head and neck at the molecular level during clinical endoscopic examination. This greatly facilitates clinicians to obtain detailed biomolecular fingerprints of tissue in the head and neck, reflecting the genuine compositional and morphological signatures without introducing the artifacts caused by vascular puncturing or tissue dehydration, morphological and anatomical effects, etc.

The Raman spectroscopy system consists of a spectrum stabilized 785 nm diode laser (maximum output: 300 mW, B&W TEK Inc., Newark, Del.), a transmissive imaging spectrograph (Holospec f/1.8, Kaiser Optical Systems) equipped with a cryogenic cooled (−120° C.), NIR-optimized, back-illuminated and deep depletion charge-coupled device (CCD) camera (1340×400 pixels at 20×20 µm per pixel; Spec-10: 400BR/LN, Princeton Instruments). The novel spectrometer fiber input coupling consists of parabolic aligned array of 58 fibers (100 µm) to correct the spectrometer image aberration for improving both the spectral resolution and signal-to-noise ratio of Raman signals. A 1.8 mm fiber-optic Raman probe for transnasal endoscopic applications maximizing both the tissue excitation and in vivo tissue Raman collections was utilized. The Raman fiber probe fits into the instrument channel of flexible transnasal endoscopes and can be safely directed to different locations in the nasopharynx and larynx under the wide field imaging (i.e., white-light reflectance (WLR) and narrowband imaging (NBI)) guidance. The clinical Raman endoscopy platform has been integrated with our recently developed on-line data processing software to facilitate probe handling-advise and sound feedback to clinicians in real-time (processing time<0.1 s). Briefly, the on-line Raman endoscopy framework synchronizes spectral acquisition (i.e., laser exposure, integration time, CCD shutter and readout etc.) and automatically extracts the Raman signals from the raw tissue spectra (comprising strong autofluorescence background and weak Raman signals) using the established preprocessing methods including smoothing, fifth-order polynomial baseline subtraction etc. The in vivo Raman spectra and the outcome of multivariate algorithms (e.g., principal component analysis) can be displayed in real-time in a comprehensible graphical user interface (GUI) during clinical transnasal Raman endoscopy.

A total of 23 normal healthy male subjects of different races (twenty-two Asian and one Caucasian) were recruited for in vivo tissue Raman measurements at transnasal endoscopy. In these subjects recruited, no suspicious lesions were identified under the WLR and NB imaging examination. A total of three primary measurement sites of assumed normal (or benign) tissues were predefined for in vivo Raman acquisitions, including the true laryngeal vocal cords (LVC), the posterior nasopharynx (PN), and also the pharyngeal recess (i.e., fossa of Rosenmüller (FOR)) where NPC typically initiates. The fiber-optic Raman probe can be placed in gentle contact with internal tissues interrogating with the endogenous biomolecular compositions of tissue in real-time. The accurate positioning against the biopsied tissue sites was verified on the WLR/NBI monitor by the endoscopists in-charge. The probe allowed Raman spectra to be collected from an area (200 µm in diameter) with probing volume of approximately 1 $mm^3$ and penetration depth of ~800 µm. Each spectrum was acquired within 0.5 s using the 785 nm laser light with the power of ~50 mW on the tissue surface.

The Raman spectra were displayed on-line and were stored for post-procedural inspection. This rapid Raman endoscopic technology is non-destructive, and can now routinely be used under endoscopic transnasal examinations for clinical evaluation. To assess the intra-tissue site variance, several Raman spectra (~18) were also acquired from each tissue site. As a result, a total of 874 in vivo Raman spectra from 47 sites were measured at transnasal endoscopy and used for spectral analysis [PN (n=521), FOR (n=157) and LVC (n=196)] from the 23 subjects.

Prior to data-analysis, the raw Raman spectra were firstly smoothed using a linear Savitzky Golay filter, and tissue autofluorescence background was then subtracted from the smoothed spectra using a $5^{th}$ order polynomial fit. The background-subtracted Raman spectra were normalized to the integrated areas under the curves to minimize the effect of Raman probe handling variations on clinical Raman measurements with respect to different subjects and tissue sites. All processed Raman spectra were assembled into a matrix, and the mean centering of the entire Raman dataset was then performed. To reduce the dimension of the spectral data, principal component analysis (PCA) was employed to extract a set of orthogonal principal components (PCs) that account for the maximum variance in the Raman spectral dataset for tissue characterization. Accordingly, loadings on the PCs represent orthogonal basis spectra of the most prominent spectral variation in the dataset accounting for progressively decreasing variance, whereas the scores on the PCs represent the projection value of the tissue Raman spectra on the corresponding loading. Thus, PCA can efficiently be used to resolve spectral variations while reducing the dimension of the dataset to a minimum. The number of retained PCs was chosen based on the analysis of variance (ANOVA) and Student's t-test at 0.05 level. We employed post-hoc Fisher's least squares differences (LSD) test to assess differences in means. Multivariate statistical analysis was performed using the PLS toolbox (Eigenvector Research, Wenatchee, Wash.) in the Matlab (Mathworks Inc., Natick, Mass.) programming environment.

Figure 33:
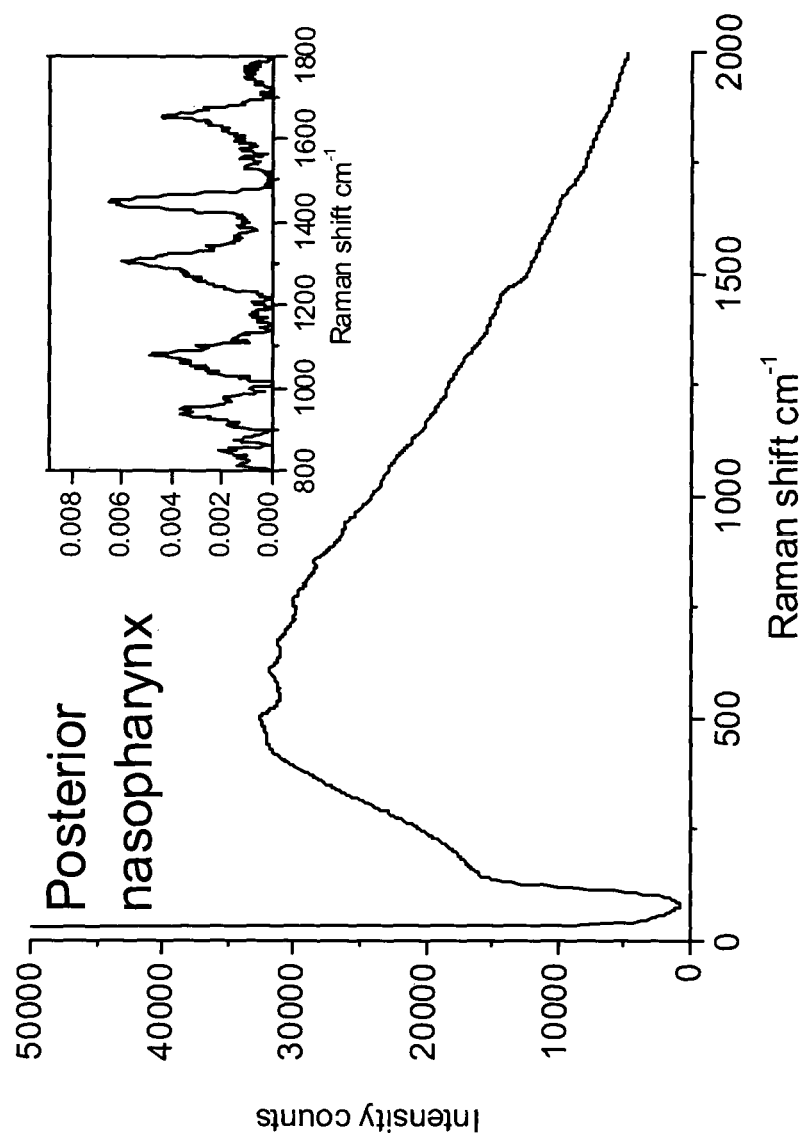
FIG. 33 illustrates representative in vivo raw Raman spectrum acquired from the Fossa of Rosenmüller with 0.1 s during clinical endoscopic examination. Inset of FIG. 33 is the processed tissue Raman spectrum after removing the intense autofluorescence background.
Figure 34:
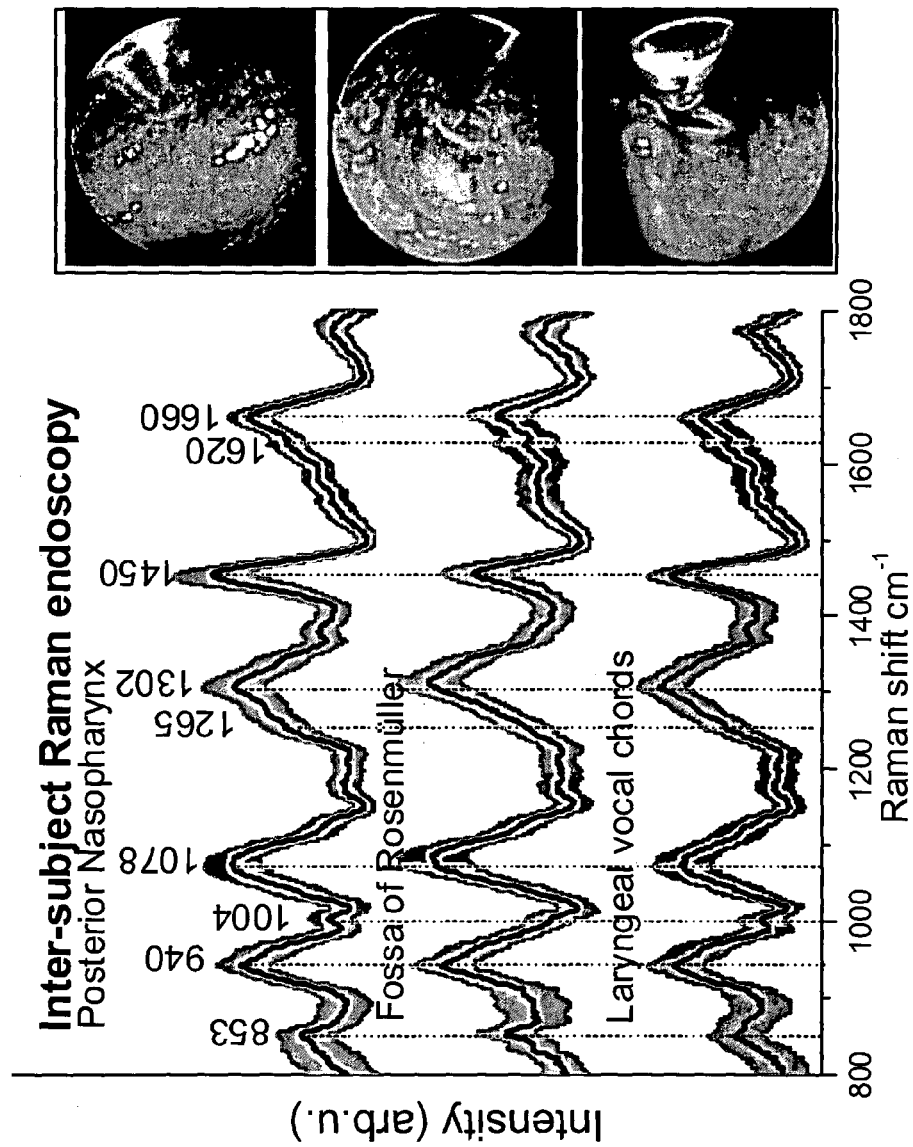
FIG. 34 illustrates in vivo (inter-subject) mean Raman spectra±1 standard deviations (SD) of posterior nasopharynx (PN) (n=521), fossa of Rosenmüller (FOR) (n=157) and laryngeal vocal chords (LVC) (n=196). Note that the mean Raman spectra are vertically displaced for better visualization. In vivo fiber-optic Raman endoscopic acquisitions from posterior nasopharynx (upper) fossa of Rosenmüller (mid) and laryngeal vocal chords (lower) under white light reflectance (WLR) and narrowband (NB) imaging guidance are also shown.

High quality in vivo Raman spectra can routinely be acquired in the nasopharynx and larynx in real-time during transnasal image-guided (i.e., WLR and NBI) endoscopic inspections. FIG. 1 shows an example of in vivo raw Raman spectrum (weak Raman signal superimposed on large tissue autofluorescence background) acquired from the posterior nasopharynx with an acquisition time of 0.1 s at endoscopy. The background-subtracted tissue Raman spectrum with a signal-to-noise ratio (SNR) of >10 (Inset of FIG. 33) can be obtained and displayed online during clinical endoscopic measurements. FIG. 34 depicts the inter-subject in vivo mean Raman spectra±1 standard deviations (SD) of normal nasopharyngeal [PN (n=521) and FOR (n=157)] and laryngeal tissues [LVC (n=196)] when the Raman probe is gently contacted with the tissue under WLR/NB imaging guidance.

Comparisons with the nasopharyngeal and laryngeal tissue Raman spectra acquired (FIG. 34), demonstrates that those biochemical in the body fluids do not contribute significantly to the in vivo tissue Raman spectra at transnasal endoscopy. Also shown is WLR images obtained from the corresponding anatomical locations. Prominent Raman bands associated with proteins and lipids are identified as tabulated in Table 2 with tentative biomolecular assignments.

TABLE 2

Tentative assignments of molecule vibrations and biochemicals involved in Raman scattering of nasopharyngeal and laryngeal tissue (wherein ν, stretching mode; $ν_s$, symmetric stretching mode; δ, bending mode).

| Raman peaks ($cm^{-1}$) | Vibrations | Biochemicals |
|---|---|---|
| 853 | ν(C—C) | proteins |
| 940 | ν(C—C) | proteins |
| 1004 | $ν_s$(C—C) breathing | proteins |
| 1078 | ν(C—C) | lipids |
| 1265 | Amide III ν(C—N) δ(N—H) | proteins |
| 1302 | $CH_2$ twisting and wagging | lipids/proteins |
| 1450 | δ($CH_2$) | lipids/proteins |
| 1660 | Amide I ν(C═O) | proteins |

Figure 35:
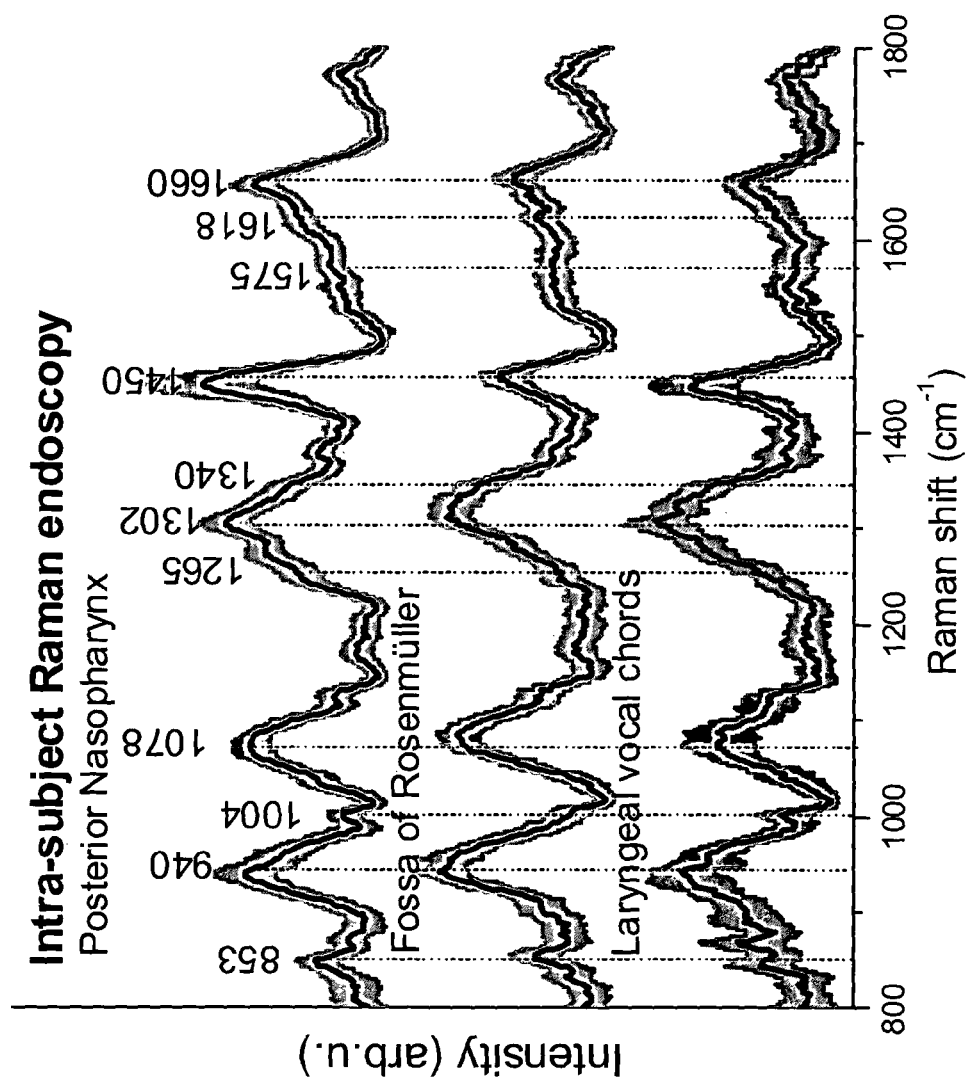
FIG. 35 illustrates in vivo (intra-subject) mean Raman spectra±1 SD of PN (n=18), FOR (n=18) and LVC (n=17). Note that the mean Raman spectra are vertically displaced for better visualization.
Figure 36:
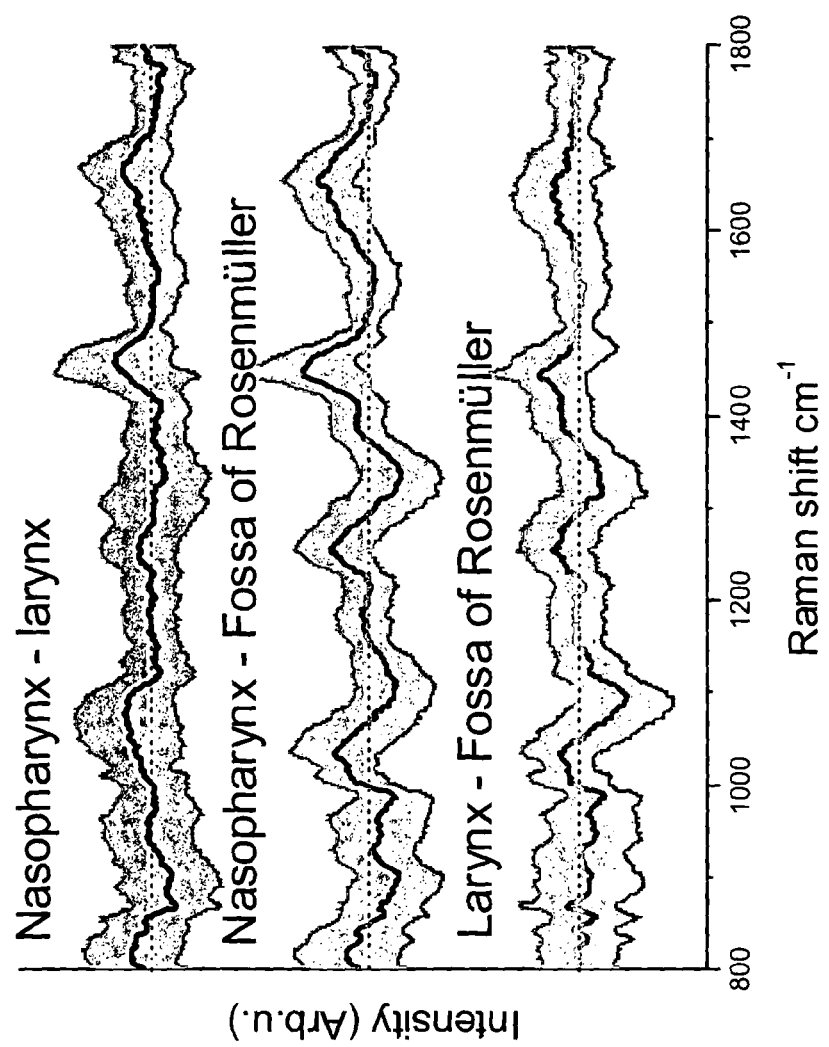
FIG. 36 illustrates the comparison of difference spectra±1 SD of different anatomical tissue types (inter-subject): [posterior nasopharynx (PN)–laryngeal vocal chords (LVC)]; [posterior nasopharynx (PN)–fossa of Rosenmüller (FOR)] and [laryngeal vocal chords (LVC)–fossa of Rosenmüller (FOR)].

FIG. 35 shows the intra-subject mean spectra±1 SD of a randomly chosen subject. The in vivo tissue Raman spectra were found to be reproducible with diminutive inter- and intra-subject variances (<10%) in the nasopharynx and larynx. Further Raman endoscopic testings indicate that the variability between different tissue sites within the posterior nasopharynx is subtle (<5%) (data not shown). We also calculated difference spectra±1 SD between different tissue types (i.e., PN-LVC, LV-FOR and PN-FOR) as shown in FIG. 36, resolving the distinctive compositional and morphological profiles of different anatomical tissue sites at the biomolecular level. ANOVA revealed twelve prominent and broad Raman spectral sub-regions that showed significant variability [$p<0.0001$] between the three anatomical tissue sites centered at: 812, 875, 948, 986, 1026, 1112, 1254, 1340, 1450, 1558, 1655 and 1745 $cm^{-1}$, reconfirming the importance of characterizing the Raman spectral properties of nasopharynx and larynx toward accurate in vivo tissue diagnostics.

Figure 37:
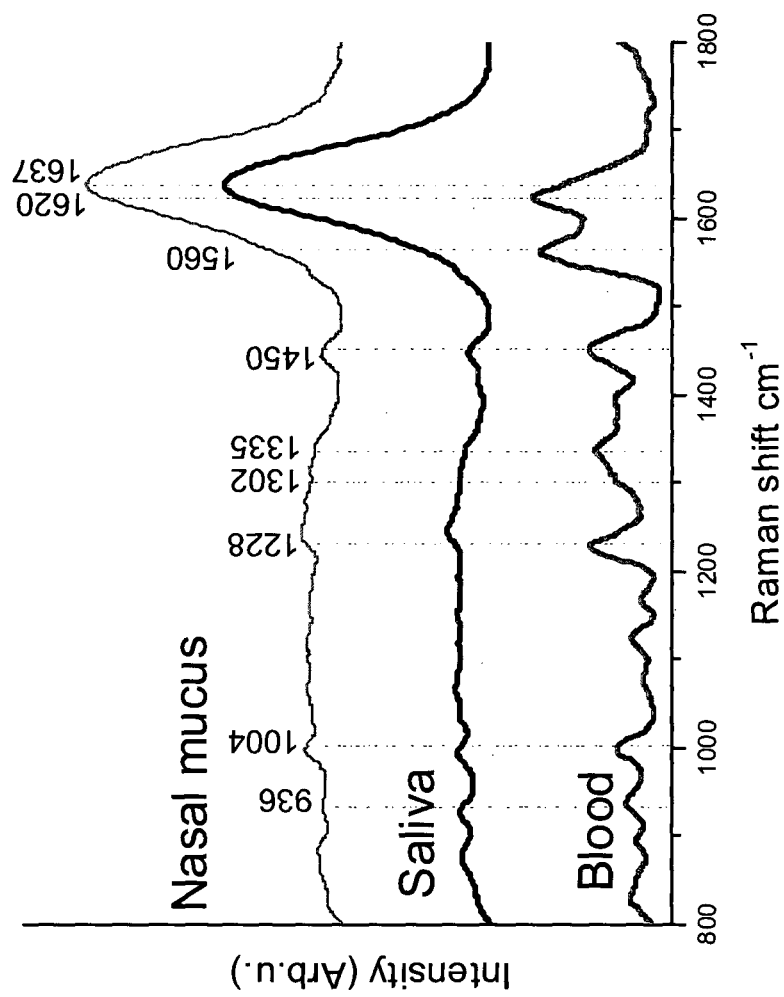
FIG. 37 illustrates in vitro Raman spectra of possible confounding factors from human body fluids (nasal mucus, saliva and blood).
Figure 38:
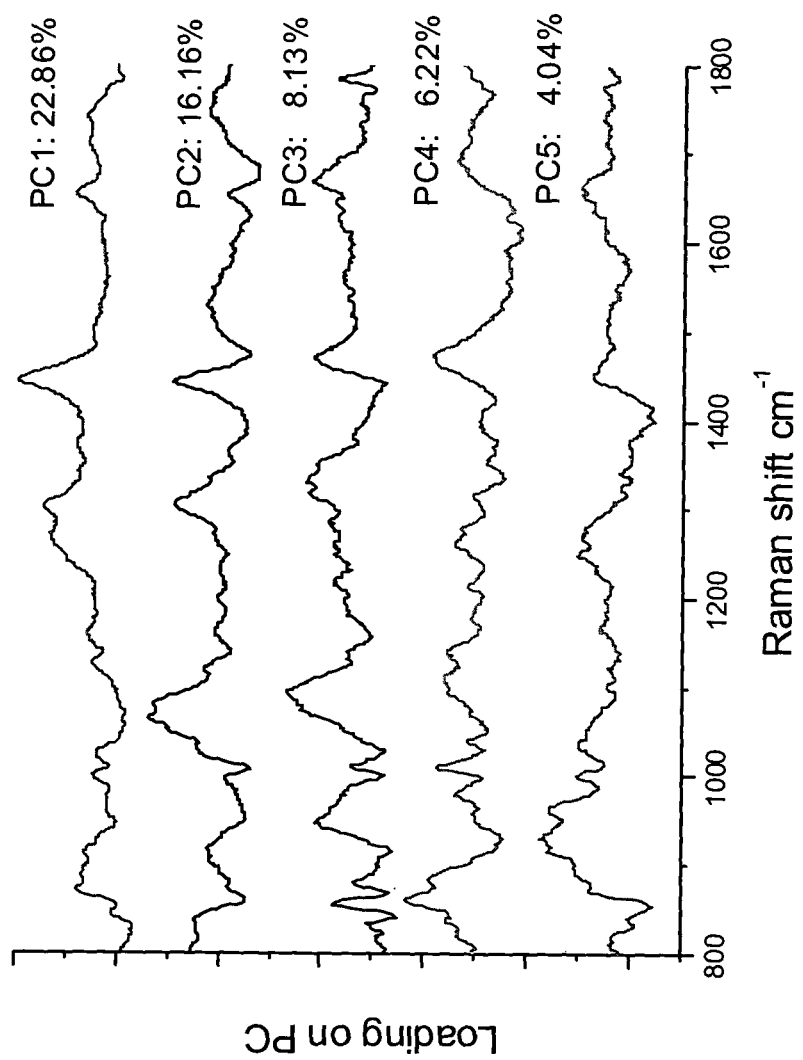
FIG. 38 illustrates PC loadings resolving the biomolecular variations among different tissues in the head and neck, representing a total of 57.41% (PC1: 22.86%; PC2: 16.16%; PC3: 8.13%; PC4 6.22% PC5: 4.05%) of the spectral variance.
Figure 39A:
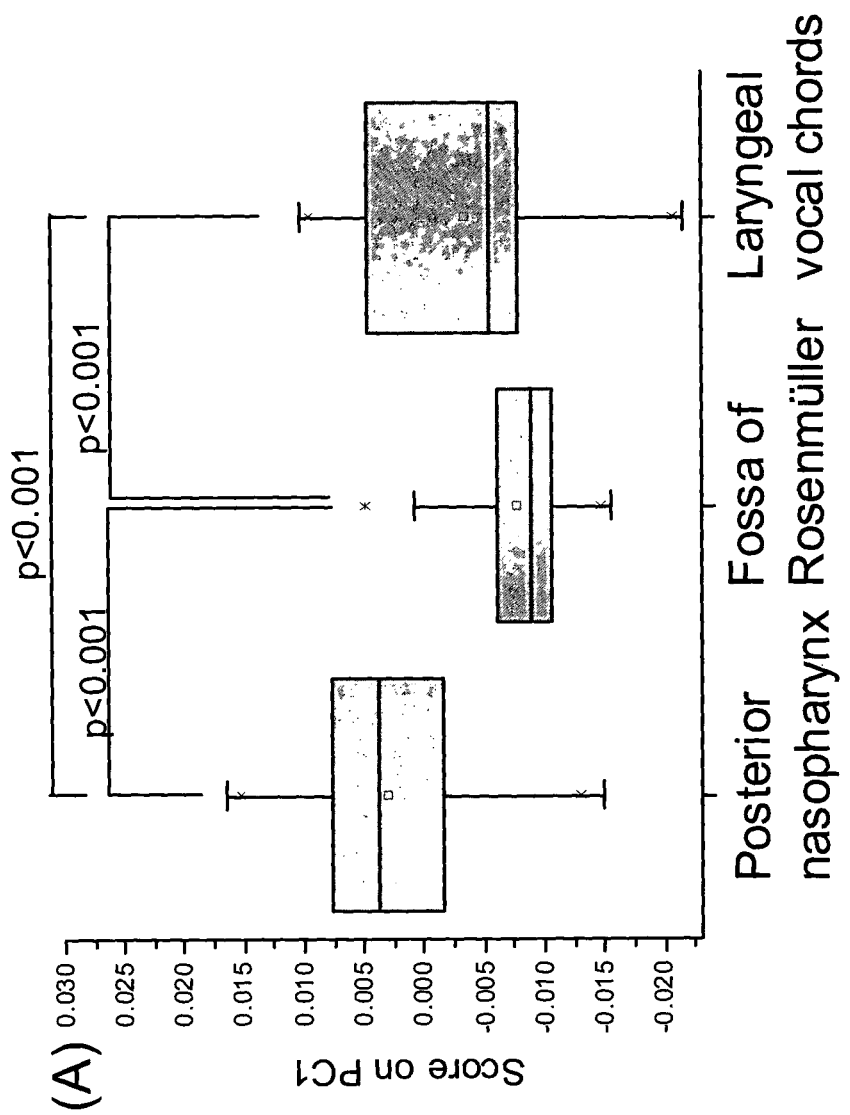
FIG. 39 provides box charts of the 5 PCA scores for the different tissue types (i.e., PN, FOR and LVC). The line within each notch box represents the median, but the lower and upper boundaries of the box indicate first (25.0% percentile) and third (75.0% percentile) quartiles, respectively. Error bars (whiskers) represent the 1.5-fold inter-quartile range. The p-values are also given among different tissue types.
Figure 39B:
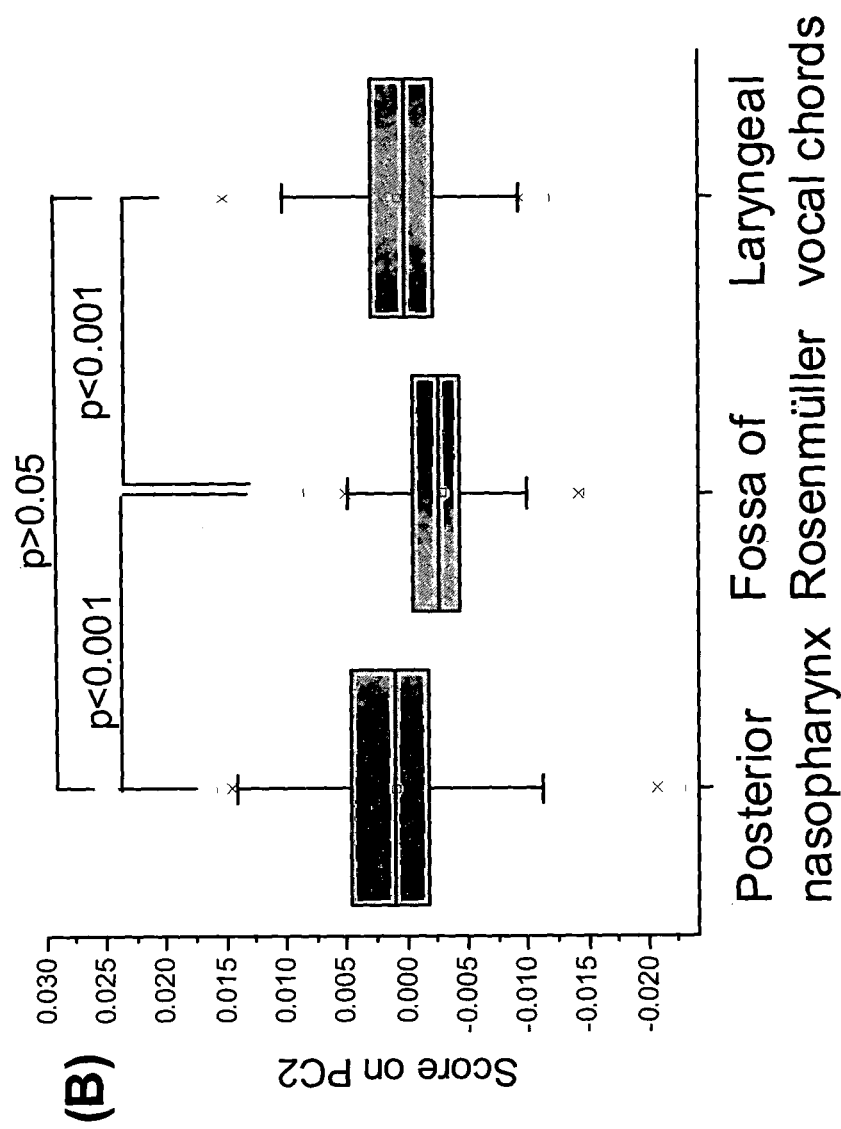
Figure 39C:
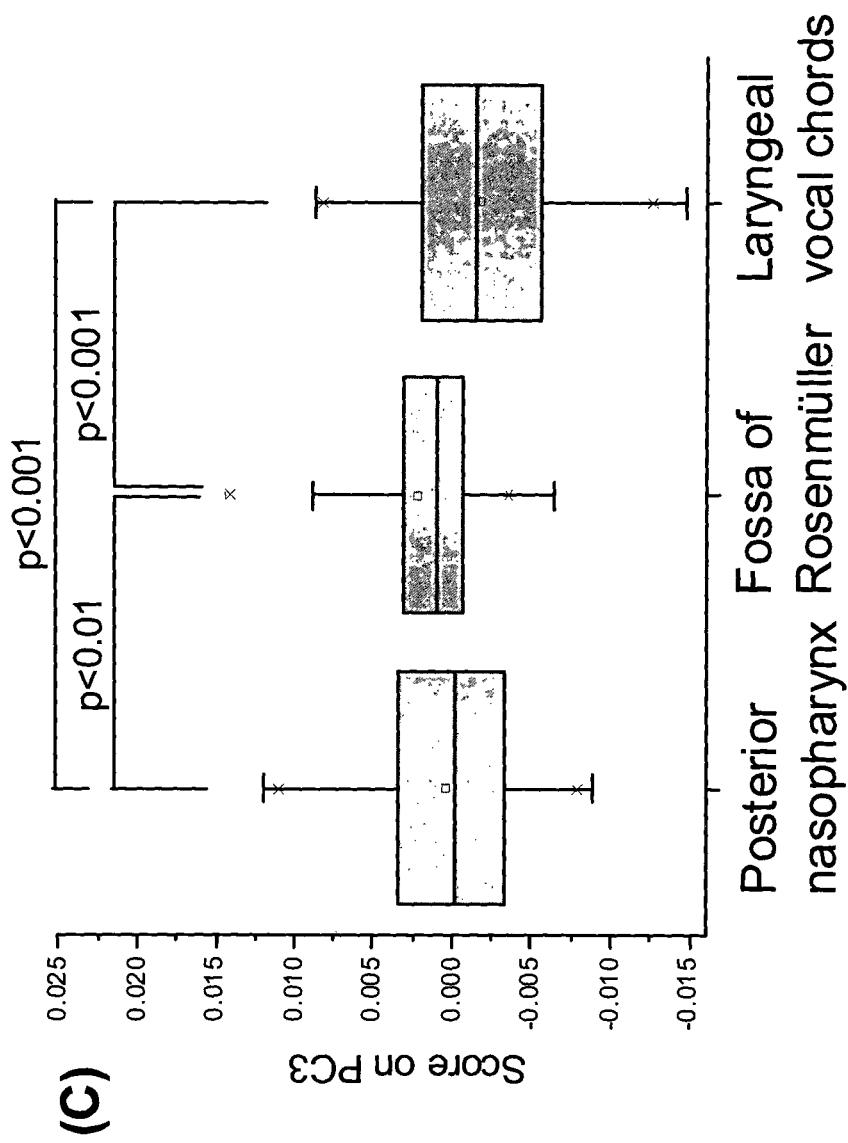
Figure 39D:
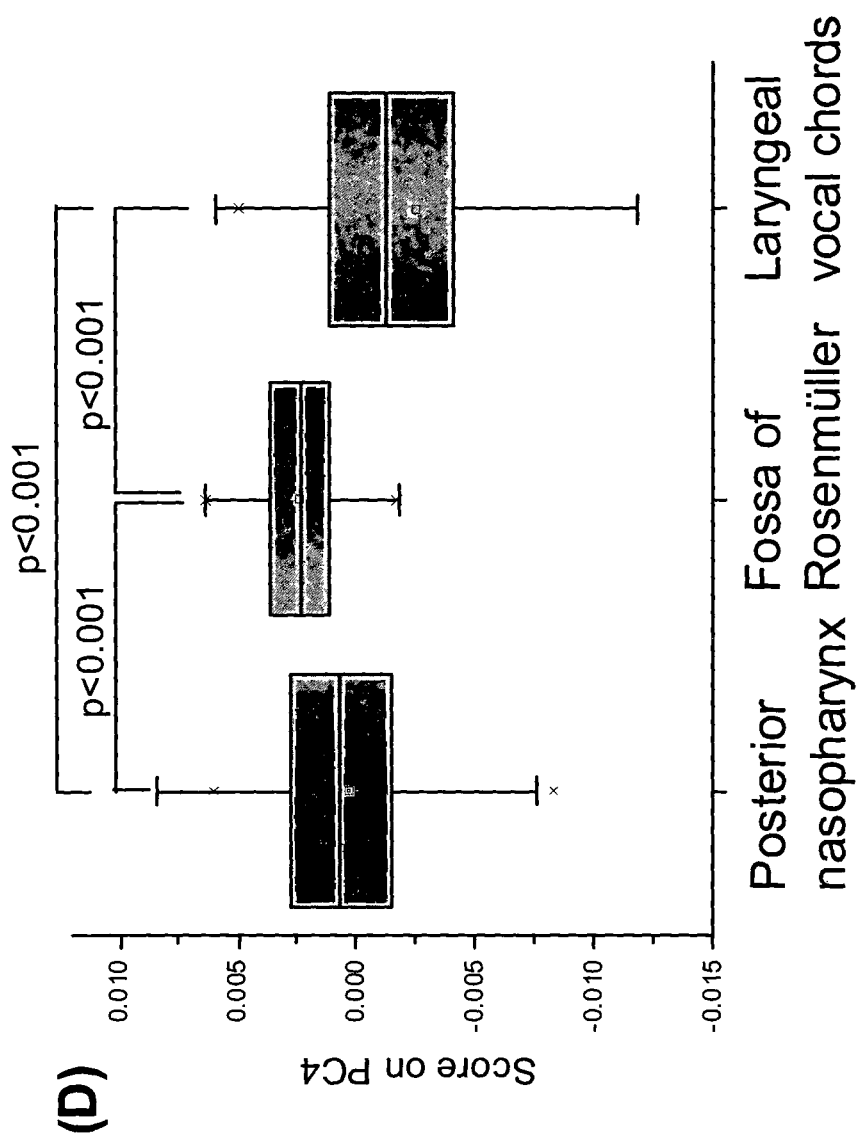
Figure 39E:
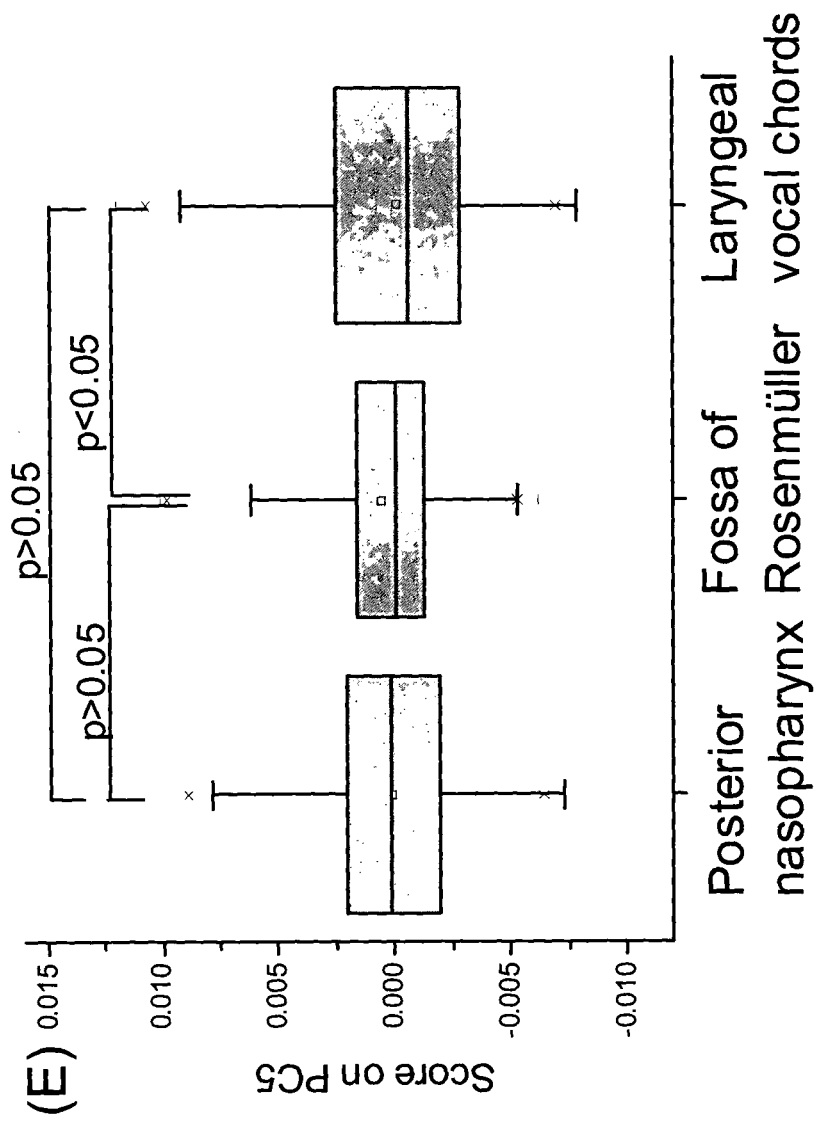

In vitro Raman spectra of blood, saliva and nasal mucus obtained from healthy volunteers were measured as shown in FIG. 37. The most prominent Raman bands in saliva and nasal mucus are at 1638 $cm^{-1}$ ($v_2$ bending mode of water), whereas blood exhibits porphyrin Raman bands nearby 1560 and 1620 $cm^{-1}$ [31]. To further assess the spectral differences among different tissues in the head and neck, a five-component PCA model based on ANOVA and student's t-test ($p<0.05$) accounting for 57.41% of the total variance (PC1: 22.86%; PC2: 16.16%; PC3: 8.13%; PC4 6.22% PC5: 4.05%) was developed to resolve the significant peak variations of different anatomical locations. FIG. 38 shows the PC loadings revealing the resolve Raman bands associated with proteins (i.e., 853, 940, 1004, 1265, 1450 and 1660 $cm^{-1}$) and lipids (i.e., 1078, 1302 1440, 1655 and 1745 $cm^{-1}$). FIG. 39 (A to E) displays box charts of PCA scores for the different tissue types (i.e., PN, FOR and LVC). The line within each notch box represents the median, and the lower and upper boundaries of the box indicate first (25.0% percentile) and third (75.0% percentile) quartiles, respectively. Error bars (whiskers) represent the 1.5-fold interquartile range. The p-values are also represented among different tissue types. Dichotomous PCA algorithms integrated with linear discriminant analysis (LDA) provided the sensitivities of 77.0% (401/521), 67.3% (132/192) and specificities of 89.2% (140/157) and 76.0% (396/521) for differentiation between PN vs. FOR, and LVC vs. PN, respectively using leave-one subject-out, cross validation. Overall, these results demonstrate that Raman spectra of nasopharynx and larynx in the head and neck can be measured in vivo at transnasal endoscopy, and the diagnostic algorithms development should be tissue site specific to ensure minimum algorithm complexity.

Example 4—Fiber-Optic Confocal Raman Spectroscopy for Real-Time In Vivo Diagnosis of Dysplasia in Barrett's Esophagus Fiber-optic confocal Raman diagnostics can be achieved in real-time (<0.5 second) and uncovers the progressive biomolecular and functional changes of epithelial cells and tissues in Barrett's carcinogenesis in situ. Histopathology characterized 152 of the prospectively measured tissue sites as columnar lined epithelium (n=597 spectra), 48 as intestinal metaplasia (n=123 spectra), 9 high-grade dysplasia (n=77 spectra). Using receiver operating characteristics (ROC) analysis, identification of high-grade dysplasia could be successfully achieved yielding a sensitivity of 87.0%, and a specificity of 84.7% on spectrum basis. The area under the ROC curve was found to be 0.90. This new biomolecular specific endoscopic modality with real-time capability offers the gastroenterologist a reliable tool to objectively target high-risk tissue areas in Barrett's patients during ongoing endoscopy.

The confocal Raman spectroscopic system comprises of a near-infrared (NIR) diode laser ($\lambda_{ex}$=785 nm), a high-throughput transmissive imaging spectrograph equipped with a liquid nitrogen-cooled, NIR-optimized charge-coupled device (CCD) camera and a specially designed 1.8-mm fiber-optic confocal Raman probe. The system acquires Raman spectra in the range 800-1800 $cm^{-1}$ with a spectral resolution of ~9 $cm^{-1}$. The developed fiber-optic confocal Raman endoscopic probe is used for both laser light delivery and in vivo tissue Raman signal collection.

The 1.8 mm (in outer diameter) confocal Raman endoscopic probe comprises 9×200 μm filter-coated collection fibers (NA=0.22) surrounding the central light delivery fiber (200 μm in diameter, NA=0.22). A miniature 1.0 mm sapphire ball lens (NA=1.78) is coupled to the fiber tip of the confocal probe to tightly focus the excitation light onto tissue, enabling the effective Raman spectrum collection from the epithelial lining (<200 μm). The fiber-optic confocal Raman probe can be inserted into the instrument channel of conventional endoscopes and placed in gentle contact with the epithelium for in vivo tissue characterization and diagnosis. The depth-selectivity of this confocal Raman probe offers compelling experimental advantages, including (i) fiber-optic confocal Raman spectroscopy selectively targets the epithelial lining associated with early onset of Barrett's carcinogenesis, which is superior to conventional volume-type fiber-optic Raman probes that interrogate a larger tissue volume; (ii) the shallower tissue interrogation ability of confocal Raman technique provides a higher tissue Raman to autofluorescence background ratio due to a much reduced tissue autofluorescence contribution from deeper tissue layers (e.g., stroma), and (iii) combining this novel fiber-optic confocal Raman spectroscopy platform with well-documented multivariate analysis enables epithelial molecular information to be extracted and analyzed in real-time in vivo. The entire confocal Raman endoscopic system is controlled in an intuitive software framework that permits rapid survey in endoscopic screening settings with auditory probabilistic feedback to the endoscopist, pushing the frontier of Raman spectroscopy into routine clinical diagnostics.

Figure 40A:
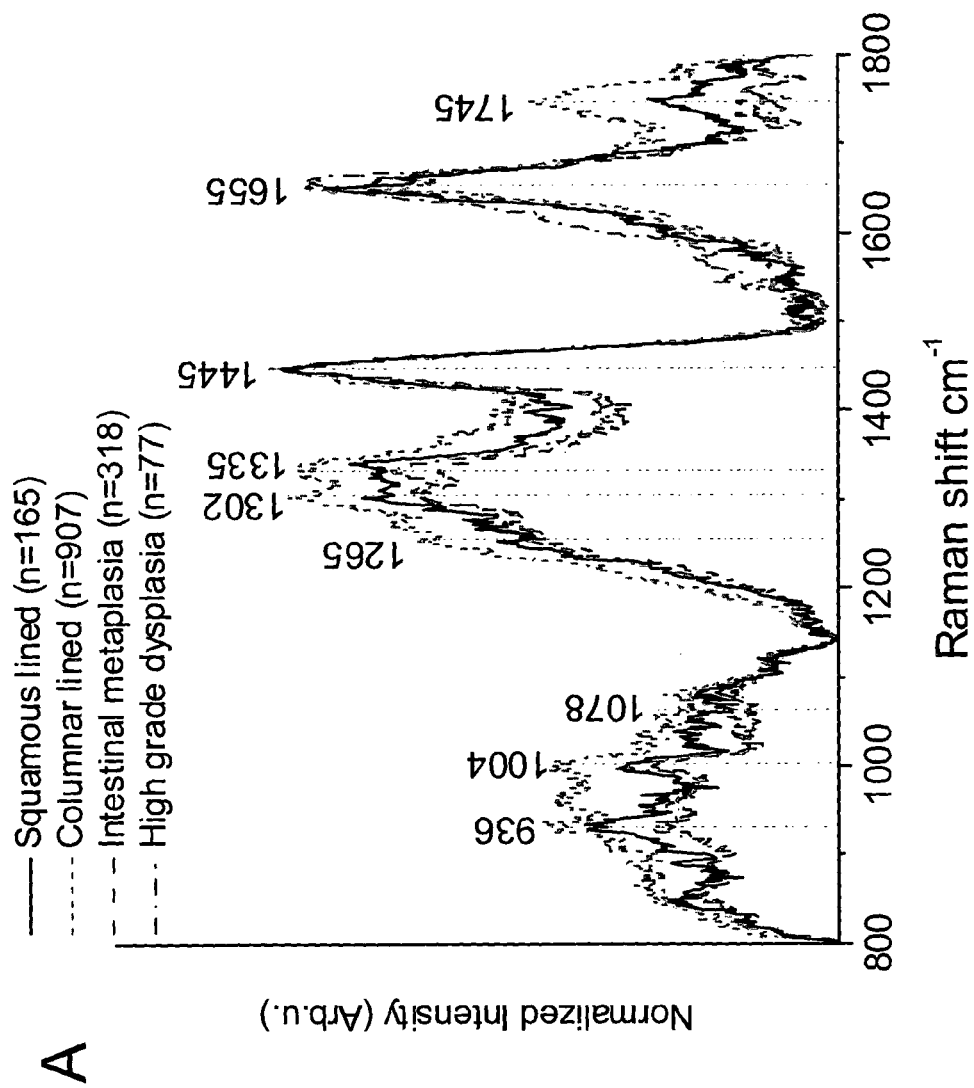
FIG. 40A illustrates mean in vivo confocal Raman spectra of squamous lined epithelium (n=165), columnar lined epithelium (n=907), Barrett's esophagus (n=318), high-grade dysplasia (n=77) acquired during clinical endoscopic examination.

A total of 450 patients have been enrolled in the Raman endoscopic examinations for surveillance or screening of various indications, including dyspepsia and upper GI neoplasia. During a typical examination of suspicious lesions, each tissue Raman measurement can be acquired within 0.5 second, which permits rapid survey of large tissue areas. The in vivo Raman spectral data acquired from 373 patients with different histological subtypes in the upper GI have been used to construct a comprehensive Raman library (>12,000 Raman spectra). For the patients recruited for screening and surveillance of BE, Raman spectra are categorized into following three histopathologically risk classes: (i) "Normal"—columnar lined epithelium (CLE), (ii) "Low-risk" BE-defined as the presence of goblet cells, (iii) "High-risk"-low-grade dysplasia (LGD) and high-grade dysplasia (HGD). For example, FIG. 40A shows the mean in vivo confocal Raman spectra measured from patients in our database presenting with different tissue types (i.e., squamous lined epithelium (n=165), CLE (n=907), intestinal metaplasia (IM) (n=318) and HGD (n=77)) as confirmed by histopathological characterization. Each Raman spectrum was acquired within 0.5 sec. The spectra have been normalized to the Raman peak at 1445 $cm^{-1}$ for comparison purpose. Prominent tissue Raman peaks can be observed at around: 936 $cm^{-1}$ ($\nu$(C—C) proteins), 1004 $cm^{-1}$ ($\nu_s$(C—C) ring breathing of phenylalanine), 1078 $cm^{-1}$ ($\nu$(C—C) of lipids), 1265 $cm^{-1}$ (amide III $\nu$(C—N) and $\delta$(N—H) of proteins), 1302 $cm^{-1}$ ($CH_2$ twisting and wagging of proteins), 1445 $cm^{-1}$ ($\delta(CH_2)$ deformation of proteins and lipids), 1618 $cm^{-1}$ ($\nu$(C=C) of porphyrins), 1655 $cm^{-1}$ (amide I $\nu$(C=O) of proteins) and 1745 $cm^{-1}$ ($\nu$(C=O) of lipids). Remarkable Raman spectral differences (e.g., peak intensity, shifting and band broadening) can be discerned among different tissue types. These rich spectral signatures portray the biomolecular and functional changes occurring in the epithelium accompanying Barrett's carcinogenesis. While histology identifies presence of goblet cells and progressive architectural and cytological atypia (FIG. 40(B, C, D, E), fiber-optic confocal Raman spectroscopy reveals that the epithelium undergoes major functional and biomolecular changes throughout Barrett's carcinogenesis sequence. It is intriguing that the Raman biomolecular signature of BE resembles that of dysplasia to a high degree, confirming that transformation to intestinal metaplastic phenotype is a key event in Barrett's carcinogenesis. These highly specific epithelial molecular signatures possibly reflect a multitude of endogenous optical biomarkers (i.e., oncoproteins, DNA, mucin expression, mitoses, etc.).[8] Therefore, correlation of the epithelial Raman spectral signatures with histopathology or histochemistry can deepen the understanding of Barrett's onset and progression in situ at the biomolecular level. Currently, no other competing optical spectroscopic techniques (e.g., fluorescence, elastic scattering spectroscopy) can provide such exhaustive molecular characterization in vivo at endoscopy.

Figure 41A:
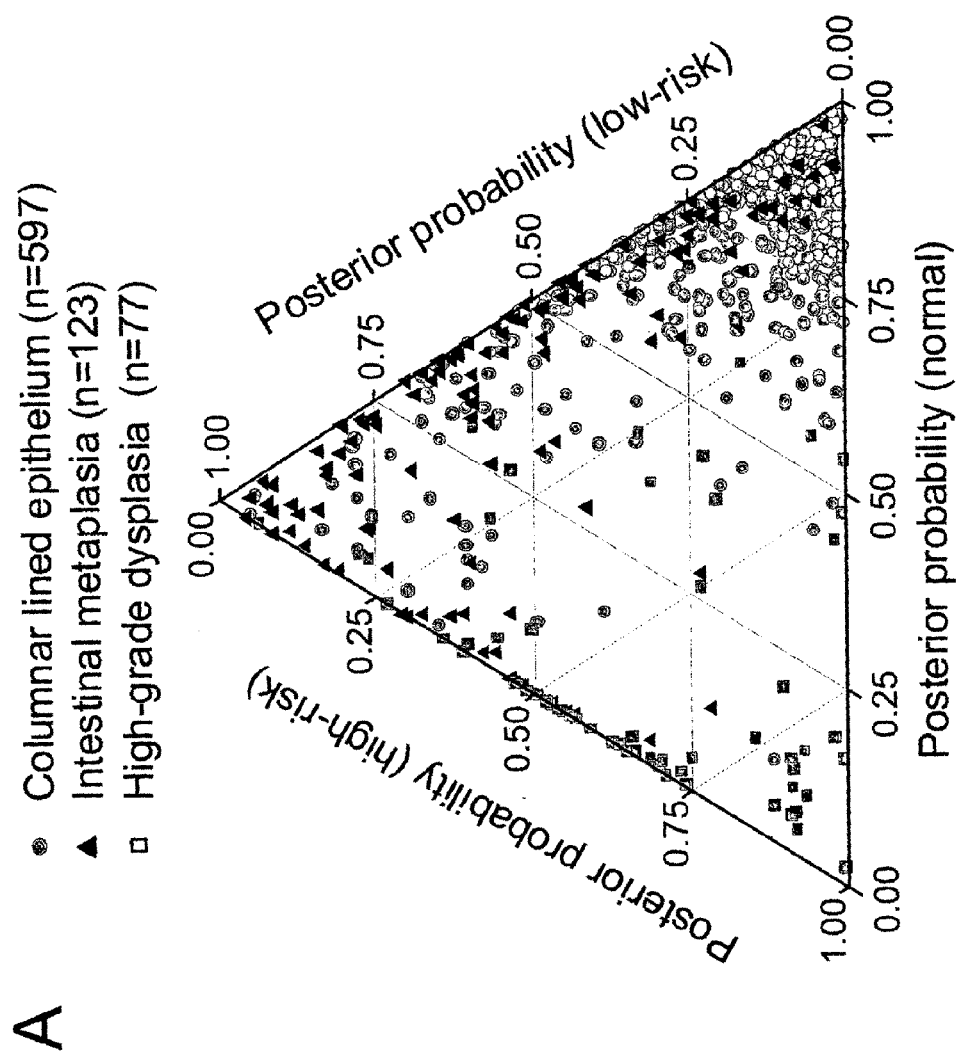
FIG. 41A illustrates two-dimensional ternary plot of the prospective posterior probabilities belonging to 'normal' columnar lined epithelium (CLE), (ii) 'low-risk' intestinal metaplasia (IM) (iii) 'high-risk' high-grade dysplasia (HGD) using confocal Raman endoscope technique.
Figure 41B:
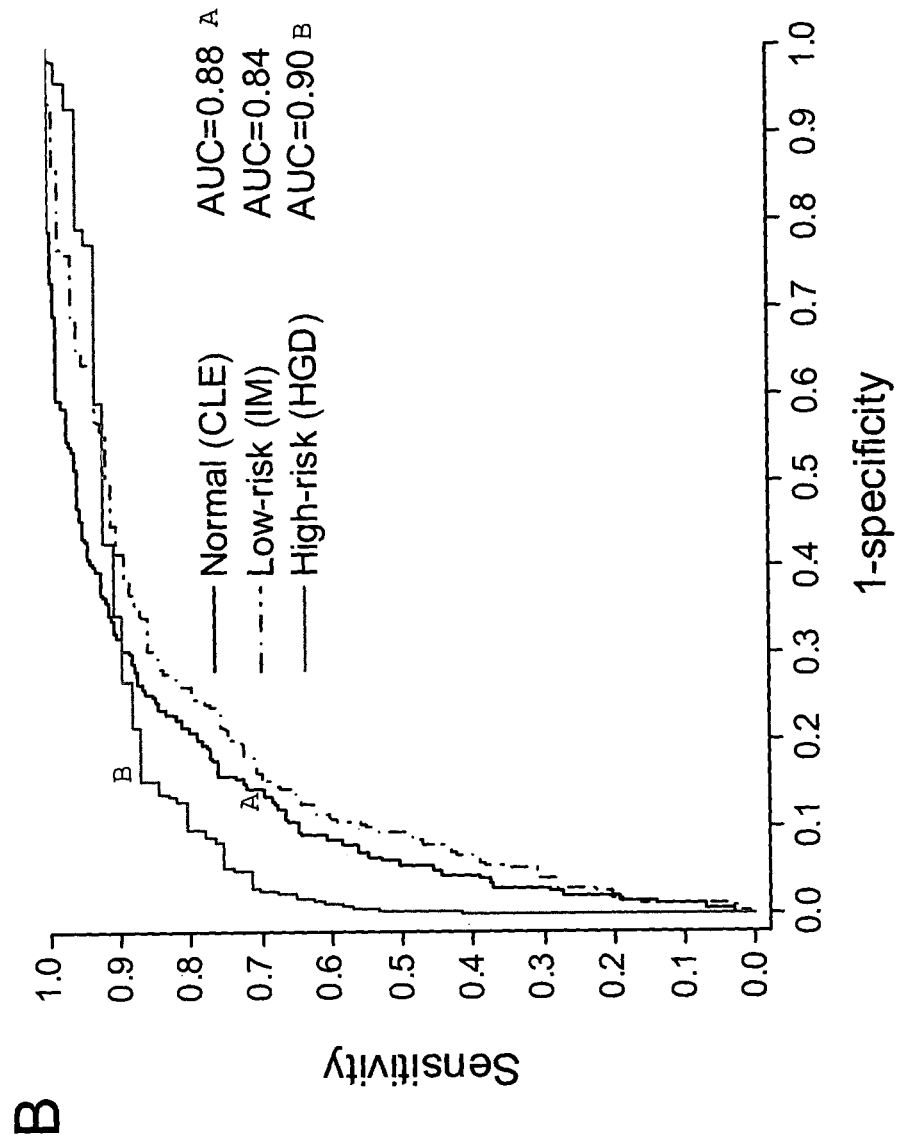
FIG. 41B Receiver operating characteristics (ROC) curves of dichotomous discriminations of 'normal' CLE, (ii) IM (iii) 'high-risk' HGD. The areas under the ROC curves (AUC) are 0.88, 0.84 and 0.90, respectively.

Histopathology characterized 152 of the prospectively (i.e., independently) measured tissue sites as CLE (n=597 spectra), 48 as IM (n=123 spectra) and 9 as HGD (n=77 spectra). FIG. 41A shows a two-dimensional ternary scatter plot of the prospective measured risk scores in 77 patients belonging to confocal Raman spectra of normal, low-risk and high-risk lesions. The corresponding dichotomous receiver operating characteristic (ROC) curves (FIG. 41B) are also generated from FIG. 3A with the area under curve (AUC) being 0.88, 0.84 and 0.90, respectively, for discriminations among normal, low-risk and high-risk lesions. Not only did the confocal Raman technique differentiate the low-risk lesions with BE (FIG. 41A), it was also able to objectively localize the specific tissue areas containing dysplastic epithelium. The above ROC analysis illustrate that the targeted detection of high-risk tissues can be successfully achieved in real-time, yielding a diagnostic sensitivity of 87.0% (67/77), and a specificity of 84.7% (610/720) on spectrum basis.

In the above description, an embodiment is an, example or implementation of the disclosed system and methods. The various appearances of "one embodiment", "an embodiment" or "some embodiments" do not necessarily all refer to the same embodiments.

Although various features of the disclosed system and methods may be described in the context of a single embodiment, the features may also be provided separately or in any suitable combination. Conversely, although the disclosed system and methods may be described herein in the context of separate embodiments for clarity, the disclosed system and methods may also be implemented in a single embodiment.

Furthermore, it is to be understood that the disclosed system and methods can be carried out or practiced in various ways and can be implemented in embodiments other than the ones outlined in the description above.

Meanings of technical and scientific terms used herein are to be commonly understood as by one of ordinary skill in the art belong, unless otherwise defined.

Certain aspects of the present disclosure include process steps and instructions described herein in the form of a method. It should be noted that the process steps and instructions of the present disclosure could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible non-transitory computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present disclosure.

The present disclosure is well suited to a wide variety of computer network systems over numerous topologies. Within this field, the configuration and management of large networks comprise storage devices and computers that are communicatively coupled to dissimilar computers and storage devices over a network, such as the Internet, public networks, private networks, or other networks enabling communication between computing systems. Finally, it should be noted that the language used in the specification has been principally selected for readability and instructional purposes, and may not have been selected to delineate or circumscribe the inventive subject matter. Accordingly, the disclosure of the present disclosure is intended to be illustrative, but not limiting, of the scope of the disclosure, which is set forth in the following claims.

The invention claimed is:

1. A method of calibrating a fiber optic Raman spectroscope system, the system comprising a processor configured to execute program instructions, a storage device, a laser source, a primary spectrometer system and a plurality of fiber optic probes, including at least a first optic probe and a second optic probe, each of the plurality of fiber optic probes couplable to the primary spectrometer system and each of the plurality of fiber optic probes configured to transmit light from the laser source to a target and return scattered light to the primary spectrometer system the method comprising:
storing a known spectrum for a standard target in the storage device;
transmitting light from the laser source to the standard target having the known spectrum; and
for each of the plurality of fiber optic probes:
recording a calibration spectrum of the scattered light returned to the primary spectrometer system through each of the plurality of fiber optic probes from the standard target;
comparing the known spectrum and the calibration spectrum and generating with the use of the processor at least a first transfer function for the first optic probe and a second transfer function for the second optic probe;
calculating a calibration function based on at least the first transfer function and second transfer function;
storing the first transfer function, the second transfer function and the calibration function in the storage device to thereby associate at least the first fiber optic probe with the first transfer function and the secondary fiber optic probe with the second transfer function.

2. The method according to claim 1 further comprising:
subsequently illuminating a test subject using a selected fiber optic probe within the plurality of fiber optic probes;
recording a spectrum while illuminating the test subject; and
correcting the spectrum in accordance with the stored transfer function associated with the selected fiber optic probe.

3. The method according to claim 1 wherein the spectrometer has an associated spectrometer transfer function and the probe has an associated probe transfer function, and the transfer function is a function of the spectrometer transfer function and the probe transfer function.

4. The method according to claim 1 comprising associating the calibration function with the secondary fiber optic probe.

5. The method according to claim 1 comprising, on a secondary spectrometer system, using the primary fiber optic probe and generating a secondary system transfer function and storing the secondary system transfer function.

6. The method according to claim 5 comprising using the secondary fiber optic probe with the secondary spectrometer system and modifying the stored secondary system transfer function in accordance with the calibration function.

7. The method according to any one of claims 1 comprising an initial step of performing a wavelength-axis calibration of the secondary spectrometer system in accordance with the primary spectrometer system.

8. The method according to claim 1, further comprising:
transmitting light from the laser source to a plurality of targets;
for each target, measuring the transmitted power of the light from the laser source and the captured spectrum of the scattered light at the spectroscope;
performing a multivariate analysis of the captured spectra with the measured transmitted power as a dependent variable; and
storing a resulting model of laser power as a function of spectral characteristics of the captured spectra.

9. The method according to claim 8, further comprising:
transmitting laser light to a test target;
supplying a captured spectrum to the model; and
calculating an estimate of the transmitted power.

10. A method of operating a fiber optic Raman spectroscope system within a plurality of fiber optic Raman spectroscope systems, the plurality of fiber optic Raman spectroscope systems including each of a master Raman spectroscope system having a master spectrometer and a laser source, and at least one secondary Raman spectroscope system, each secondary Raman spectroscope system having a corresponding secondary spectroscope distinct from the master spectroscope and a laser source, the master Raman spectroscope system couplable to a primary fiber optic probe and/or a plurality of secondary fiber optic probes, each secondary Raman spectroscope system couplable to the primary fiber optic probe and/or the plurality of secondary fiber optic probes, the method comprising:
(A) storing a known spectrum for a standard source and providing the standard source having the known spectrum; and
(B) for each secondary Raman spectroscope system, performing a wavelength calibration of the secondary spectrometer thereof to the master spectrometer of the master Raman spectroscope system; and
(C) performing a first calibration process for each secondary Raman spectroscope system, the first calibration process comprising:
(i) determining a plurality of transfer functions, each of the plurality of transfer functions corresponding to a selected secondary fiber optic probe coupled to the secondary Raman spectroscope system, each of the plurality of transfer functions establishing a mathematical relationship between the known spectrum and a measured calibration spectrum obtained while the selected secondary fiber optic probe is coupled to the secondary Raman spectroscope system; and (ii) associating each selected secondary fiber optic probe with the transfer function determined therefor;

or (D) performing a second calibration process comprising:
(i) for each secondary Raman spectroscope system:
(a) determining a system transfer function corresponding to the secondary Raman spectroscope system while the primary fiber optic probe is coupled thereto during measurement thereby of a calibration spectrum of scattered light received from the standard source; and
(b) associating the secondary Raman spectroscopy system with the system transfer function determined therefor; and
(ii) for each secondary fiber optic probe:
(a) determining a calibration function for the secondary fiber optic probe, the calibration function corresponding to the secondary fiber optic probe coupled to the master Raman spectroscope system during measurement of a spectrum of scattered light received from the standard source; and
(b) associating the secondary fiber optic probe with the calibration function determined therefor.

11. The method according to claim 10 wherein the plurality of secondary fiber optic probes comprises a plurality of reserve probes for a selected secondary Raman spectroscope system, and wherein the first calibration process is performed for the selected secondary Raman spectroscope system to determine a transfer function corresponding to each of the reserve probes.

12. The method according to claim 10 comprising performing the second calibration process to match any plurality of secondary fiber optic probes to any number of secondary Raman spectroscope systems such that spectra captured using different secondary Raman spectroscope systems and different secondary fiber optic probes are consistent and comparable.

13. A Raman spectroscope system comprising:
a laser source;
a primary spectrometer system;
a plurality of fiber optic probes, including at least a first fiber optic probe and a secondary fiber optic probe, each of the plurality of fiber optic probes couplable to the primary spectrometer system and, when coupled to the primary system, configured to transmit light from the laser source to a target and return scattered light to the primary spectrometer system;
a storage device;
a first transfer function for the primary fiber optic probe and a second transfer function for the secondary optic probe stored in the storage device;
a calibration function based on the first transfer function and the second transfer function; and
a computer having a processor configured to execute program instructions such that the system is operable to:
transmit light from the laser source to a target having a known spectrum using a selected one of the plurality of fiber optic probes;
record a spectrum of the scattered light from the target; and
modify the recorded spectrum in accordance with the stored transfer function corresponding to the selected fiber optic probe.

14. The system according to claim 13 wherein the stored transfer function corresponds to the spectrometer and the selected fiber optic probe.

15. The system according to claim 13 wherein the stored transfer function corresponds to the spectrometer and a primary fiber optic probe distinct from the selected fiber optic probe, and the computer is further configured to execute program instructions such that the system is operable to modify the stored transfer function in accordance with a stored calibration function associated with the selected fiber optic probe.

* * * * *